(12) United States Patent
Regev et al.

(10) Patent No.: US 12,402,610 B2
(45) Date of Patent: Sep. 2, 2025

(54) METHODS AND COMPOSITIONS FOR MODULATING INNATE LYMPHOID CELL PATHOGENIC EFFECTORS

(71) Applicants: The Broad Institute, Inc., Cambridge, MA (US); Massachusetts Institute of Technology, Cambridge, MA (US); Yale University, New Haven, CT (US)

(72) Inventors: Aviv Regev, Cambridge, MA (US); Piotr Bielecki, New Haven, CT (US); Richard Flavell, New Haven, CT (US); Monika Kowalczyk, Cambridge, MA (US); Samantha Riesenfeld, Cambridge, MA (US); Jan-Christian Huetter, Cambridge, MA (US); Elena Torlai Triglia, Cambridge, MA (US)

(73) Assignees: The Broad Institute, Inc., Cambridge, MA (US); Massachusetts Institute of Technology, Cambridge, MA (US); Yale University, New Haven, CT (US)

( * ) Notice: Subject to any disclaimer, the term of this patent is extended or adjusted under 35 U.S.C. 154(b) by 1257 days.

(21) Appl. No.: 16/681,050

(22) Filed: Nov. 12, 2019

(65) Prior Publication Data
US 2020/0146269 A1 May 14, 2020

Related U.S. Application Data

(60) Provisional application No. 62/758,117, filed on Nov. 9, 2018.

(51) Int. Cl.
| | | |
|---|---|---|
| *A61K 38/22* | (2006.01) | |
| *A01K 67/0278* | (2024.01) | |
| *A61K 38/20* | (2006.01) | |
| *A61K 40/10* | (2025.01) | |
| *A61K 40/22* | (2025.01) | |
| *A61K 40/41* | (2025.01) | |
| *C12N 15/10* | (2006.01) | |
| *C12N 15/113* | (2010.01) | |
| *C12Q 1/6881* | (2018.01) | |
| *G01N 33/50* | (2006.01) | |
| *G01N 33/569* | (2006.01) | |
| *A61K 48/00* | (2006.01) | |
| *C12N 5/078* | (2010.01) | |
| *C12N 9/22* | (2006.01) | |
| *C12N 15/115* | (2010.01) | |
| *C12N 15/85* | (2006.01) | |
| *C12N 15/90* | (2006.01) | |

(52) U.S. Cl.
CPC .......... *A01K 67/0278* (2013.01); *A61K 38/20* (2013.01); *A61K 40/10* (2025.01); *A61K 40/22* (2025.01); *A61K 40/416* (2025.01); *C12N 15/102* (2013.01); *C12N 15/113* (2013.01); *C12Q 1/6881* (2013.01); *G01N 33/5047* (2013.01); *G01N 33/56972* (2013.01); *A01K 2227/105* (2013.01); *A01K 2267/0325* (2013.01); *A01K 2267/0368* (2013.01); *A01K 2267/0387* (2013.01); *A61K 48/00* (2013.01); *A61K 2239/31* (2023.05); *A61K 2239/38* (2023.05); *C12N 5/0634* (2013.01); *C12N 9/22* (2013.01); *C12N 15/115* (2013.01); *C12N 15/85* (2013.01); *C12N 15/907* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,737,323 A | 4/1988 | Martin et al. |
| 4,837,028 A | 6/1989 | Allen |
| 5,143,854 A | 9/1992 | Fodor et al. |
| 5,288,644 A | 2/1994 | Beavis et al. |
| 5,324,633 A | 6/1994 | Fodor et al. |
| 5,432,049 A | 7/1995 | Fischer et al. |
| 5,470,710 A | 11/1995 | Weiss et al. |
| 5,492,806 A | 2/1996 | Drmanac et al. |
| 5,503,980 A | 4/1996 | Cantor |
| 5,510,270 A | 4/1996 | Fodor et al. |
| 5,525,464 A | 6/1996 | Drmanac et al. |
| 5,547,839 A | 8/1996 | Dower et al. |
| 5,580,732 A | 12/1996 | Grossman et al. |

(Continued)

FOREIGN PATENT DOCUMENTS

| | | |
|---|---|---|
| EP | 0 404 097 A2 | 12/1990 |
| EP | 0 785 280 A2 | 7/1997 |

(Continued)

OTHER PUBLICATIONS

Zhang et al., "Cutting Edge: Notch Signaling Promotes the Plasticity of Group-2 Innate Lymphoid Cells", Journal of Immunology, vol. 198, No. 5, Mar. 1, 2017, 1798-1803.

(Continued)

*Primary Examiner* — Michael D Pak

(74) *Attorney, Agent, or Firm* — Foley & Lardner LLP; Sunit Talapatra

(57) ABSTRACT

The subject matter disclosed herein is generally directed to methods and compositions for modulating inflammation driven by differentiation of quiescent tissue-resident ILCs into a spectrum of pathogenic effectors. The subject matter disclosed herein is also generally directed to detecting and monitoring an ILC response. Additionally, the subject matter is directed to treating skin inflammation, such as psoriasis.

29 Claims, 67 Drawing Sheets

Specification includes a Sequence Listing.

(56) References Cited

U.S. PATENT DOCUMENTS

| | | |
|---|---|---|
| 5,580,737 A | 12/1996 | Polisky et al. |
| 5,641,870 A | 6/1997 | Rinderknecht et al. |
| 5,660,985 A | 8/1997 | Pieken et al. |
| 5,661,028 A | 8/1997 | Foote |
| 5,800,992 A | 9/1998 | Fodor et al. |
| 5,811,097 A | 9/1998 | Allison et al. |
| 5,869,326 A | 2/1999 | Hofmann |
| 6,479,626 B1 | 11/2002 | Kim et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,794,136 B1 | 9/2004 | Eisenberg et al. |
| 6,824,978 B1 | 11/2004 | Cox et al. |
| 6,866,997 B1 | 3/2005 | Choo et al. |
| 6,903,185 B2 | 6/2005 | Kim et al. |
| 6,933,113 B2 | 8/2005 | Case |
| 6,979,539 B2 | 12/2005 | Cox et al. |
| 7,013,219 B2 | 3/2006 | Case et al. |
| 7,030,215 B2 | 4/2006 | Liu et al. |
| 7,220,719 B2 | 5/2007 | Case et al. |
| 7,241,573 B2 | 7/2007 | Choo et al. |
| 7,241,574 B2 | 7/2007 | Choo et al. |
| 7,585,849 B2 | 9/2009 | Liu et al. |
| 7,595,376 B2 | 9/2009 | Kim et al. |
| 8,021,867 B2 | 9/2011 | Smith et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 2004/0171156 A1 | 9/2004 | Hartley et al. |
| 2006/0013842 A1 | 1/2006 | Matkin et al. |
| 2011/0265198 A1 | 10/2011 | Gregory et al. |
| 2012/0017290 A1 | 1/2012 | Cui et al. |
| 2013/0236946 A1 | 9/2013 | Gouble |
| 2014/0027323 A1 | 1/2014 | Schroeder |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2016/0060691 A1 | 3/2016 | Giresi et al. |
| 2016/0106813 A1* | 4/2016 | Bomsel ............ A61K 38/23 435/7.1 |
| 2016/0208243 A1 | 7/2016 | Zhang et al. |
| 2016/0208323 A1 | 7/2016 | Bernstein et al. |
| 2017/0047193 A1 | 2/2017 | Jiang et al. |
| 2017/0211142 A1 | 7/2017 | Smargon et al. |
| 2018/0291093 A1* | 10/2018 | Benschop ......... A61P 19/00 |
| 2019/0233527 A1* | 8/2019 | Kahvejian ......... A61K 38/23 |

FOREIGN PATENT DOCUMENTS

| | | |
|---|---|---|
| EP | 0 373 203 B2 | 2/2007 |
| EP | 2 784 162 A1 | 10/2014 |
| EP | 2 784 162 B1 | 10/2014 |
| EP | 2 771 468 B1 | 2/2015 |
| EP | 2 764 103 B1 | 8/2015 |
| EP | 3 009 511 A2 | 4/2016 |
| WO | 93/11161 A1 | 6/1993 |
| WO | 95/21265 A1 | 8/1995 |
| WO | 96/31622 A1 | 10/1996 |
| WO | 96/40281 A2 | 12/1996 |
| WO | 97/10365 A1 | 3/1997 |
| WO | 97/27317 A1 | 7/1997 |
| WO | 97/49450 A1 | 12/1997 |
| WO | 98/52609 A1 | 11/1998 |
| WO | 2009/012418 A2 | 1/2009 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/204723 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | WO-2014/210353 A2 | 12/2014 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089473 A1 | 6/2015 |
| WO | 2015/089486 A2 | 6/2015 |
| WO | WO-2015/089419 A1 | 6/2015 |
| WO | 2016/028682 A1 | 2/2016 |
| WO | 2016/040476 A1 | 3/2016 |
| WO | 2016/049163 A2 | 3/2016 |
| WO | 2016/049258 A2 | 3/2016 |
| WO | 2016/069591 A2 | 5/2016 |
| WO | 2016/094867 A1 | 6/2016 |
| WO | 2016/094872 A1 | 6/2016 |
| WO | 2016/094874 A1 | 6/2016 |
| WO | 2016/094880 A1 | 6/2016 |
| WO | 2016/106244 A1 | 6/2016 |
| WO | 2016/161516 A1 | 10/2016 |
| WO | 2016/168584 A1 | 10/2016 |
| WO | 2016/205749 A1 | 12/2016 |
| WO | 2016/205759 A1 | 12/2016 |
| WO | 2017/070605 A1 | 4/2017 |
| WO | 2017/156336 A1 | 9/2017 |
| WO | 2017/164936 A1 | 9/2017 |
| WO | 2017/219027 A1 | 12/2017 |
| WO | 2018/005873 A1 | 1/2018 |
| WO | 2018/035250 A1 | 2/2018 |
| WO | 2015/089465 A1 | 6/2018 |
| WO | 2018/170333 A1 | 9/2018 |
| WO | 2019/005866 A1 | 1/2019 |

(56) References Cited

FOREIGN PATENT DOCUMENTS

| WO | 2019/113499 A1 | 6/2019 |
|---|---|---|
| WO | 2019/213660 A2 | 11/2019 |
| WO | 2020/006049 A1 | 1/2020 |

OTHER PUBLICATIONS

Bielecki et al., "Skin Inflammation Driven by Differentiation of Quiescent Tissue-resident ILCs Into a Spectrum of Pathogenic Effectors", bioRxiv, Nov. 12, 2018, 43 pages.
Dyring-Andersen et al., "Increased Number and Frequency of Group 3 Innate Lymphoid Cells in Nonlesional Psoriatic Skin", British Journal of Dermatology, vol. 170, No. 3, Mar. 2014, 609-616.
Huang et al., "IL-25-Responsive, Lineage-negative KLRG1Hi Cells are Multipotential "Inflammatory" Type 2 Innate Lymphoid Cells", Nature Immunology, vol. 16, No. 2, Feb. 2015, 24 pages.
Teunissen et al., "Composition of Innate Lymphoid Cell Subsets in the Human Skin: Enrichment of Ncr(+) ILC3 in Lesional Skin and Blood of Psoriasis Patients", Journal of Investigative Dermatology, vol. 134, No. 9, Sep. 2014, 2351-2360.
Villanova et al., "Characterization of Innate Lymphoid Cells in Human Skin and Blood Demonstrates Increase of NKp44+ ILC3 in Psoriasis", Journal of Investigative Dermatology, vol. 134, No. 4, Apr. 2014, 984-991.
Abudayyeh et al., C2c2 is a single-component programmable RNA-guided RNA targeting CRISPR effector, Science, Aug. 5, 2016, vol. 353, No. 6299 (23 pages).
Ahn et al., "DeMix: deconvolution for mixed cancer transcriptomes using raw measured data," Bioinformatics, 2013, vol. 29 (pp. 1865-1871).
Allerson et al., "Fully 2'-Modified Oligonucleotide Duplexes with Improved in Vitro Potency and Stability Compared to Unmodified Small Interfering RNA," American Chemical Society, Journal of Medicinal Chemistry, Feb. 2005, vol. 48 (pp. 901-904).
Angerer et al., "Destiny: Diffusion Maps for Large-Scale Single-Cell Data in R", Bioinformatics, 2016, vol. 32, No. 8 (pp. 1241-1243).
Bal et al., "IL-1beta, IL-4 and IL-12 control the fate of group 2 innate lymphoid cells in human airway inflammation in the lungs," Nature Immunology, Mar. 22, 2016, vol. 17, No. 6 (pp. 636-645).
Bartel et al., "MicroRNAs: Genomics, Biogenesis, Mechanism, and Function," Cell, Jan. 23, 2004, vol. 116, No. 2 (pp. 281-297).
Bartunek et al., Avian stem cell factor (SCF): production and characterization of the recombinant His-tagged SCF of chicken and its neutralizing antibody, Cytokine, Jan. 1996, vol. 8, Issue 1 (pp. 14-20).
Bernick et al., "Interleukin-12 and -23 Control Plasticity of CD127(+) Group 1 and Group 3 Innate Lymphoid Cells in the Intestinal Lamina Propria," Immunity, 2015, vol. 43 (pp. 146-160).
Binz et al., "Engineering novel binding proteins from nonimmunoglobulin domains," Nature Biotechnology, 2005, vol. 23 (pp. 1257-1268).
Bird et al., "Single-chain antigen-binding proteins," Science, Oct. 21, 1988, vol. 242, No. 4877 (pp. 423-426).
Blei et al., "Latent Dirichlet Allocation," Journal of Machine Learning Research 3, 2003 (pp. 993-1022).
Boch et al., "Breaking The Code Of DNA Binding Specificity Of T AL-Type III Effectors," Science, Dec. 11, 2009 vol. 326, No. 5959 (pp. 1509-1512).
Bondeson et al., "Targeted Protein Degradation by Small Molecules," Annual Review of Pharmacology and Toxicology, Jan. 6, 2017, vol. 57 (pp. 107-123).
Bramsen et al., "Development of Therapeutic-Grade Small Interfering RNAs by Chemical Engineering," Frontiers in Genetics, Aug. 20, 2012, vol. 3, Article 154 (pp. 22).
Brown et al., "Propellant-Driven Aerosols of Proteins," Aerosol Science and Technology, Jan. 1996, vol. 24 (pp. 45-56).
Buenrostro et al. "Transposition of native chromatin for fast and sensitive epigenomic profiling of open chromatin, DNA-binding proteins and nucleosome position," Nature Methods, Dec. 2013, vol. 10, No. 12 (pp. 1213-1218).
Buenrostro et al., "Single-cell chromatin accessibility reveals principles of regulatory variation," Nature, Jul. 23, 2015, vol. 523, No. 7561 (pp. 486-490).
Butler et al., "Integrating Single-cell Transcriptomic Data Across Different Conditions, Technologies, and Species," Nature Biotechnology, May 2018, vol. 36, No. 5 (17 pages).
Cai et al., "Pivotal role of dermal IL-17-producing gammadelta T cells in skin inflammation, Immunity," 2011, vol. 35, No. 4 (pp. 596-610).
Canver et al., "BCL11A enhancer dissection by Cas9-mediated in situ saturating mutagenesis," Nature, vol. 527, 2015 (pp. 192-197) [including Supplementary Material].
Cao et al., "Comprehensive single cell transcriptional profiling of a multicellular organism by combinatorial indexing," bioRxiv preprint first posted online Feb. 2, 2017 (35 pages).
Cao et al., "Comprehensive single-cell transcriptional profiling of a multicellular organism," Science, Aug. 18, 2017, vol. 357, No. 6352 (pp. 661-667).
Cao et al., "Role of Kruppel-like factors in leukocyte development, function, and disease," Blood, 2010, vol. 116 (pp. 4404-4414).
Carlson et al., "Identification of Amino Acids in the Glutamate Receptor, GluR3, Important for Antibody-binding and Receptor-specific Activation," The Journal of Biological Chemistry, Apr. 25, 1997, vol. 272, No. 17 (pp. 11295-11301).
Carlson et al., "Kruppel-like factor 2 regulates thymocyte and T-cell migration," Nature, 2006, vol. 442 (pp. 299-302).
Carr et al., "Genome Engineering," Nature Biotechnology, Dec. 2009, vol. 27, No. 12 (pp. 1151-1162).
Carrelha et al., "Hierarchically related lineage-restricted fates of multipotent haematopoietic stem cells," Poster Presentations 3000-3049 / Experimental Hematology, 2018, vol. 64 (pp. S53-S68).
Cella et al., "Expansion of human NK-22 cells with IL-7, IL-2, and IL-1beta reveals intrinsic functional plasticity," Proceedings of the National Academy of Sciences, USA, 2010, vol. 107 (pp. 10961-10966).
Cermak et al., "Efficient Design and Assembly of Custom Talen and Other Tal Effector-Based Constructs for DNA Targeting", Nucleic Acids Research, 2011, vol. 39, No. 12 (pp. 1-11).
Charman, "Lipids, Lipophilic Drugs, and Oral Drug Delivery-Some Emerging Concepts," Journal of Pharmaceutical Sciences, 2000, vol. 89, No. 8 (pp. 967-978).
Chen et al., "Dynamic Imaging of Genomic Loci in Living Human Cells by an Optimized CRISPR/Cas System," Cell, 2013, vol. 155 (pp. 1479-1491).
Chen et al., "Effects of Interleukin-1a, Interleukin-1 Receptor Antagonist, and Neutralizing Antibody on Proinflammatory Cytokine Expression by Human Squamous Cell Carcinoma Lines," Cancer Research, Aug. 15, 1998, vol. 58, (pp. 3668-3676).
Chen et al., "Genome-wide CRISPR Screen in a Mouse Model of Tumor Growth and Metastasis," Cell, 2015 vol. 160 (pp. 1-15).
Chu et al., "Efficient Generation of Rosa26 Knock-in Mice using Crispr/Cas9 in C57bl/6 Zygotes," BMC Biotechnology, Jan. 16, 2016, vol. 16, No. 4 (15 pages).
Chung et al., "Polycistronic RNA polymerase II expression vectors for RNA interference based on BIC/miR-155," Nucleic Acids Research, 2006, vol. 34, No. 7 (14 pages).
Ciofani et al., "A validated regulatory network for Th17 cell specification," Cell, Oct. 12, 2012, vol. 151 (pp. 289-303).
Cong et al., "Multiplex Genome Engineering Using CRISPR-Cas Systems," Science Express, Jul. 5, 2012, Supplementary Material (pp. 1-26).
Cotten et al., "2'-O-methyl, 2'-O-ethyl oligoribonucleotides and phosphorothioate oligodeoxyribonucleotides as inhibitors of the in vitro U7 snRNP-dependent mRNA processing event," Nucleic Acids Research, vol. 19, Issue 10, May 11, 1991 (pp. 2629-2635).
Cox et al., "RNA editing with CRISPR-Cas13," Science, Nov. 24, 2017, vol. 358, No. 6366 (pp. 1019-1027).
Cox et al., "RNA editing with CRISPR-Cas13", Science, 2017, vol. 358 (pp. 1019-1027).

(56) References Cited

OTHER PUBLICATIONS

Cusanovich et al., "Multiplex single-cell profiling of chromatin accessibility by combinatorial cellular indexing" Science, May 22, 2015, vol. 348, No. 6237 (pp. 910-914).
Dellinger et al., "Streamlined process for the chemical synthesis of RNA using 2'-O-thionocarbamate-protected nucleoside phosphoramidites in the solid phase," Journal of the American Chemical Society, Aug. 3, 2011, vol. 133, No. 30 (pp. 11540-11556).
Deng et al., "An Agonist Murine Monoclonal Antibody to the Human c-Mpl Receptor Stimulates Megakaryocytopoiesis," Blood, Sep. 1998, vol. 92, No. 6 (pp. 1981-1988).
Deng et al., "CASFISH: CRISPR/Cas9-mediated in situ labeling of genomic loci in fixed cells," Proceedings of the National Academy of Sciences, USA, Sep. 22, 2015, vol. 112, No. 38 (pp. 11870-11875).
Dey et al., "Visualizing the structure of RNA-seq expression data using grade of membership models," PLoS Genetics, Mar. 23, 2017, vol. 13, No. 3 (23 pages).
Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].
Doyon et al., "Enhancing zinc-finger-nuclease activity with improved obligate heterodimeric architectures," Nature Methods, Jan. 2011, vol. 8, No. 1 (pp. 74-79).
East-Seletsky et al., "Two distinct RNase activities of CRISPR-C2c2 enable guide-RNA processing and RNA detection," Nature, Oct. 13, 2016, vol. 538, No. 7624 (pp. 270-273).
Esplunges et al., "Control of TH17 cells occurs in the small intestine," Nature, vol. 475, No. 7357 (pp. 514-518).
Galloway et al., "RNA-binding proteins ZFP36L1 and ZFP36L2 promote cell quiescence," Science, 2016, vol. 352 (pp. 453-459)[with Supplementary Materials] (39 pages).
Gao et al., "Engineered Cpf1 enzymes with altered PAM specificities," bioRxiv preprint, Dec. 4, 2016 [pp. 1/14-14/14, pp. 1/3-3/3 of Figs, and pp. S1-S8 (25 pages)].
Gasteiger et al., "Tissue residency of innate lymphoid cells in lymphoid and nonlymphoid organs," Science, Nov. 20, 2015, vol. 350, No. 6263 (pp. 981-985).
Gebauer and Skerra, Engineered protein scaffolds as next-generation antibody therapeutics, Current Opinion in Chemical Biology, 2009, vol. 13 (pp. 245-255).
Gierahn et al., "Seq-Well: Portable, Low-Cost RNA Sequencing of Single Cells at High Throughput," Nature Methods, Apr. 2017, vol. 14, No. 4 (8 pages).
Gill et al., "Biopharmaceutical drug discovery using novel protein scaffolds," Current Opinion in Biotechnology, 2006, vol. 17, No. 6 (653-658).
Gruber et al., "The Vienna RNA Websuite," Nucleic Acids Research, Apr. 19, 2008, vol. 36 (pp. W70-W74).
Gury-Ben Ari et al., "The Spectrum and Regulatory Landscape of Intestinal Innate Lymphoid Cells Are Shaped by the Microbiome," Cell, Aug. 25, 2016, vol. 166, No. 5 (pp. 1231-1246).
Habib et al., "Div-Seq: Single-nucleus RNA-Seq reveals dynamics of rare adult newborn neurons," Science, Aug. 26, 2016, vol. 353, No. 6302 (pp. 925-928).
Habib et al., "Massively parallel single-nucleus RNA-seq with DroNc-seq," Nature Methods, Oct. 2017, vol. 14, No. 10 (pp. 955-958).
Haghverdi et al., "Diffusion pseudotime robustly reconstructs lineage branching," Nature Methods, 2016, vol. 13 (pp. 845-848).
Harrop et al., "Antibodies to TR2 (Herpesvirus Entry Mediator), a New Member of the TNF Receptor Superfamily, Block T Cell Proliferation, Expression of Activation Markers, and Production of Cytokines," Journal of Immunology, 1998, vol. 161, No. 4 (pp. 1786-1794).
Hashimshony, et al., "CEL-Seq: Single-Cell RNA-Seq by Multiplexed Linear Amplification," Cell Reports, 2012, vol. 2, No. 3 (pp. 666-673).
Hendel et al., "Chemically modified guide RNAs enhance CRISPR-Cas genome editing in human primary cells," Nature Biotechnology Sep. 2015, vol. 33, No. 9 (pp. 985-989).
Hicke et al., "Escort aptamers: a delivery service for diagnosis and therapy," The Journal of Clinical Investigation, Oct. 2000, vol. 106, No. 8 (pp. 923-928).
Hobbs et al., "Polynucleotides containing 2'-amino-2'-deoxyribose and 2'-azido-2'-deoxyribose," Biochemistry, 1973, vol. 12, No. 25 (pp. 5138-5145).
Hollinger et al., "Diabodies": Small bivalent and bispecific antibody fragments, Proceedings of the National Academy of Sciences, USA, Jul. 1993, vol. 90 (pp. 6444-6448).
Howard et al., "Acute subdural hematomas: an age-dependent clinical entity," Journal of Neurosurgery, vol. 71, No. 6 (pp. 858-863).
Hsu et al., "Development and Applications of CRISPR-Cas9 for Genome Engineering," Cell, 2014, vol. 157 (pp. 1262-1278).
Hsu et al., "DNA targeting specificity of RNA-guided Cas9 nucleases", Nature Biotechnology, Sep. 2013, vol. 31, No. 9 (pp. 827-832).
Huang et al., "IL-25-responsive, lineage-negative KLRG1(hi) cells are multipotential 'inflammatory' type 2 innate lymphoid cells," Nature Immunology, Feb. 2015, vol. 16 (pp. 161-169).
Huang et al., "S1P-dependent interorgan trafficking of group 2 innate lymphoid cells supports host defense," Science, Jan. 5, 2018, vol. 359 (pp. 114-119).
Huston et al., "Protein engineering of antibody binding sites: Recovery of specific activity in an anti-digoxin single-chain Fv analogue produced in *Escherichia coli*," Proceedings of the National Academy Sciences USA, Aug. 1988, vol. 85 (pp. 5879-5883).
Inoue et al., "An inducible translocation strategy to rapidly activate and inhibit small GTPase signaling pathways," Nature Methods, Jun. 2005, vol. 2, No. 6 (pp. 415-418).
Islam, et al., "Characterization of the single-cell transcriptional landscape by highly multiplex RNA-seq," Genome Research, 2011, vol. 21, No. 7 (pp. 1160-1167).
Jiang et al., "RNA-guided editing of bacterial genomes using CRISPR-Cas systems," Nature Biotechnology, Mar. 2013, vol. 31 [including supplementary information (pp. 233-239) 30 pages].
Kalisky et al., "Genomic Analysis at the Single-Cell Level," Annual Review of Genetics, 2011, vol. 45 (pp. 431-445).
Kalisky et al., "Single-cell genomics," Nature Methods, Apr. 2011, vol. 8, No. 4 (pp. 311-314).
Keefe et al., "Aptamers as therapeutics," Nature Reviews, Jul. 2010, vol. 9 (pp. 537-550).
Kelley et al., "Versatility of chemically synthesized guide RNAs for CRISPR-Cas9 genome editing," Journal of Biotechnology, Sep. 2016, vol. 233, 10 (pp. 74-83).
Kim et al., "Chimeric restriction endonuclease.," Proceedings of the National Academy of Sciences, USA, Feb. 1994, vol. 91, No. 3 (pp. 883-887).
Kim et al., "Highly efficient RNA-guided genome editing in human cells via delivery of purified Cas9 ribonucleoproteins," Genome Research, Jun. 2014, vol. 24, No. 6 (pp. 1012-1019).
Kim et al., "Hybrid restriction enzymes: zinc finger fusions to Fok I cleavage domain," Proceedings of the National Academy of Sciences, USA, Feb. 6, 1996, vol. 93, No. 3 (pp. 1156-1160).
Klein et al., "Droplet barcoding for single-cell transcriptomics applied to embryonic stem cells," Cell, May 21, 2015, vol. 161 (pp. 1187-1201).
Kleinstiver et al., "Engineered CRISPR-Cas9 nucleases with altered PAM specificities," Nature, Jul. 23, 2015, vol. 523, No. 7561 (pp. 481-485).
Kolmar, "Alternative binding proteins: biological activity and therapeutic potential of cystine-knot miniproteins," The FEBS Journal, 2008, 275 (pp. 2684-2690).
Konermann et al., "Genome-scale transcriptional activation by an engineered CRISPR-Cas9 complex," Nature, 2015, vol. 517 (pp. 583-588) [Including Supplemental information, 12 pages].
Konermann et al., "Optical control of mammalian endogenous transcription and epigenetic states," Nature, Aug. 22, 2013, vol. 500, Includes Supplemental Information (pp. 472-476).

(56) References Cited

OTHER PUBLICATIONS

Kumari et al., "T cell antigen receptor activation and actin cytoskeleton remodeling," Biochimica et biophysica acta, Feb. 2014, vol. 1838, No. 2 (pp. 546-556).
Kuwano et al., "CD83 influences cell-surface MHC class II expression on B cells and other antigen-presenting cells," International Immunology, The Japanese Society for Immunology, 2007, vol. 19 (pp. 977-992).
Lagos-Quintana et al., "Identification of Novel Genes Coding for Small Expressed RNAs," Science, Oct. 26, 2001, vol. 294 (pp. 853-858).
Lagos-Quintana et al., "Identification of tissue-specific microRNAs from mouse," Current Biology, Apr. 30, 2002, vol. 12, (pp. 735-739).
Lagos-Quintana et al., "New microRNAs from mouse and human," RNA, 2003, vol. 9 (pp. 175-179).
Lai et al., "Modular PROTAC Design for the Degradation of Oncogenic BCR-ABL," Angewandte Chemie International Edition [Engl] Jan. 11, 2016, vol. 55, No. 2 (pp. 807-810).
Lamb et al., "The Connectivity Map: Using Gene-Expression Signatures to Connect Small Molecules, Genes, and Disease," Science, Sep. 29, 2006, vol. 313, Issue 5795 (pp. 1929-1935).
Lamb, "The Connectivity Map: A New Tool for Biomedical Research," Nature Reviews, Cancer, Jan. 2007, vol. 7, No. 1 (pp. 54-60).
Langmead and S.L. Salzberg, "Fast gapped-read alignment with Bowtie 2," Nat Meth, vol. 9, 2012 (pp. 357-359).
Lau et al., "An abundant class of tiny RNAs with probable regulatory roles in Caenorhabditis elegans," Science, Oct. 26, 2001, vol. 294 (pp. 858-862).
Laurenti et al., "From haematopoietic stem cells to complex differentiation landscapes," Nature, Jan. 24, 2018, vol. 553, No. 7689 (pp. 418-426).
Lee et al., "An Extensive Class of Small RNAs in Caenorhabditis elegans," Science, Oct. 26, 2001, vol. 294 (pp. 862-864).
Lee et al., "Synthetically modified guide RNA and donor DNA are a versatile platform for CRISPR-Cas9 engineering," Elife, May 2, 2017, vol. 6 e25312 (17 pages).
Levy-Nissenbaum et al., Nanotechnology and aptamers: applications in drug delivery, Trends in Biotechnology, Aug. 2008, vol. 26, No. 8 (pp. 442-449).
Li et al., "BATF-JUN is critical for IRF4-mediated transcription in T cells," Nature, Oct. 25, 2012, vol. 490, No. 7421 (pp. 543-546).
Li et al., "Engineering CRISPR-Cpf1 crRNAs and mRNAs to maximize genome editing efficiency," Nature Biomedical Engineering, May 2017, vol. 1, No. 5 (21 pages).
Li et al., "Epidermal Notch1 recruits RORgamma(+) group 3 innate lymphoid cells to orchestrate normal skin repair," Nature Communications, Jul. 15, 2015, vol. 7, 11394 (14 pages).
Liautard et al., "Specific Inhibition of IL-6 Signalling with Monoclonal Antibodies Against the gp130 Receptor," Cytokine, Apr. 1997, vol. 9, No. 4 (pp. 223-241).
Lim et al., "IL-12 drives functional plasticity of human group 2 innate lymphoid cells," The Journal of Experimental Medicine 2016, vol. 213, No. 4 (pp. 569-583).
Lim et al., "The microRNAs of Caenorhabditis elegans," Genes & Development, Apr. 15, 2003, vol. 17, No. 8 (pp. 991-1008).
Lim et al., "Vertebrate microRNA genes," Science, Mar. 7, 2003, vol. 299, No. 5612 (p. 1540).
Lindsay et al., "Gene Expression Deconvolution using Single-cells," Proceedings of the 2013 American Association of Human Genetics meeting, Computer Science and Engineering Molecular and Cell Biology, University of Connecticut; Data (7 pages).
Liu et al., "Cistrome: an integrative platform for transcriptional regulation studies," Genome Biology, 2011, vol. 12, R83 (10 pages).
Macosko et al., "Highly Parallel Genome-wide Expression Profiling of Individual Cells Using Nanoliter Droplets," Cell, May 21, 2015, vol. 161 (pp. 1202-1214).
Maruyama et al., "Targetability of novel immunoliposomes modified with amphipathic poly( ethylene glycol) s conjugated at their distal terminals to monoclonal antibodies," Biochimica et Biophysica Acta, 1995, vol. 1234 (pp. 74-80).
Matloubian et al., "Lymphocyte egress from thymus and peripheral lymphoid organs is dependent on S1P receptor 1," Nature, Jan. 22, 2004 vol. 427, No. 6972 (pp. 355-360).
Matsuda et al., "Controlled expression of transgenes introduced by in vivo electroporation," Proceedings of the National Academy of Sciences, Jan. 16, 2007, vol. 104, No. 3 (pp. 1027-1032).
Morocz et al., "Brain edema development after MRI-guided focused ultrasound treatment," Journal of Magnetic Resonance Imaging, Jan.-Feb. 1998, vol. 8, No. 1 (pp. 136-142).
Moscou, et al., "A Simple Cipher Governs DNA Recognition by TAL Effectors," Science, Dec. 11, 2009, vol. 326, No. 11 (p. 1501).
Moussatov et al., "A Possible Approach to The Treatment of Polycystic Ovarian Syndrome Using Focused Ultrasound," Ultrasonics, 1998, vol. 36, No. 8 (pp. 893-900).
Muller et al., "VEGF and the Fab fragment of a humanized neutralizing antibody: crystal structure of the complex at 2.4 A resolution and mutational analysis of the interface," Structure, 1998, vol. 6, No. 9 (pp. 1153-1167).
Nakamura et al., "Codon usage tabulated from the international DNA sequence databases: status for the year 2000," Nucleic Acids Research, 2000, vol. 28, No. 1 (p. 292).
Nishimasu et al., "Crystal Structure of Cas9 in Complex with Guide RNA and Target DNA", Cell, Feb. 27, 2014, vol. 156 (pp. 935-949).
Nishimasu et al., "Crystal Structure of *Staphylococcus aureus* Cas9", Cell, 2015, vol. 162 (pp. 1113-1126) [with Supplemental Information].
Nixon et al., "Engineered protein inhibitors of proteases," Current Opinion in Drug Discovery & Development, Mar. 1, 2006, vol. 9, No. 2 (pp. 261-268).
Nograles et al., "Th17 cytokines interleukin (IL)-17 and IL-22 modulate distinct inflammatory and keratinocyte-response pathways," British Journal of Dermatology, Nov. 2008, vol. 159, No. 5 (pp. 1092-1102).
Nowak et al., "Survey and Summary—Guide RNA engineering for versatile Cas9 functionality," Nucleic Acids Research, Oct. 12, 2016, vol. 44, No. 20 (pp. 9555-9564).
Nussbaum et al., "Type 2 Innate Lymphoid Cells Control Eosinophil Homeostasis," Nature, Oct. 10, 2013, vol. 502, No. 7470 (15 pages).
Nygren, "Alternative binding proteins: Affibody binding proteins developed from a small three-helix bundle scaffold," The FEBS Journal, 2008, vol. 275 (pp. 2668-2676).
Ohne al., "IL-1 is a critical regulator of group 2 innate lymphoid cell function and plasticity," Nature Immunology, Jun. 2016, vol. 17, No. 6 (pp. 646-655).
Paige et al., "RNA mimics of green fluorescent protein," Science, Jul. 29, 2011, vol. 333, No. 6042 (pp. 642-646).
Paix et al., "High Efficiency, Homology-Directed Genome Editing in Caenorhabditis elegans Using CRISPR-Cas9 Ribonucleoprotein Complexes," Genetics, Sep. 2015, vol. 201 (pp. 47-54).
Pandey et al., "Comprehensive Identification and Spatial Mapping of Habenular Neuronal Types Using Single-Cell RNA-Seq," Current Biology, Apr. 2, 2018, vol. 28, No. 7 (pp. 1052-1065).
Pantelyushin et al., "Rorgammat+ innate lymphocytes and gammadelta T cells initiate psoriasiform plaque formation in mice," The Journal of Clinical Investigation, Jun. 2012, vol. 122, No. 6 (pp. 2252-2256).
Parnas et al., "A Genome-Wide CRISPR Screen in Primary Immune Cells to Dissect Regulatory Networks," [with Supplementary Information,] 2015, vol. 162 (pp. 675-686).
Piazza et al., "Immunotherapy of Respiratory Syncytial Virus Infection in Cotton Rats(*Sigmodon fulviventer*) Using IgG in a Small-Particle Aerosol," The Journal of Infectious Diseases, vol. 166 (pp. 1422-1424).
Picelli et al. "Full-length RNA-seq from single cells using Smartseq2," Nature Protocols, Jan. 2014, vol. 9, No. 1 (pp. 171-181).
Pitard et al., "Production and characterization of monoclonal antibodies against the leukemia inhibitory factor low affinity receptor, gp190," Journal of Immunological Methods, 1997, vol. 205 pp. (177-190).
Platt et al., "CRISPR-Cas9 Knockin Mice for Genome Editing and Cancer Modeling," Cell, 2014, vol. 159 (pp. 440-455).

(56) References Cited

OTHER PUBLICATIONS

Powell et al. "Compendium of Excipients for Parenteral Formulations," PDA Journal of Pharmaceutical Science and Technology, Sep./Oct. 1998, vol. 52, No. 2 (pp. 238-311).
Prat et al., "Agonistic monoclonal antibodies against the Met receptor dissect the biological responses to HGF," Journal of Cell Science, 1998, vol. 111 (pp. 237-247).
Pritchard et al., "Inference of population structure using multilocus genotype data," Genetics, Jun. 2000, vol. 155, No. 2 (pp. 945-959).
Quon et al., "Computational purification of individual tumor gene expression profiles leads to significant improvements in prognostic prediction," Genome Medicine, 2013, vol. 5, No. 29 (20 pages).
Rahdar et al., "Synthetic CRISPR RNA-Cas9-guided genome editing in human cells," Proceedings of the American Academy of Sciences, U.S.A. Nov. 16, 2015 (pp. E7110-E7117).
Ramanan et al., "CRISPR-Cas9 cleavage of viral DNA efficiently suppresses hepatitis B virus," Nature/Scientific Reports, Jun. 2015 (9 pages).
Ramskold et al., "Full-length mRNA-Seq from single-cell levels of RNA and individual circulating tumor cells," Nature Biotechnology, Aug. 2012, vol. 30, No. 8 (777-782).
Ran et al., "Double Nicking by RNA-guided CRISPR Cas9 for enhanced genome editing specificity", Cell, Sep. 12, 2013, vol. 154 (pp. 1380-1389).
Ran et al., "Genome engineering using the CRISPR-Cas9 system," Nature Protocols, 2013, vol. 8 (pp. 2281-2308).
Ran et al., "In vivo genome editing using Staphylococcus aureus Cas9," Nature, vol. 520, 2015, (pp. 186-191). [Includes Supplemental information, 12 pages].
Repsilber et al., "Biomarker discovery in heterogeneous tissue samples—taking the in-silico deconfounding approach," BMC Bioinformatics, 2010, vol. 11, No. 27 (15 pages).
Ricardo-Gonzalez et al., "Tissue Signals Imprint ILC2 Identity with Anticipatory Function," Nature Immunology, Oct. 2018, vol. 19, No. 10 (20 pages).
Robinette et al., "Transcriptional programs define molecular characteristics of innate lymphoid cell classes and subsets," Nature Immunology, Mar. 2015, vol. 16, No. 3 (pp. 306-317).
Robinson et al., "Integrative genomics viewer," Nature Biotechnology, Jan. 2011, vol. 29, No. 1 (pp. 24-26).
Roediger et al., "Cutaneous immunosurveillance and regulation of inflammation by group 2 innate lymphoid cells," Nature Immunology, Jun. 2013, vol. 14, No. 6 (pp. 564-573).
Rohloff et al. "Nucleic acid ligands with protein-like side chains: modified aptamers and their use as diagnostic and therapeutic agents," Molecular Therapy-Nucleic Acids, 2014, vol. 3, e201 (13 pages).
Rosenberg et al., "Scaling single cell transcriptomics through split pool barcoding," bioRxiv preprint first posted online Feb. 2, 2017 (13 pages).
Rosenberg et al., "Single-cell profiling of the developing mouse brain and spinal cord with split-pool barcoding," Science, Single Cell Genomics, 2018, vol. 360 (pp. 176-182).
Salerno et al., "Translational repression of pre-formed cytokine-encoding mRNA prevents chronic activation of memory T cells," Nature Immunology, Aug. 2018, vol. 19, No. 8 (pp. 828-837).
Saudek et al., "A preliminary trial of the programmable implantable medication system for insulin delivery," New England Journal of Medicine, Aug. 31, 1989, vol. 321 (pp. 574-579).
Scaringe et al., "Advanced 5'-silyl-2'-orthoester approach to RNA oligonucleotide synthesis," Methods in Enzymology, 2000, vol. 317 (pp. 3-18).
Scaringe et al., "Novel RNA Synthesis Method Using 5'0-Silyl-2'-O-orthoester Protecting Groups," Journal of the American Chemical Society, 1998, vol. 120, No. 45 (pp. 11820-11821).
Schroder, "The multifaceted roles of the invariant chain CD74—More than just a chaperone," Biochimica et biophysica acta, 2016, vol. 1863 (1269-1281).
Schwartz et al., "Applying unmixing to gene expression data for tumor phylogeny inference," BMC Bioinformatics, 2010, vol. 11, No. 42 (20 pages).
Shalem et al., "Genome-Scale CRISPR-Cas9 Knockout Screening in Human Cells," Science, Jan. 3, 2014, vol. 343 (pp. 84-87).
Shalem et al., "High-throughput functional genomics using CRISPR-Cas9" Nature Review Genetics, 2015, vol. 16, No. 5 (pp. 299-311).
Sharma et al., "Antisense oligonucleotides: modifications and clinical trials," Medical Chemistry Journal, 2014, 5 (pp. 1454-1471).
Shen-Orr et al., "Cell type-specific gene expression differences in complex tissues," Nature Methods, Apr. 2010, vol. 7, No. 4 (pp. 287-289).
Shmakov et al., "Discovery and Functional Characterization of Diverse Class 2 CRISPR-Cas Systems," Molecular Cell, Nov. 1, 2015, vol. 60, No. 3 (pp. 385-397).
Silver et al., "Inflammatory triggers associated with exacerbations of COPD orchestrate plasticity of group 2 innate lymphoid cells in the lungs," Nature Immunology, 2016, vol. 17 (pp. 626-635).
Silverman et al., "Multivalent avimer proteins evolved by exon shuffling of a family of human receptor domains," Nature Biotechnology, 2005, vol. 23, No. 12 (pp. 1556-1561).
Skerra et al., "Alternative binding proteins: Anticalins-harnessing the structural plasticity of the lipocalin ligand pocket to engineer novel binding activities," The FEBS Journal, 2008, vol. 275 (pp. 2677-2683).
Skerra et al., "Alternative non-antibody scaffolds for molecular recognition." Current Opinion in Biotechnology, 2007, vol. 18 (pp. 295-303).
Skerra, "Engineered protein scaffolds for molecular recognition," Journal of Molecular Recognition, 2000, vol. 13 (pp. 167-187).
Slaymaker et al., "Rationally engineered Cas9 nucleases with improved specificity," Science, Jan. 1, 2016, vol. 351, No. 6268 (pp. 84-88).
Smargon et al., "Cas13b Is a Type VI-B CRISPR-Associated RNA-Guided RNases Differentially Regulated by Accessory Proteins Csx27 and Csx28," Molecular Cell Feb. 16, 2017, vol. 65, No. 4 (pp. 618-630).
Sproat et al., "New synthetic routes to synthons suitable for 2'-O-allyloligoribonucleotide assembly," Nucleic Acids Research, vol. 19, No. 4 (pp. 733-737).
Stanley et al., "Radio-Wave Heating of Iron Oxide Nanoparticles Can Regulate Plasma Glucose in Mice," Science, May 4, 2012 Vol. 336, No. 6081 (pp. 604-608).
Stegmaier et al., "Gene expression-based high-throughput screening (GE-HTS) and application to leukemia differentiation," Nature Genetics, 2004, vol. 36 (pp. 257-263).
Stumpp et al., "DARPins: a new generation of protein therapeutics," Drug Discovery Today, Aug. 2008, vol. 13, Nos. 15/16 (pp. 695-701).
Sutton et al., "Serglycin determines secretory granule repertoire and regulates natural killer cell and cytotoxic T lymphocyte cytotoxicity," The FEBS Journal, 2016, vol. 283 (pp. 947-961).
Swiech et al., "In vivo interrogation of gene function in the mammalian brain using CRISPR-Cas9," Nature Biotechnology, 2014, vol. 33 (pp. 102-106) [Including Supplemental information, 4 pages].
Taddy et al., "On Estimation and Selection for Topic Models," Proceedings of Machine Learning Research, 2012, vol. 22 (pp. 1184-1193).
Tang et al., "RNA-Seq analysis to capture the transcriptome landscape of a single cell," Nature Protocols, Mar. 2010 vol. 5, No. 3 (pp. 516-535).
Tang, et al., "mRNA-Seq whole-transcriptome analysis of a single cell," Nature Methods, May 2009, vol. 6, No. 5 (pp. 377-382).
Thorvaldsdottir et al., "Integrative Genomics Viewer (IGV): high-performance genomics data visualization and exploration," Briefings in Bioinformatics, Apr. 19, 2012, vol. 14, No. 2 (pp. 178-192).
Tran-Huu-Hue et al., "Practical Systems for the Generation of High Power Continuous Wave-Non Focused Ultrasound in the MHz Range," Acustica, acta acustica, 1997, vol. 83 (pp. 1103-1106).
Trapnell et al., "The Dynamics and Regulators of Cell Fate Decisions are Revealed by Pseudotemporal Ordering of Single Cells," Nature Biotechnology, Apr. 2014, vol. 32, No. 4 (pp. 381-386).

(56) References Cited

OTHER PUBLICATIONS

Tsai et al., "Dimeric CRISPR RNA-guided FokI nucleases for highly specific genome editing," Nature Biotechnology, 2014, vol. 32, No. 6 (pp. 569-576).
Tsukada et al., "The CCAAT/enhancer (C/EBP) family of basic-leucine zipper (bZIP) transcription factors is a multifaceted highly-regulated system for gene regulation," Cytokine, Apr. 2011, vol. 54, No. 1 (pp. 6-19).
Tuerk et al., "Systematic evolution of ligands by exponential enrichment: RNA ligands to bacteriophage T4 DNA polymerase," Science, Aug. 3, 1990, vol. 249, Issue 4968 (pp. 505-510).
Tusi et al., "Population snapshots predict early haematopoietic and erythroid hierarchies," Nature, Mar. 1, 2018, vol. 555 (pp. 54-60).
Twyman et al., "Glutamate Receptor Antibodies Activate a Subset of Receptors and Reveal an Agonist Binding Site," Neuron, Apr. 1995, vol. 14 (pp. 755-762).
Vitak et al., "Sequencing thousands of single-cell genomes with combinatorial indexing," Nature Methods, Mar. 2017, vol. 14, No. 3 (pp. 302-308).
Wallrapp et al., "The neuropeptide NMU amplifies ILC2-driven allergic lung inflammation," Nature, Sep. 21, 2017, vol. 549 (pp. 351-356).
Wang et al., "Genetic Screens in Human Cells Using the CRISPR-Cas9 System", Science, 2014, vol. 343 (pp. 80-84).
Wang et al., "UNDO: a Bioconductor R package for unsupervised deconvolution of mixed gene expressions in tumor samples," Bioinformatics, Jan. 1, 2015, vol. 31 (pp. 137-139).
Wang et al., "One-Step Generation Of Mice Carrying Mutations In Multiple Genes By CRISPR/Cas-Mediated Genome Engineering," Cell, May 9, 2013, vol. 153 (pp. 910-918).
Wang, Wei, "Lyophilization and development of solid protein pharmaceuticals", International Journal of Pharmaceutics, Aug. 2000, vol. 203, Issues 1-2 (pp. 1-60).
Ward et al., "Binding activities of a repertoire of single immunoglobulin variable domains secreted from *Escherichia coli*," Nature, Oct. 1989, vol. 341 (pp. 544-546).
Wu et al., "Genome-wide binding of the CRISPR endonuclease Cas9 in mammalian cells," Nature Biotechnology, 2014, Including Supplemental information, 2 pages (pp. 1-9).
Xu et al., "Sequence determinants of improved CRISPR sgRNA design," Genome Research, Aug. 2015, vol. 25 (pp. 1147-1157).
Yan et al., "Cas13d Is a Compact RNA-Targeting Type VI CRISPR Effector Positively Modulated by a WYL-Domain-Containing Accessory Protein," Molecular Cell, Apr. 19, 2018, vol. 70, No. 2 (pp. 327-339).
Yang et al., "Selective programming of CCR10+ innate lymphoid cells in skin-draining lymph nodes for cutaneous homeostatic regulation," Nature Immunology, Jan. 2016, vol. 17 (pp. 48-56).
Yoon et al., "Antibodies to Domains II and III of the IL-1 Receptor Accessory Protein Inhibit IL-1f Activity but Not Binding: Regulation of IL-1 Responses Is Via Type I Receptor, Not the Accessory Protein," Journal of Immunology, 2019, vol. 160, No. 7 (pp. 3170-3179).
Yosef et al., "Dynamic regulatory network controlling TH17 cell differentiation," Nature, Mar. 6, 2013, vol. 496 (pp. 461-468).
Zapata et al., "Engineering linear F(ab')2 fragments for efficient production in *Escherichia coli* and enhanced antiproliferative activity," Protein Engineering, 1995, vol. 8, No. 10 (pp. 1057-1062).
Zetsche et al., "A split-Cas9 architecture for inducible genome editing and transcription modulation", Nature Biotechnology, Feb. 2015, vol. 33, No. 2 (pp. 139-142).
Zetsche et al., "Cpf1 is a single RNA-guided endonuclease of a class 2 CRISPR-Cas system," Cell, Oct. 22, 2015, vol. 163 (pp. 759-771).
Zhang et al., "Cutting Edge: Notch Signaling Promotes the Plasticity of Group-2 Innate Lymphoid Cells," Journal of Immunology, Mar. 1, 2017, vol. 198 (pp. 1798-1803).
Zhang et al., "Model-based Analysis of ChIP-Seq (MACS)," Genome Biology, 2008, vol. 9 (pp. 1-9).
Zhang et al., "Efficient Construction of Sequence-Specific TAL Effectors for Modulating Mammalian Transcription," Nature Biotechnology, Feb. 2011, vol. 29, No. 2 (pp. 149-154).
Zheng et al. "Haplotyping germline and cancer genomes with high-throughput linked-read sequencing" Nature Biotechnology, Feb. 1, 2016, vol. 34, No. 3 (pp. 303-311) [with Supplemental Material].
Zheng et al., "Massively parallel digital transcriptional profiling of single cells," Nature Communications, Jan. 16, 2017, vol. 8, No. 14049 (12 pages).
Zhong et al., "Group 3 innate lymphoid cells continuously require the transcription factor GATA-3 after commitment," Nature Immunology, 2016, vol. 17 (pp. 169-178).
Zhou et al., "Aptamer-targeted cell-specific RNA interference," Silence, Feb. 1, 2010, vol. 1, No. 4 (10 pages).
Zhou et al., "Discovery of a Small-Molecule Degrader of Bromodomain and Extra- Terminal (BET) Proteins with Picomolar Cellular Potencies and Capable of Achieving Tumor Regression," Journal of Medicinal Chemistry 2018, vol. 61 (pp. 462-481).
Zhu et al., "Inhibition of Vascular Endothelial Growth Factor-induced Receptor Activation with Anti-Kinase Insert Domain-containing Receptor Single-Chain Antibodies from a Phage Display Library," Cancer Research, Aug. 1998, vol. 58 (pp. 3209-3214).
Zilionis et al., "Single-cell barcoding and sequencing using droplet microfluidics," Nature Protocols, 2017, vol. 12, No. 1 (pp. 44-73).
Zuker et al., "Optimal computer folding of large RNA sequences using thermodynamics and auxiliary information," Nucleic Acids Research, Jan. 10, 1981, vol. 9, No. 1 (pp. 133-148).
Chan JR, Blumenschein W, Murphy E, et al. IL-23 stimulates epidermal hyperplasia via TNF and IL-20R2-dependent mechanisms with implications for psoriasis pathogenesis. J Exp Med. 2006;203(12):2577-2587.
Wallrapp A, Burkett PR, Riesenfeld SJ, et al. Calcitonin Gene-Related Peptide Negatively Regulates Alarmin-Driven Type 2 Innate Lymphoid Cell Responses. Immunity. 2019;51(4):709-723.
Gao X, Zhang D, Xu C, Li H, Caron KM, Frenette PS. Nociceptive nerves regulate haematopoietic stem cell mobilization. Nature. 2021;589(7843):591-596.
Bielecki P, Riesenfeld SJ, Hütter JC, et al. Skin-resident innate lymphoid cells converge on a pathogenic effector state. Nature. 2021;592(7852):128-132.
Ewald DA, Noda S, Oliva M, et al. Major differences between human atopic dermatitis and murine models, as determined by using global transcriptomic profiling. J Allergy Clin Immunol. 2017;139(2):562-571.

\* cited by examiner

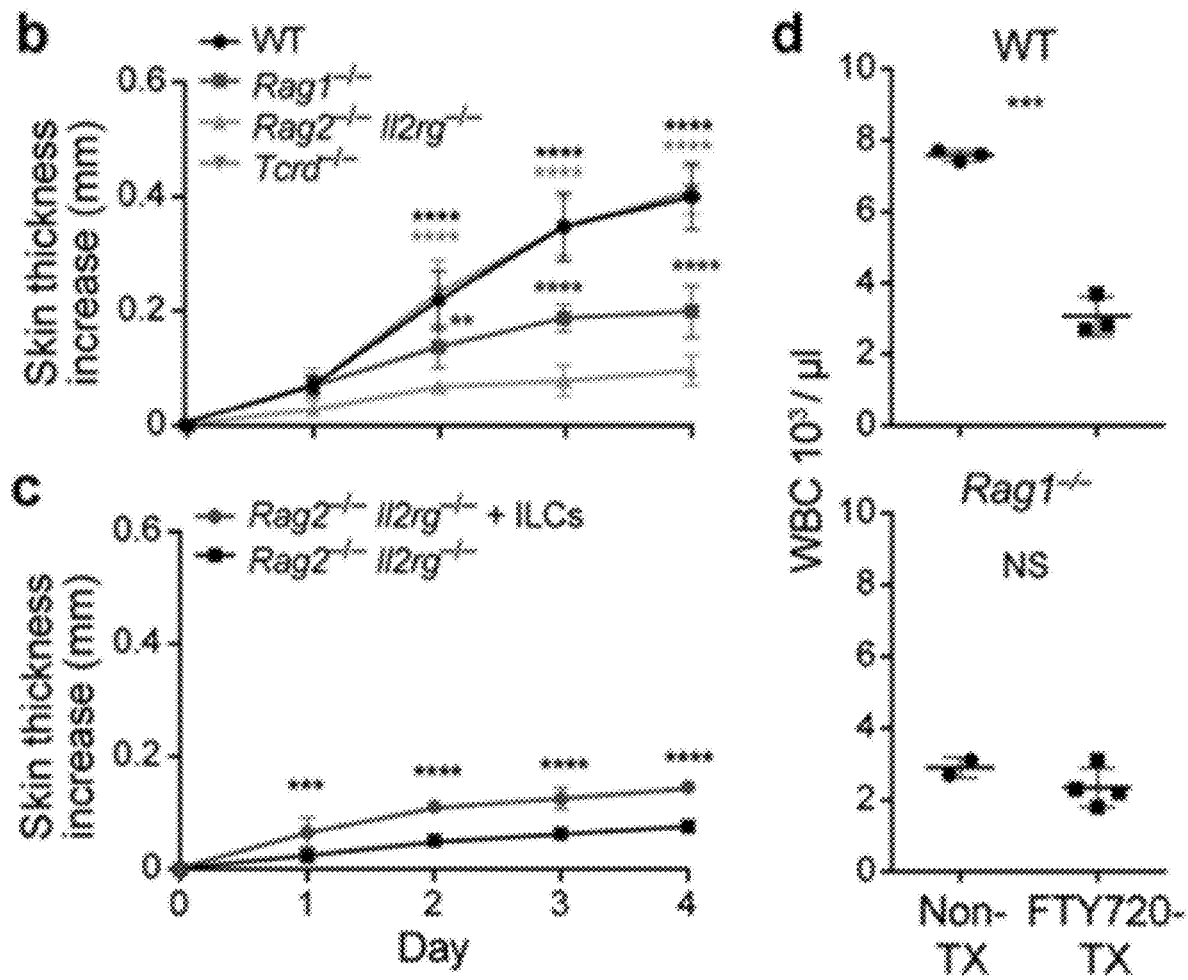
FIG. 1B-D

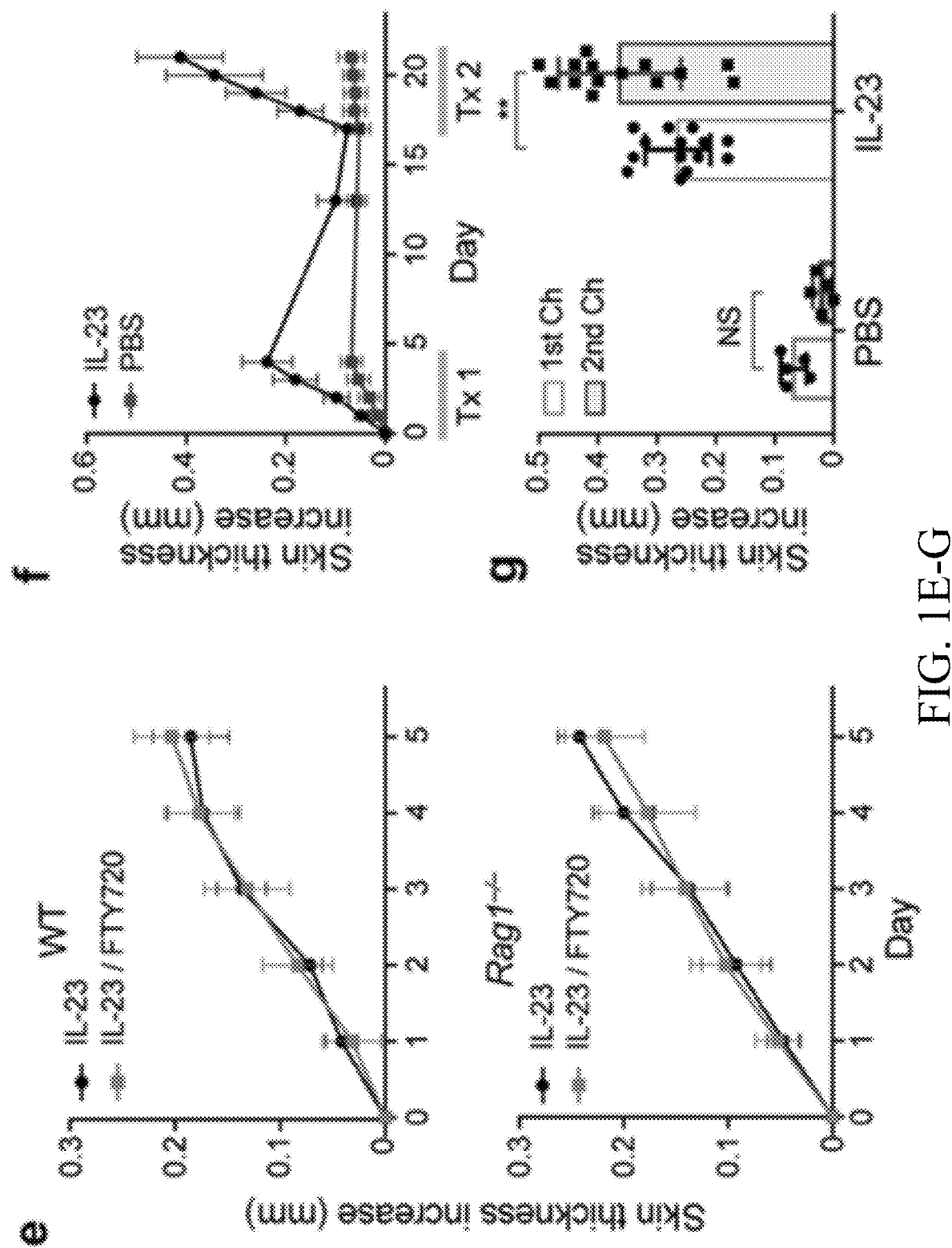
FIG. 1E-G

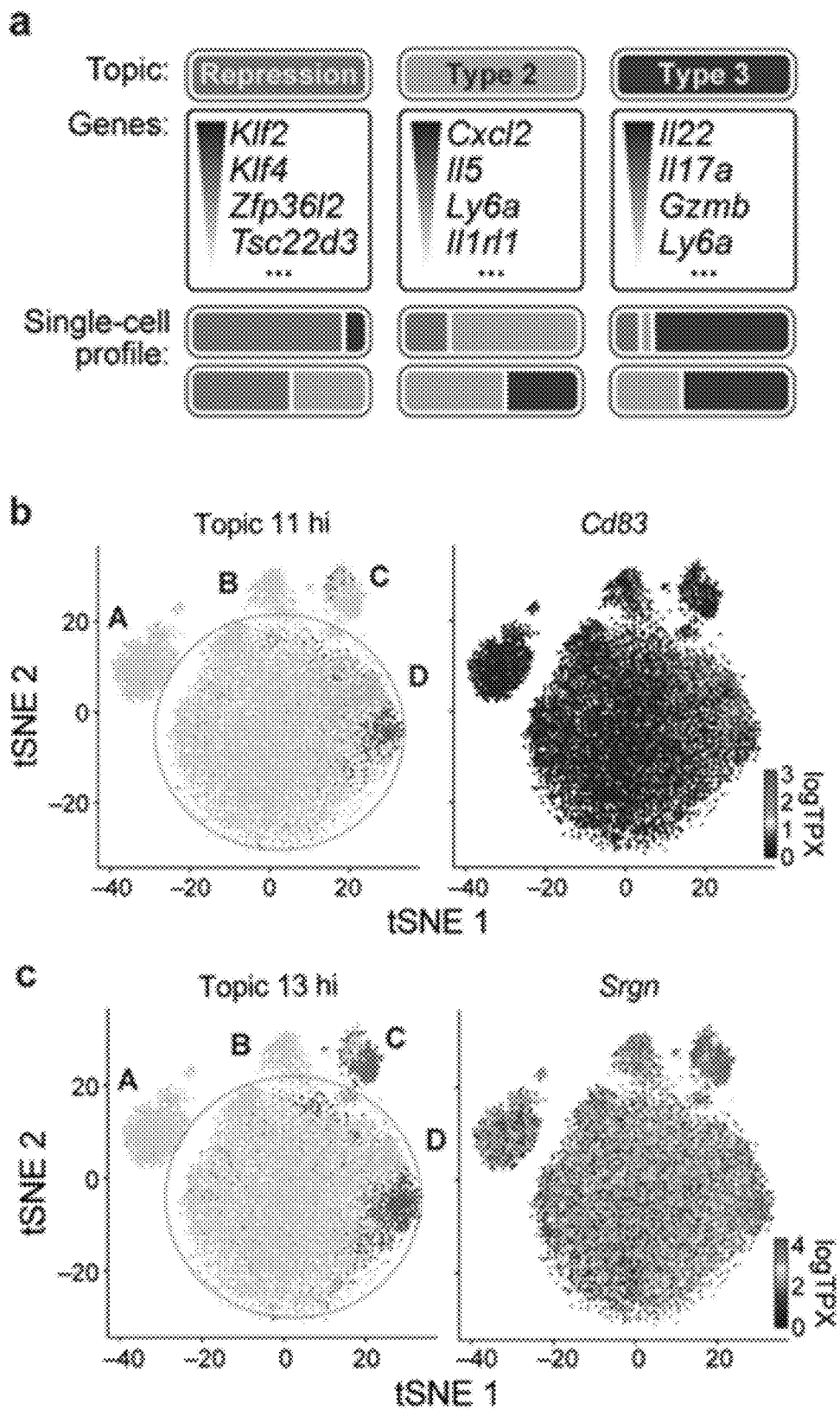
FIG. 2A-C

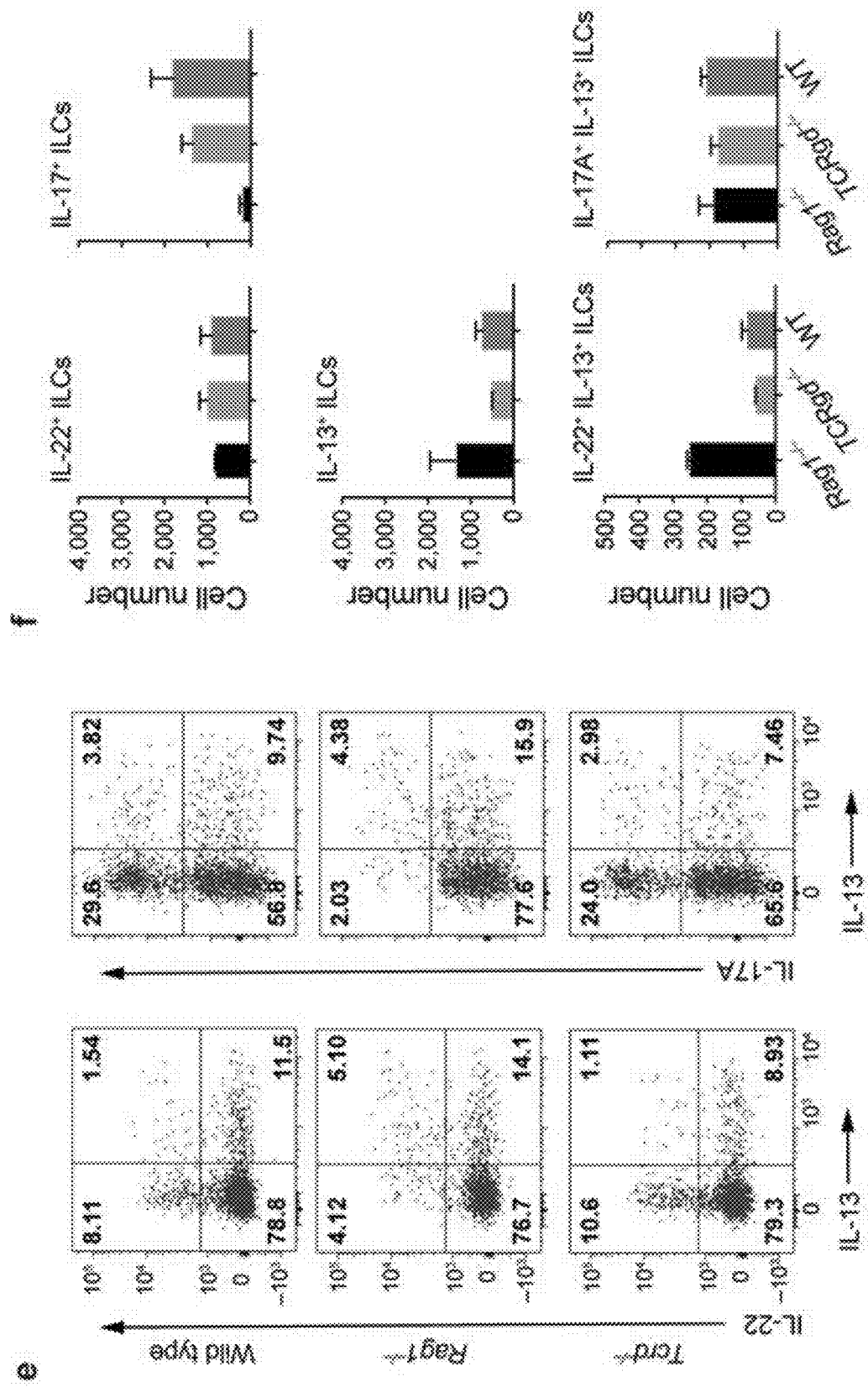
FIG. 4E-F

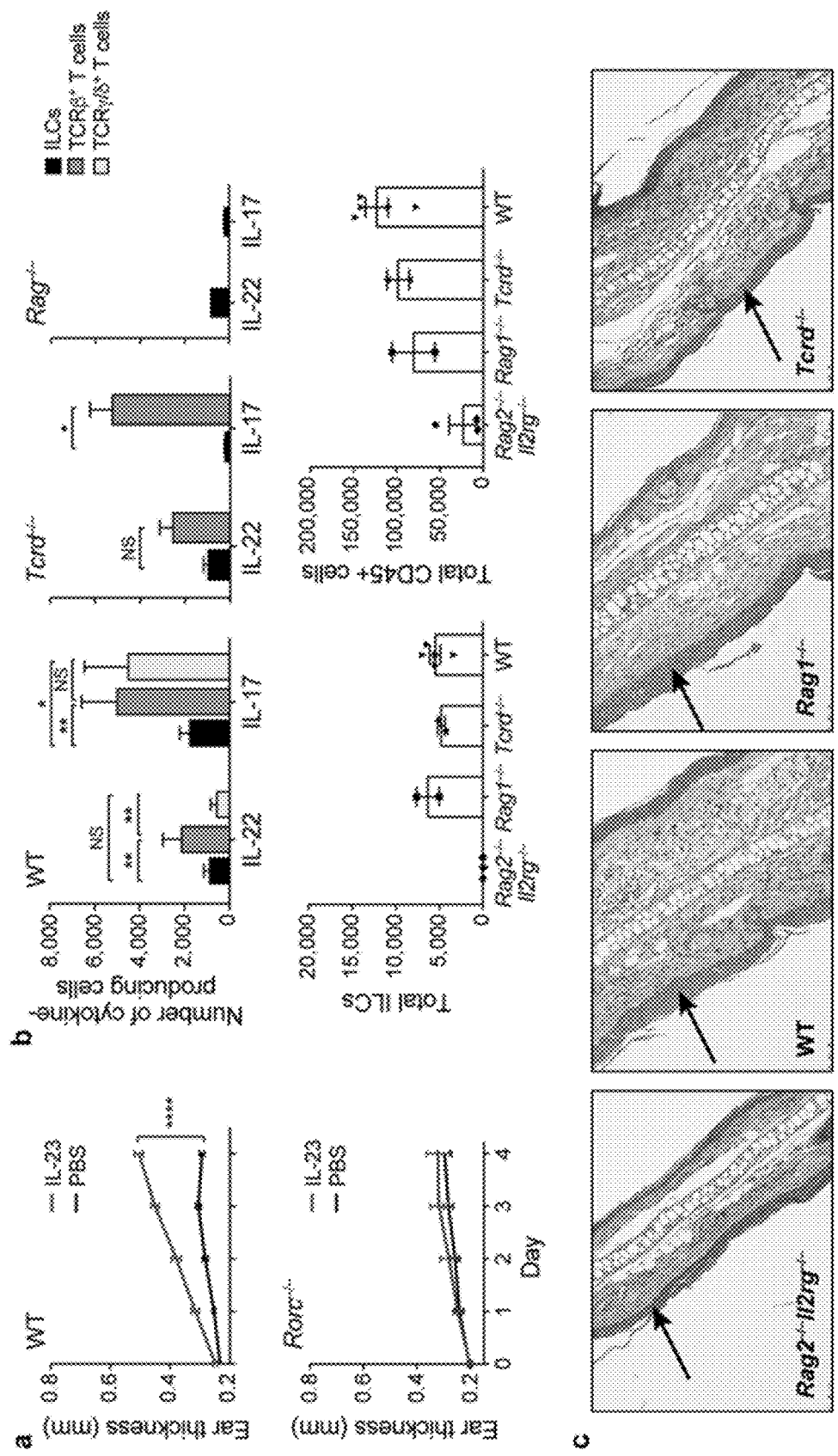
FIG. 5A-C

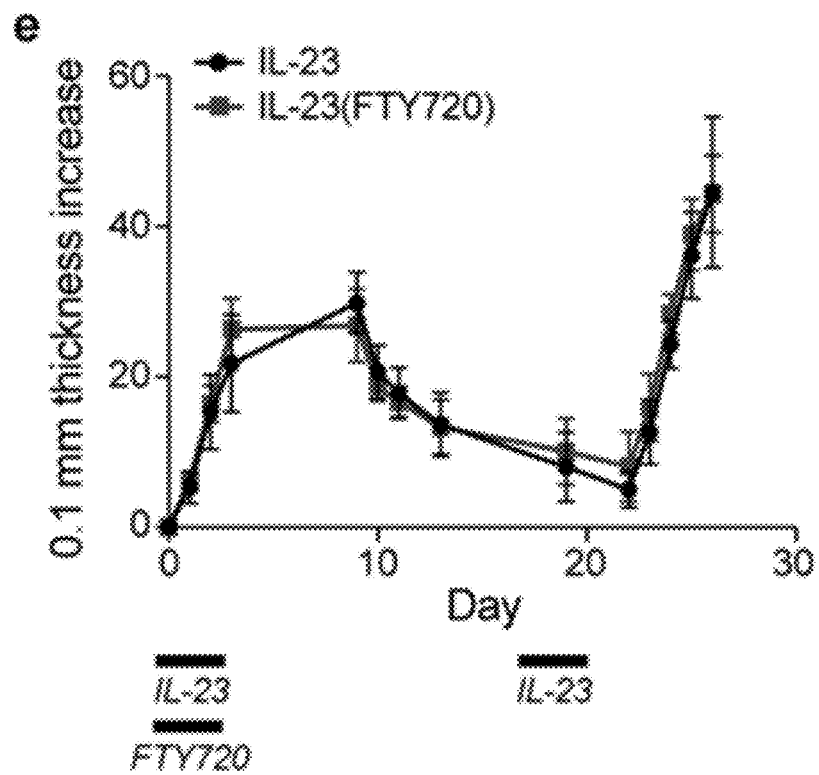
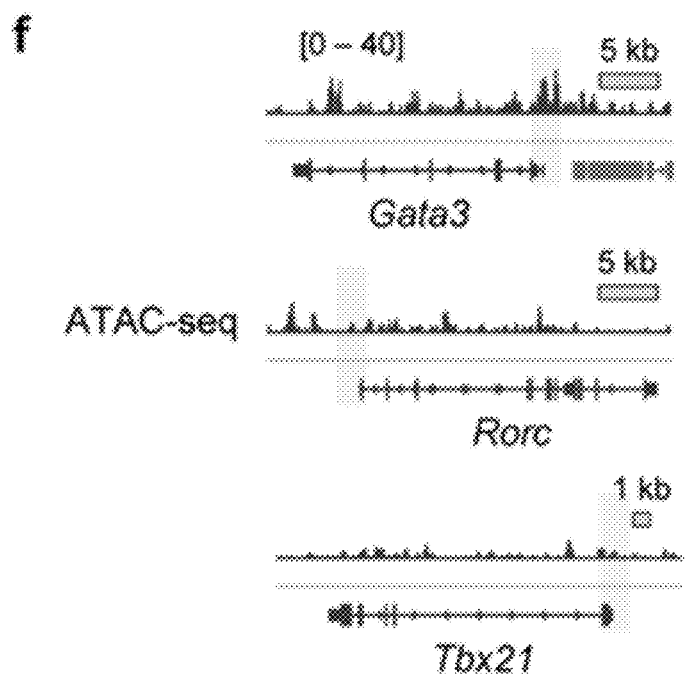
FIG. 5E-F

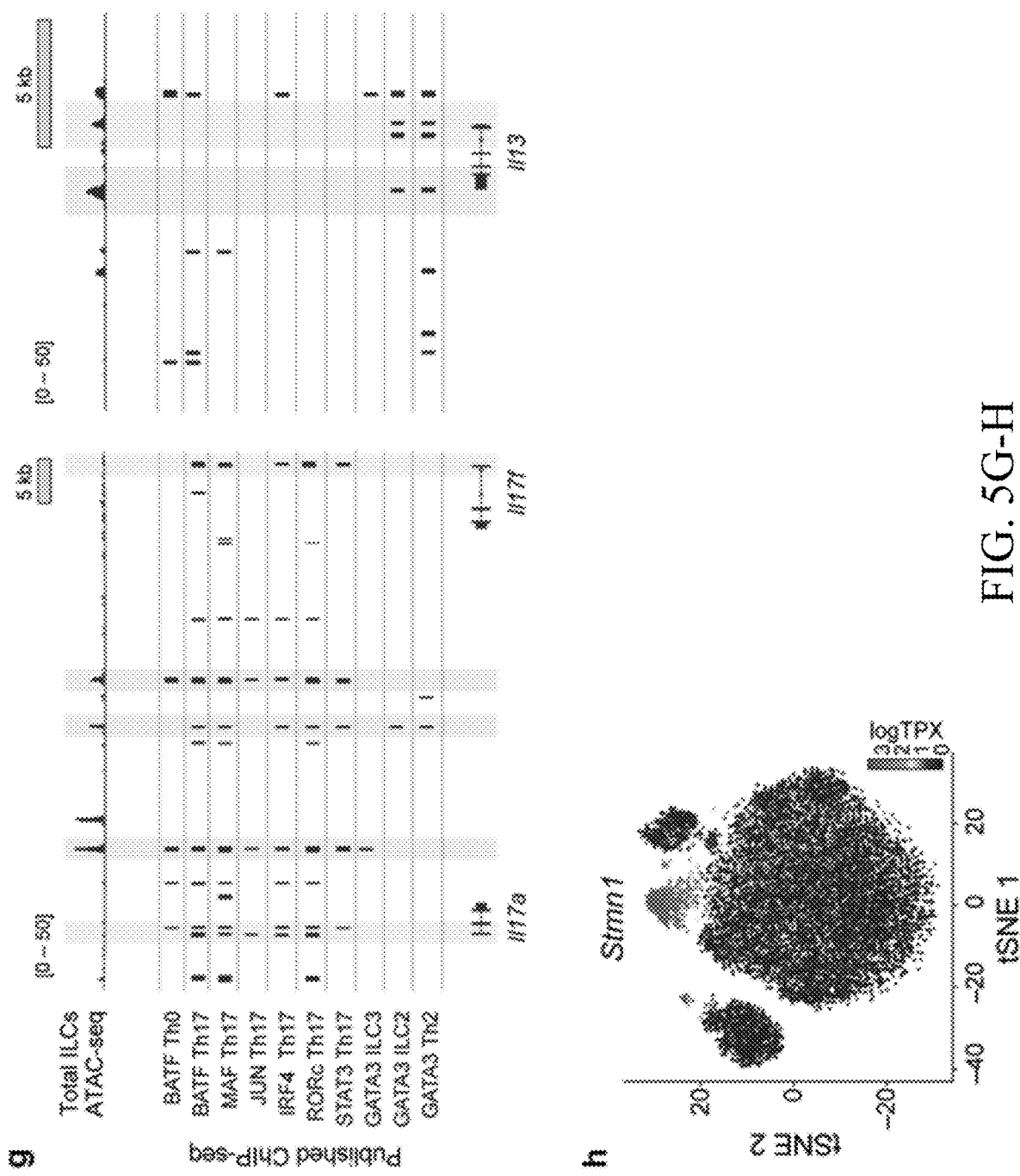
FIG. 5G-H

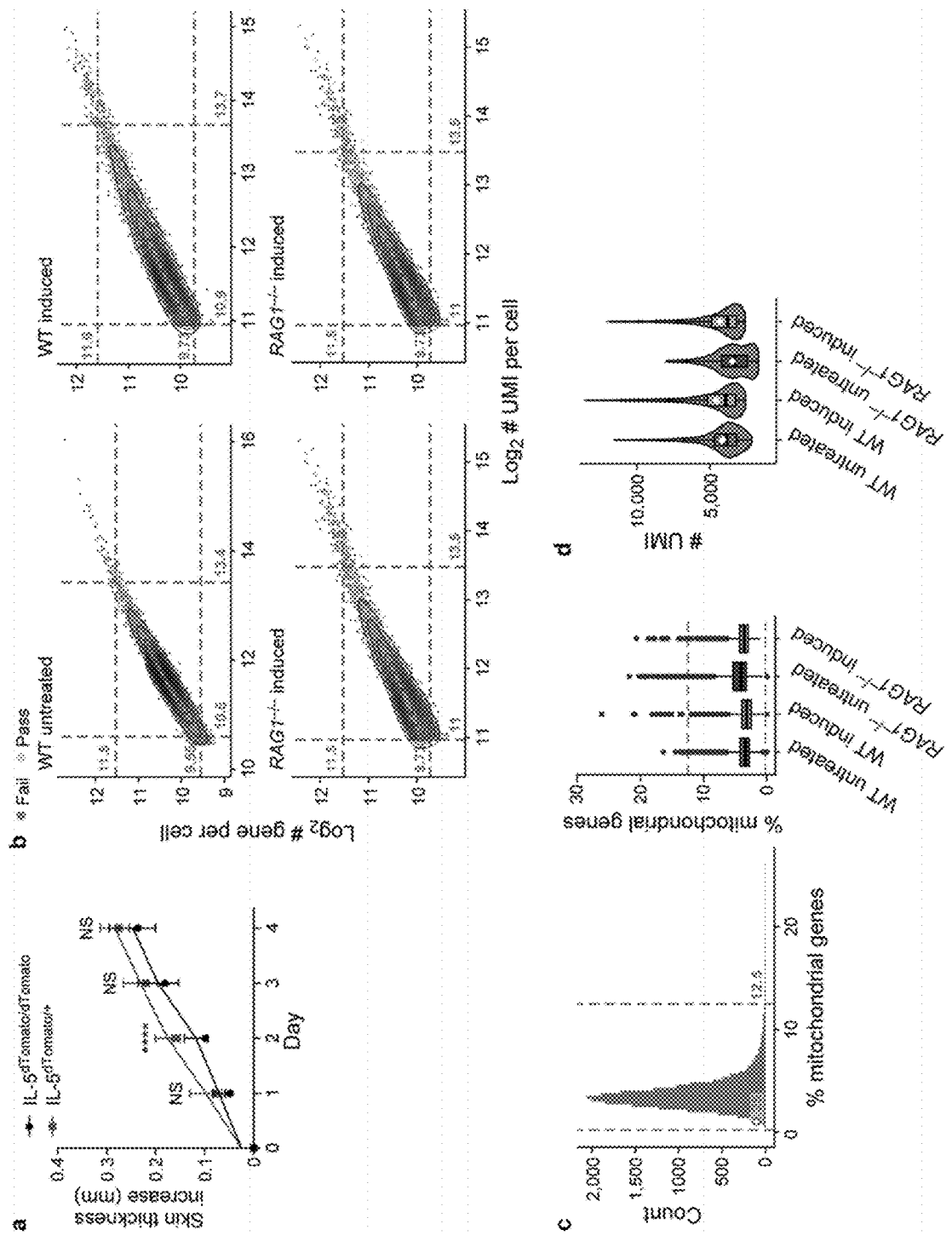
FIG. 8A-D

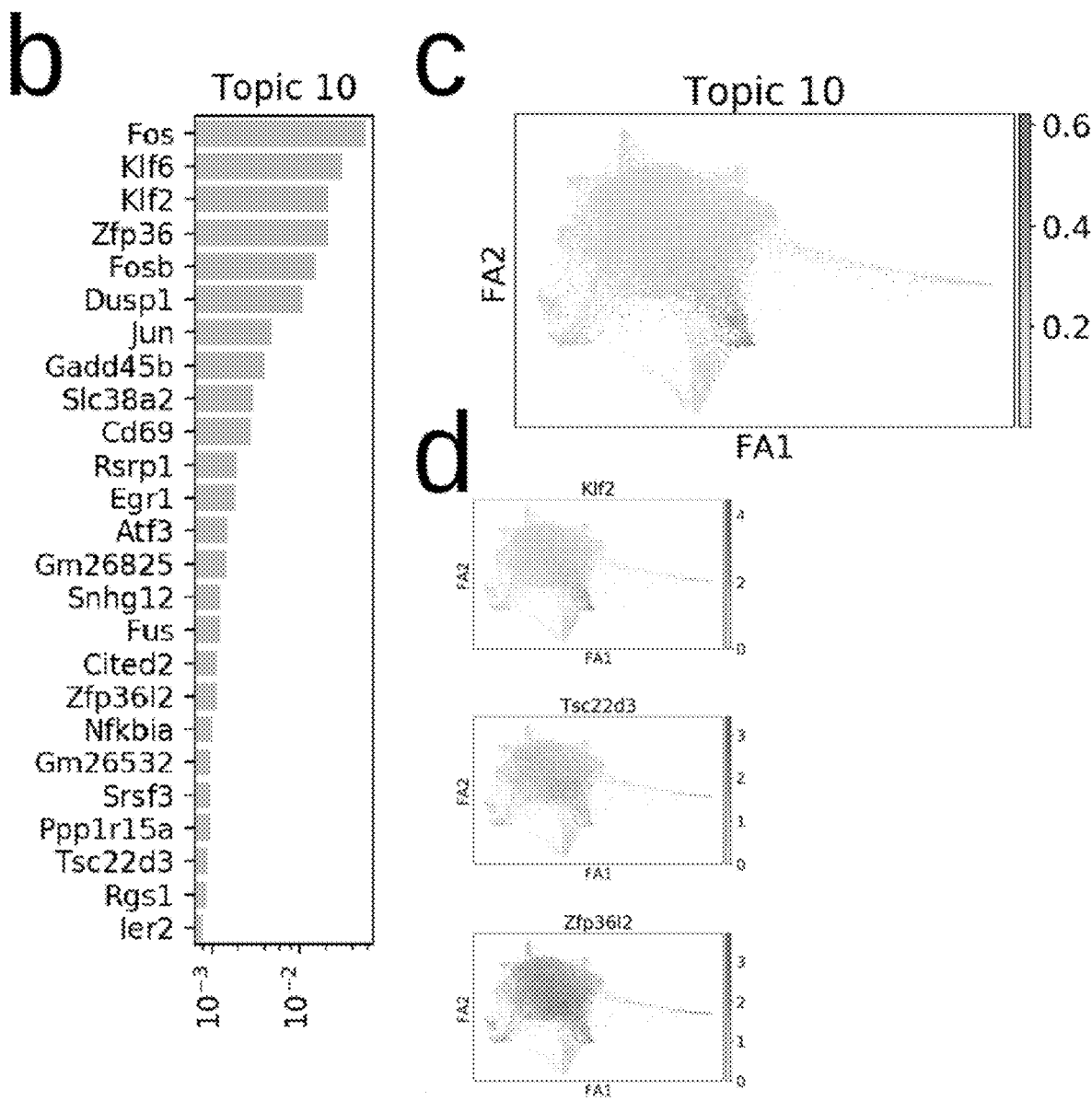
FIG. 9B-D

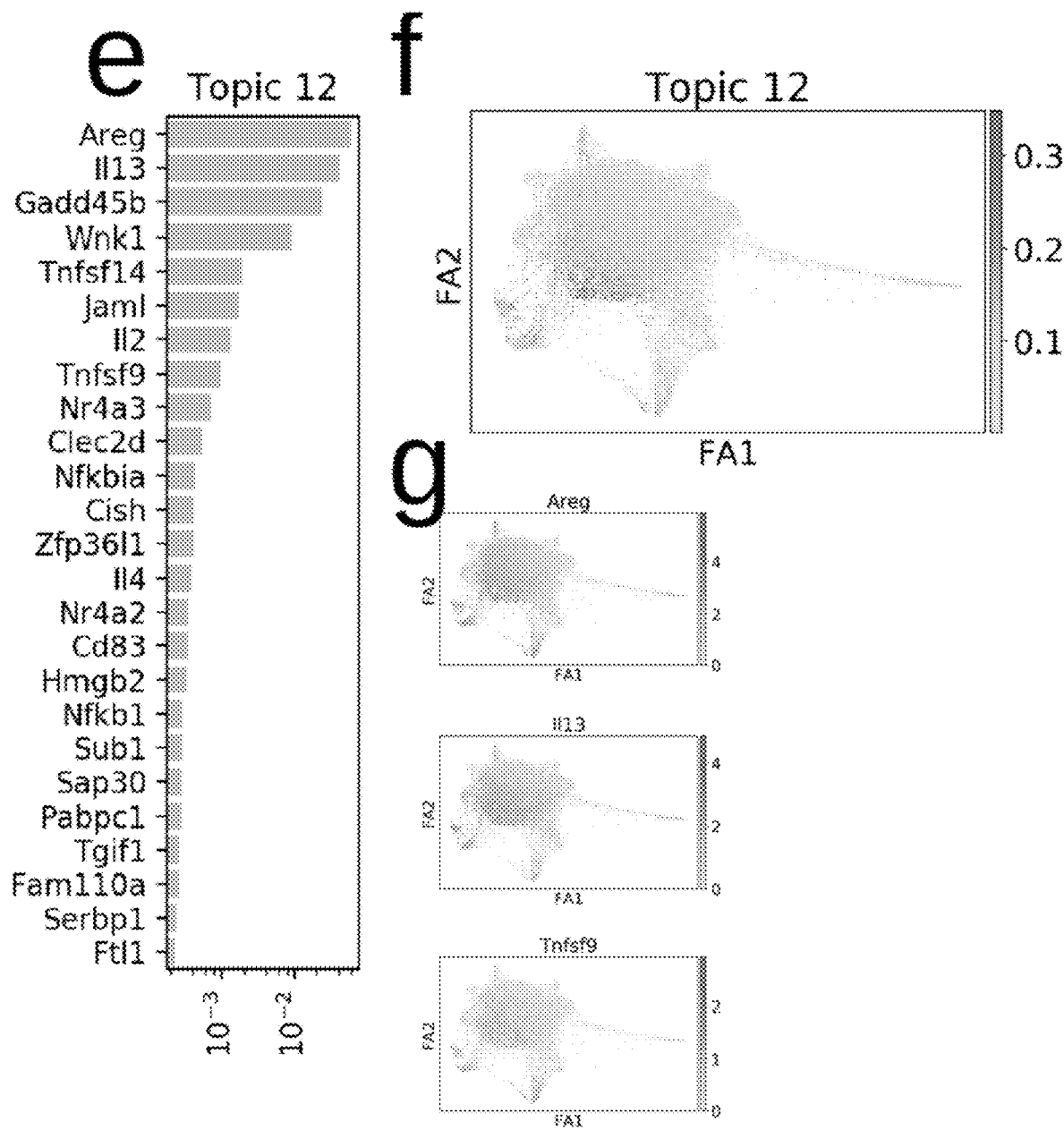
FIG. 9E-G

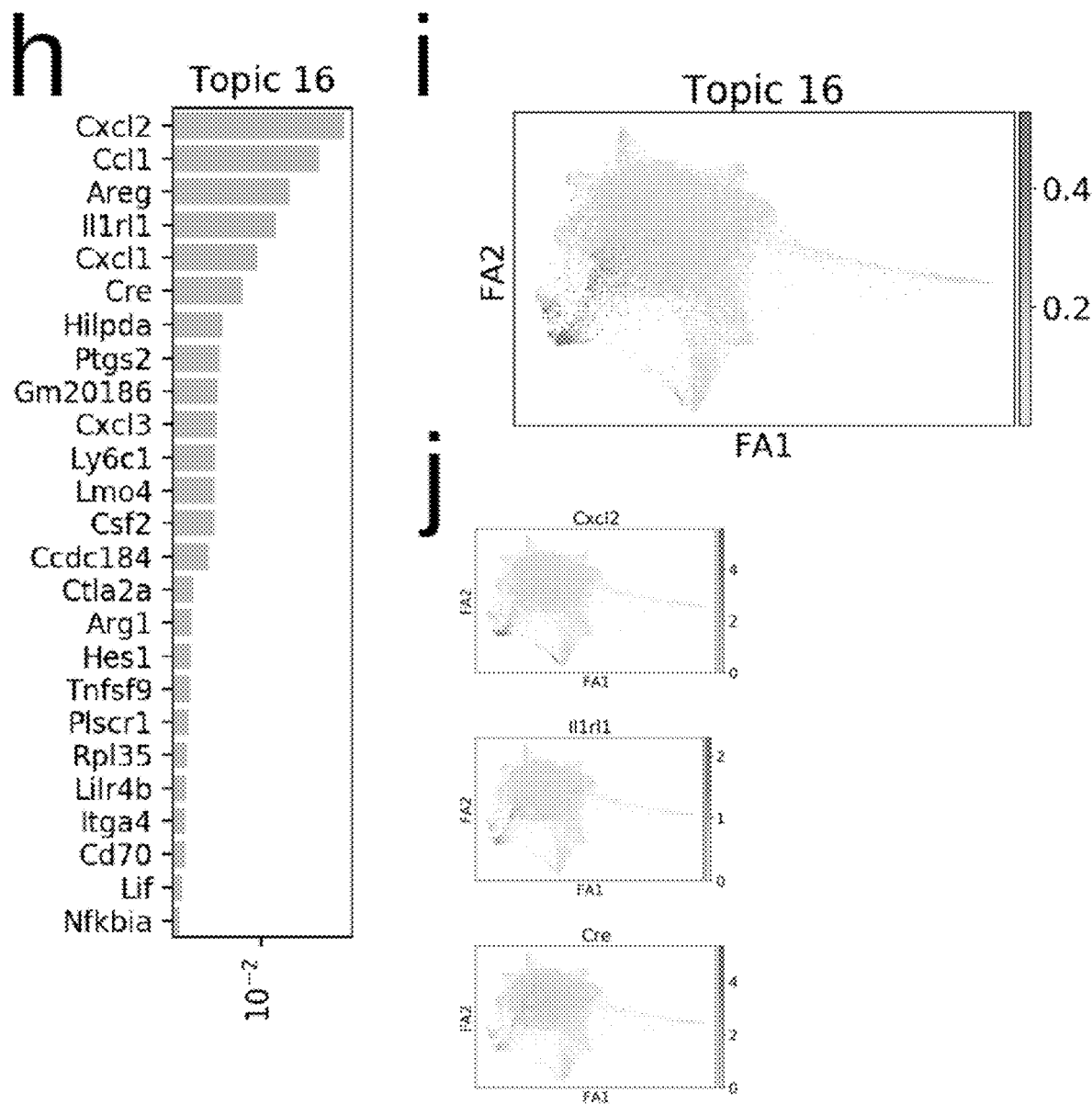
FIG. 9H-J

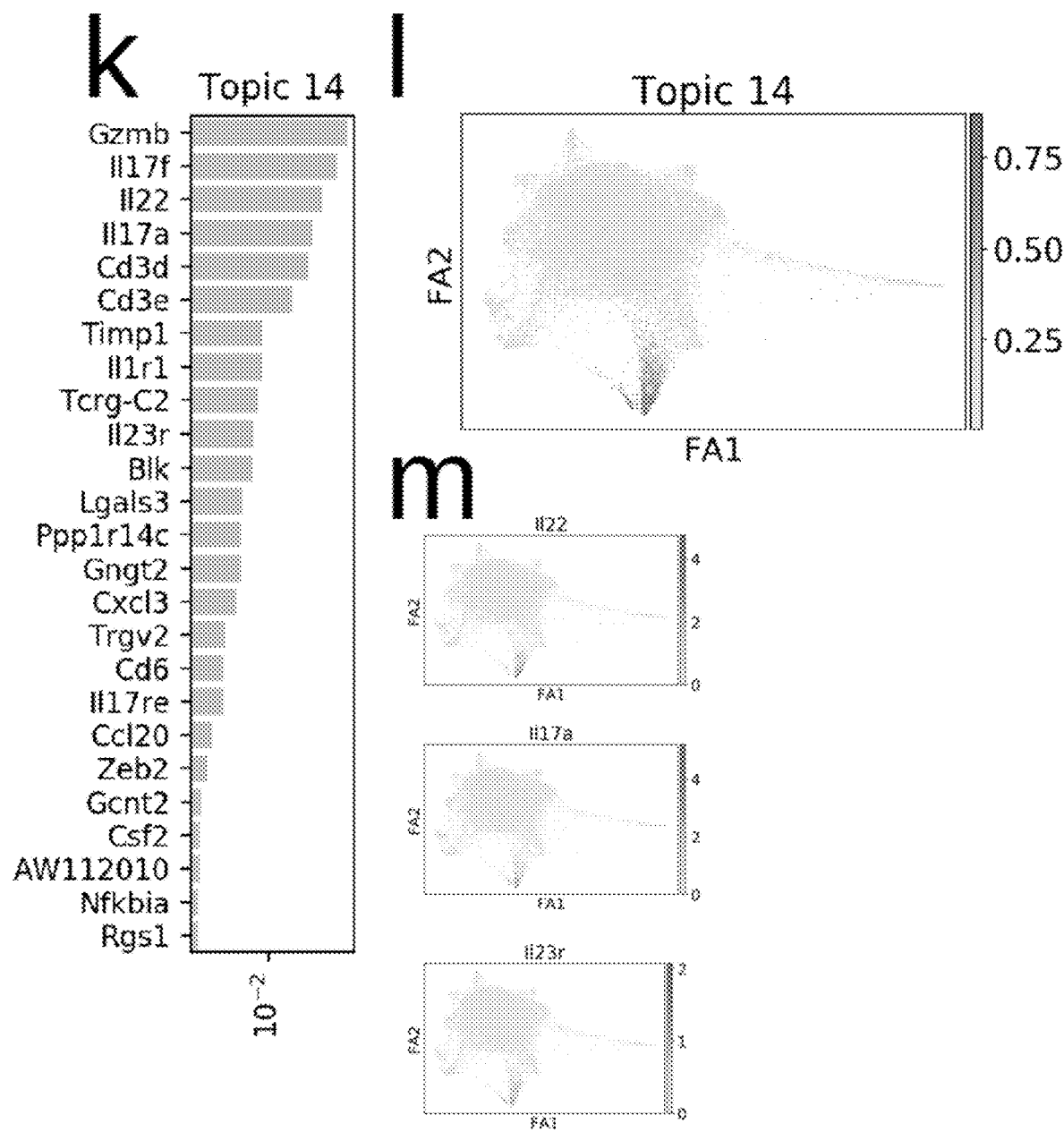
FIG. 9K-M

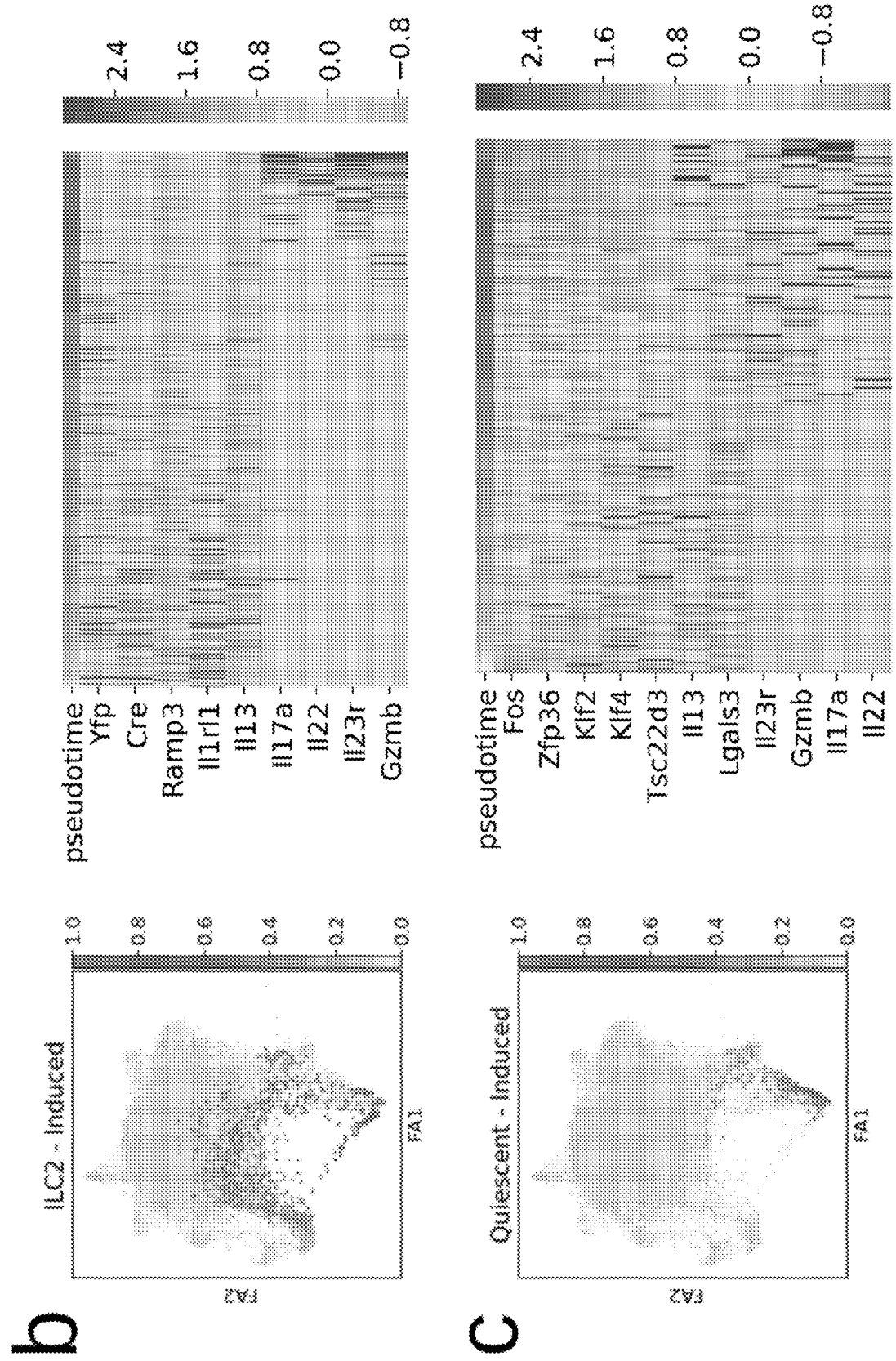
FIG. 10B-C

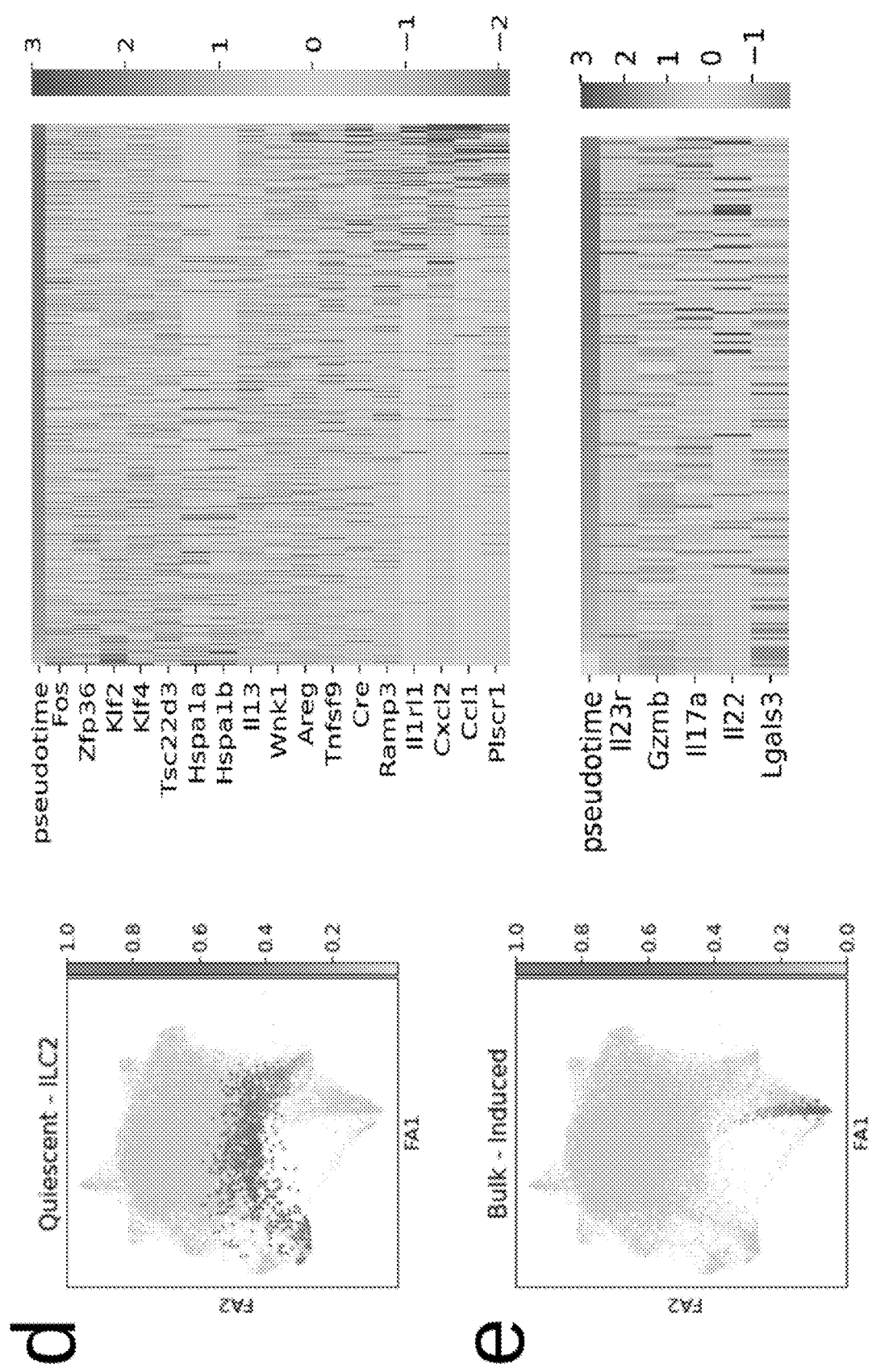
FIG. 10D-E

SEQUENCE LISTING

```
<160> NUMBER OF SEQ ID NOS: 4

<210> SEQ ID NO 1
<211> LENGTH: 288
<212> TYPE: PRT
<213> ORGANISM: Artificial Sequence
<220> FEATURE:
<223> OTHER INFORMATION: Synthetic Peptide

<400> SEQUENCE: 1

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Thr Met Arg Val Ala Val Thr Ala Ala
            115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220
```

```
Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
            245                 250                 255

Thr Gly Gln Leu Leu Lys Ile Ala Lys Arg Gly Gly Val Thr Ala Val
        260                 265                 270

Glu Ala Val His Ala Trp Arg Asn Ala Leu Thr Gly Ala Pro Leu Asn
    275                 280                 285
```

<210> SEQ ID NO 2
<211> LENGTH: 183
<212> TYPE: PRT
<213> ORGANISM: Artificial Sequence
<220> FEATURE:
<223> OTHER INFORMATION: Synthetic Peptide

<400> SEQUENCE: 2

```
Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
50                  55                  60

His Arg Val Ala Asp His Ala Gln Val Arg Val Leu Gly Phe Phe
65                  70                  75                  80

Gln Cys His Ser His Pro Ala Gln Ala Phe Asp Asp Ala Met Thr Gln
            85                  90                  95

Phe Gly Met Ser Arg His Gly Leu Leu Gln Leu Phe Arg Arg Val Gly
        100                 105                 110

Val Thr Glu Leu Glu Ala Arg Ser Gly Thr Leu Pro Pro Ala Ser Gln
    115                 120                 125

Arg Trp Asp Arg Ile Leu Gln Ala Ser Gly Met Lys Arg Ala Lys Pro
130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180
```

<210> SEQ ID NO 3
<211> LENGTH: 37
<212> TYPE: PRT
<213> ORGANISM: Homo sapiens
<220> FEATURE:
<221> NAME/KEY: MISC_FEATURE
<222> LOCATION: (37)..(37)
<223> OTHER INFORMATION: C-terminal NH2 modification

<400> SEQUENCE: 3

```
Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35
```

```
<210> SEQ ID NO 4
<211> LENGTH: 37
<212> TYPE: PRT
<213> ORGANISM: Homo sapiens
<220> FEATURE:
<221> NAME/KEY: MISC_FEATURE
<222> LOCATION: (37)..(37)
<223> OTHER INFORMATION: C-terminal NH2 modification

<400> SEQUENCE: 4

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
            35
```

METHODS AND COMPOSITIONS FOR MODULATING INNATE LYMPHOID CELL PATHOGENIC EFFECTORS

CROSS-REFERENCE TO RELATED APPLICATIONS

This application claims the benefit of U.S. Provisional Application No. 62/758,117, filed Nov. 9, 2018. The entire contents of the above-identified application are hereby fully incorporated herein by reference.

STATEMENT REGARDING FEDERALLY SPONSORED RESEARCH

This invention was made with government support under Grant No. 1552461 awarded by the National Science Foundation. The government has certain rights in the invention.

REFERENCE TO AN ELECTRONIC SEQUENCE LISTING

The contents of the electronic sequence listing (BROD_3930_ST25.txt"; Size is 6,000 bytes and it was created on Nov. 12, 2019) is herein incorporated by reference in its entirety.

TECHNICAL FIELD

The subject matter disclosed herein is generally directed to methods and compositions for modulating inflammation driven by differentiation of quiescent tissue-resident innate lymphoid cells (ILCs) into a spectrum of pathogenic effectors.

BACKGROUND

The factors that balance homeostatic and pathological ILC responses are unclear, and it remains unknown if unique subsets or functional states of ILCs mediate these homeostatic vs. pro-inflammatory effects. Since there are no known markers of such functional states, it is also challenging to distinguish homeostatic from pro-inflammatory ILCs. Single-cell genomics, especially scRNA-seq, can help identify such diversity, even when changes in cell states are continuous across the cells in a population, or are unique to a very small sub-population. Psoriasis pathology is driven by the type 3 cytokines IL-17 and IL-22, but little is understood about the dynamics that initiate alterations in tissue homeostasis.

SUMMARY

In one aspect, the present invention provides for a method of reducing or preventing an innate lymphoid cell (ILC) inflammatory or autoimmune response in a subject in need thereof comprising administering one or more agents capable of: preventing a shift of naïve/quiescent ILCs to type 2 ILCs (ILC2) and/or ILC2s to ILC3-like cells; and/or shifting ILC3-like cells to ILC2s and/or naïve/quiescent ILCs. In certain embodiments, the inflammatory or autoimmune response is skin inflammation, inflammatory bowel disease, rheumatoid arthritis, multiple sclerosis, ankylosing spondylitis, allergy, asthma, or graft-versus-host disease. In certain embodiments, the skin inflammation is psoriasis or atopic dermatitis. In certain embodiments, the ILC3-like cells are characterized by expression of one or more genes or gene products selected from the group consisting of: Srgn, Il13, Il17 and Il22; or Il22, Il17f, Il17a, Gzmb, Ly6a, Timp1, Iltifb, Cxcl2, Gzmc, Gm1045, Cystm1, Cryba4, Ccr5, Il13, Hsd17b10, Dnaja1, Tnfrsf8, Cyb5a, Serpine2 and Srgn. In certain embodiments, the naïve/quiescent ILCs cells are characterized by expression of one or more genes or gene products selected from the group consisting of: Klf2, Klf4, Tsc22d3, Zfp36l2, and Cebpb; or Ubb, Junb, Klf2, Dusp1, Fos, Rgs2, Klf4, Ubc, Zfp36, Zfp36l2, Fosb, Rgcc, Atf3, Jund, Nr4a1, Ier2, Crip1, Csmp1, Pnrc1 and Tsc22d3. In certain embodiments, the one or more agents are capable of preventing or promoting a shift in the expression or activity of one or more genes or gene products selected from the group consisting of Klf2, Tsc22d3, Klf4, Fosb, Zfp36l2, Fos, Zfp36, Pnrc1, Rgs2, Ier2, Nr4a1, Cebpb, Ramp3, Il13, Hilpda, Cd83, Il5, Cxcl2, Bcl2a1b, Pkm, Srgn, Ly6a, Avpi1, Cyb5a, Cd3g, Il22, Batf, Ckb, Cryba4, Lpcat3, Ltb4r1, Pdcd1, Ecm1, Gzmb, Timp1, Ccr5, Il23r, Tnfrsf8, Iltifb, Il17f and Il17a. In certain embodiments, the one or more agents modulate the expression or activity of one or more genes or gene products selected from the group consisting of Klf2, Tsc22d3, Klf4, Fosb, Zfp36l2, Fos, Zfp36, Pnrc1, Rgs2, Ier2, Nr4a1, Cebpb, Ramp3, Il13, Hilpda, Cd83, Il5, Cxcl2, Bcl2a1b, Pkm, Srgn, Ly6a, Avpi1, Cyb5a, Cd3g, Il22, Batf, Ckb, Cryba4, Lpcat3, Ltb4r1, Pdcd1, Ecm1, Gzmb, Timp1, Ccr5, Il23r, Tnfrsf8, Iltifb, Il17f and Il17a (e.g., directly target the genes). In certain embodiments, the one or more agents modulate CGRP signaling. In certain embodiments, the agent is a CGRP signaling agonist. In certain embodiments, the agent is CGRP or functional fragment thereof.

In certain embodiments, the method further comprises detecting in a sample comprising ILCs obtained from the subject naïve/quiescent ILCs, ILC2s and/or ILC3-like cells, wherein if the sample is shifted towards ILC3-like cells the subject is administered one or more agents capable of shifting ILC3-like cells to ILC2s and/or naïve/quiescent ILCs, or wherein if the sample is shifted towards naïve/quiescent ILCs or ILC2s the subject is administered one or more agents capable of preventing a shift of the naïve/quiescent ILCs to type 2 ILCs (ILC2) and/or the ILC2s to ILC3-like cells. In certain embodiments, detecting comprises measuring the expression or activity of one or more genes or gene products selected from the group consisting of: Srgn; or Klf2, Tsc22d3, Klf4, Fosb, Zfp36l2, Fos, Zfp36, Pnrc1, Rgs2, Ier2, Nr4a1, Cebpb, Ramp3, Il13, Hilpda, Cd83, Il5, Cxcl2, Bcl2a1b, Pkm, Srgn, Ly6a, Avpi1, Cyb5a, Cd3g, Il22, Batf, Ckb, Cryba4, Lpcat3, Ltb4r1, Pdcd1, Ecm1, Gzmb, Timp1, Ccr5, Il23r, Tnfrsf8, Iltifb, Il17f and Il17a.

In another aspect, the present invention provides for a method of modulating an innate lymphoid cell (ILC) inflammatory or autoimmune response comprising administering to a population of cells comprising ILCs one or more agents capable of modulating one or more biological programs characterized by Topics 2, 4, 8, 11, 13 or 15 (described further herein). In certain embodiments, the inflammatory or autoimmune response is skin inflammation, inflammatory bowel disease, rheumatoid arthritis, multiple sclerosis, ankylosing spondylitis, allergy, asthma, or graft-versus-host disease. In certain embodiments, the skin inflammation is psoriasis or atopic dermatitis. In certain embodiments, the expression or activity of one or more genes or gene products in a Topic is modulated.

In certain embodiments, the biological program characterized by Topic 11 is modulated, preferably before or after an inflammatory response. In certain embodiments, the expression or activity of one or more genes or gene products selected from the group consisting of Ccl1, Cd74, Cd70, Cd83, Tnfrsf4, Dgat2, Cd82, Il13, Syngr2, Tph1, Cyba, Rel, Ikzf2, Ltb, H2afz, Rplp0, mt-Co2, Ccl22, Timp and Bhlhe40 are modulated.

In certain embodiments, the biological program characterized by Topic 4 is modulated. In certain embodiments, the expression or activity of one or more genes or gene products selected from the group consisting of Tmsb4x, Crip1, S100a4, Lgals1, Actb, S100a6, Pfn1, Sh3bgrl3, Myl6, Serf2, Ly6a, Arhgdib, mt-Atp6, S100a10, Ucp2, S100a13, Rgs1, Cd3g, H3f3b and Ptprcap are modulated.

In certain embodiments, the biological program characterized by Topic 13 is modulated. In certain embodiments, the expression or activity of one or more genes or gene products selected from the group consisting of Cxcl2, Actg1, Hilpda, Pim1, Nr4a1, Il5, Gm20186, Ly6a, Malat1, Satb1, Ode1, Srgn, Il1rl1, H2-Q7, Kdm6b, Cd3e, Cxcl10, Gdd45b, Vps37b and Pdcd1 are modulated.

In certain embodiments, the one or more agents comprise a small molecule, small molecule degrader, genetic modifying agent, antibody, antibody-like protein scaffold, aptamer, protein, or any combination thereof. In certain embodiments, the genetic modifying agent comprises a CRISPR system, RNAi system, a zinc finger nuclease system, a TALE system, or a meganuclease. In certain embodiments, the CRISPR system comprises Cas9, Cas12, or Cas14. In certain embodiments, the CRISPR system comprises a dCas fused or otherwise linked to a nucleotide deaminase. In certain embodiments, the nucleotide deaminase is a cytidine deaminase or an adenosine deaminase. In certain embodiments, the dCas is a dCas9, dCas12, dCas13, or dCas14.

In certain embodiments, the one or more agents are administered topically. In certain embodiments, the treatment is administered by a time release composition.

In another aspect, the present invention provides for a method of detecting an innate lymphoid cell (ILC) inflammatory or autoimmune response comprising detecting a shift of naïve/quiescent ILCs to type 2 ILCs (ILC2) and/or ILC2s to ILC3-like cells. In certain embodiments, detecting an innate lymphoid cell (ILC) inflammatory or autoimmune response comprises detecting in a population of cells comprising ILCs the expression or activity of one or more genes or gene products selected from the group consisting of: Srgn; or Klf2, Tsc22d3, Klf4, Fosb, Zfp36l2, Fos, Zfp36, Pnrc1, Rgs2, Ier2, Nr4a1, Cebpb, Ramp3, Il13, Hilpda, Cd83, Il5, Cxcl2, Bcl2a1b, Pkm, Srgn, Ly6a, Avpi1, Cyb5a, Cd3g, Il22, Batf, Ckb, Cryba4, Lpcat3, Ltb4r1, Pdcd1, Ecm1, Gzmb, Timp1, Ccr5, Il23r, Tnfrsf8, Iltifb, Il17f and Il17a; or one or more biological programs characterized by Topics 2, 4, 8, 11, 13 and/or 15, wherein a shift in the expression or activity as compared to naïve/quiescent ILCs and/or ILC2s indicates an inflammatory response. In certain embodiments, the ILC3-like cells are characterized by expression of one or more genes or gene products selected from the group consisting of Il13, Il17 and Il22. In certain embodiments, the naïve/quiescent ILCs cells are characterized by expression of one or more genes or gene products selected from the group consisting Klf2, Klf4, Tsc22d3, Zfp36l2, and Cebpb. In certain embodiments, detecting naïve/quiescent ILCs, ILC2s and/or ILC3-like cells comprises single cell RNA sequencing, immunohistochemistry, FISH, FACS, Flow-FISH, or a combination thereof.

In another aspect, the present invention provides for a method of screening for ILC modulating agents comprising: contacting a population of ILCs comprising naïve/quiescent ILCs, type 2 ILCs (ILC2) and/or ILC3-like cells with a test agent; and detecting a shift in the ILC population as compared to an untreated population of ILCs. In certain embodiments, detecting a shift in the ILC population comprises detecting a gene signature according to any embodiment herein.

In another aspect, the present invention provides for a kit comprising reagents to detect one or more genes or gene products according to any embodiment herein.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1A. Study overview. From left: Psoriasis mouse model is based on a series of subcutaneous IL-23 injections in WT, Rag1$^{-/-}$ (lack all T and B cells) and Tcrd$^{-/-}$ (lack γδ T cells) mice, phenotypic measurement of skin thickness, and tissue collection and cell isolation for assessment by scRNA-seq, in vitro assays and cytokine expression. FIG. 1B-1C. Tissue resident ILCs are necessary and sufficient for increase in ear skin thickness in response to IL-23 treatment. Increase in skin thickness (mm, y axis) over time (days, x axis) in (b) WT (circle), Rag1$^{-/-}$ (lack all T and B cells, sqaure), Rag2$^{-/-}$ Il2rg$^{-/-}$ mice (also lack ILCs, up triangle), and TCRγδ$^{-/-}$ (lack γδ T cells, down triangle) (n=7 for each group) as well as in (c) Rag2$^{-/-}$ Il2rg$^{-/-}$ mice with (circle) and without (square) intravenously transferred ILCs (n=4 for each group). FIG. 1D. FTY720 blocks white blood cell circulation. Total circulatory white blood cell (WBC) numbers ($10^3$/μl; y axis) in untreated ("Non-TX") and FTY720-treated ("FTY720-TX"), WT and Rag1$^{-/-}$ mice. FIG. 1E. IL23-dependent increases in ear skin thickness does not require circulating cells. Increase in skin thickness (mm, y axis) over time (days, x axis) following IL-23 treatment, in WT (top) and Rag1$^{-/-}$ (bottom) mice, with (square) and without (circle) FTY720-treatment (Methods) (n=3 WT both groups, n=2 Rag1$^{-/-}$ NonTX n=4 Rag1$^{-/-}$ FTY720). FIG. 1F-1G. A secondary challenge with IL-23 increases susceptibility. Increase in skin thickness (mm, y axis) over time (days, x axis; top) or at the end (bottom) of a primary (left bar) or secondary (right bars) challenge with either IL-23 (n=14) or saline control (PBS) (n=5). FIG. 1L-1N. ILCs in untreated mice are epigenetically poised to become ILC3s. Single cell ATAC-seq performed on total skin ILCs sorted from uninduced and IL-23 treated mice (l) show "expression activity" measured by chromatin accessibility at the promoter and the gene body region (from 2 kb upstream of transcription start site to the gene end) of Il5, Il13, Il1rl1 (associated with ILC2) and Il23r, Il22 and Il17a (associated with ILC3) in uninduced and induced sample. (m) Transcription factor motif activity score analysis (highlighting motifs associated with variability in chromatin accessibility between cells) of RORγ (required for ILC3), GATA3 (associated with ILC2) and BATF::JUN (associated with Th17 like cells) (n).

FIG. 2A-FIG. 2E—Topic modeling of skin ILCs highlights repressive, quiescent-like state and multiple, distinct states of activation combined in cells. FIG. 2A. Topic model concept in the context of single cell expression. Topics (top) consist of genes (middle), with distinct weights (gradient, Methods) based on their importance in the topic. Cells (bottom), are scored based on the contribution of each topic in them; a cell can thus have multiple topics. FIG. 2B-2E. Results of LDA on ILCs with 15 topics (Methods). FIG. 2B-2C. Topics reveal complex relationships among clusters. TSNE of cells shaded if they are highly weighted for Topic 11 and light gray otherwise, with shading reflecting cluster membership as in FIG. 1j (b, left), or by expression (log TPX (Methods)) of Cd83, a Topic-11 associated gene (b, right). Analogous plots for Topic 13 (c, left) and its associated gene Srgn (c, right). FIG. 2D-2E Topics with high weights in cells from untreated (Topics 2, 8, and 11) vs. induced (Topics 4, 13, and 15) conditions. (d) For each topic shown are a bar plot of top scoring genes (y axis), ranked by a score (x axis, logarithmic scale) of how well the gene distinguishes this from other topics (Methods); a tSNE (as in FIG. 1i) with cells shaded by the topic's weight in the cells (column j of the cell-by-topic weight matrix θ (θ*,j) for Topic j); and a graph of the empirical cumulative density function (y axis) of topic weights θ*,j (x axis) for cells grouped by treatment or genotype (as in FIG. 1h). (e) Examples of topic-associated genes. Gene expression (y axis, log TPX) as a smoothed function of the topic weight (log θ*,j, x axis), for each of the topics highlighted in d.

FIG. 3A-3B. Distinct topics suggest a dense continuum of states undergoes a dynamic transition during psoriasis induction. Shown is a diffusion map constructed only from cells highly weighted for selected topics (Topics 2, 4, 8, 11, 13, or 15) and the corresponding topic-specific genes (Methods). Plots of DC2 (x axis), DC3 (y axis) and DC1 (z axis), show cells (dots) shaded by either in vivo treatment and genotype (a) or by topic weight (log θ*,j) (b). Light gray arrows (a) indicate an implicit direction of induction. FIG. 3C-3D. A naïve-induced trajectory across DC1 in a focused diffusion map from Topics 8, 13, and 15. DC 1 (x axis), DC2 (y axis), and DC3 (z axis) of a focused diffusion map, with cells shaded as in (a) by in vivo treatment and genotype (c), or as in (b) by topic (d). FIG. 3E. Key genes associated with the trajectory from quiescent-like ILCs to activated ILC2s to ILC3-like cells. Expression (scale, log TPX) of genes (rows) in cells (columns) associated with Topics 8 ("naïve-quiescent"), 13 ("Il5/Cxcl2"), and 15 ("Il22/Il17a"), with cells marked by in vivo condition and genotype (top bar; shaded as in a). Grey scale bars: Topic weights for cells (log θ*,j) (horizontal bars) and genes (log βj,*, where β is the topic-by-gene weight matrix; vertical bars) illustrate mixtures of functional states.

FIG. 4A-FIG. 4I—In vivo validation of the trajectory from quiescent-like ILCs in healthy skin to differentiation of ILC2s to ILC3-like cells during IL-23-induced response. FIG. 4A. ATAC-seq confirms quiescent-like ILCs. Open chromatin peaks (shaded boxes) of ATAC-Seq reads (tracks) from sorted skin ILCs from untreated mice at TSS of key genes (bottom track) responsible for quiescence and repression of type 3 programs. FIG. 4B-4D. ILC2-ILC3 plasticity revealed by IL-5 fate mapping and IL-22BFP and IL-17AGFP reporter mouse. (b) Fate mapping scheme. IL-5 Fate mouse reporter combined with IL-17AGFP and IL-22BFP reporters showing possible outcomes of skin ILC activation, in a scenario with ILC2 to ILC3 differentiation (top) vs. direct ILC3 differentiation (bottom). (c) IL-23 induction increases the number of IL-22- and IL-17A-producing cells, including among cells formerly producing IL-5 ("exIL-5"), especially after secondary challenge. Number of cells (y axis) with each reporter configuration (top label) in IL-23-treated and PBS controls (x axis) in the first (circles) and second (squares) challenge. (d) exIL-5 cells that transdifferentiated to produce IL-22 and IL-17A do not produce IL-5 anymore. FACS plots of the expression of YFP (x axis) and IL22-BFP (y axis, top) or IL17A-GFP (y axis, bottom). FIG. 4E-4F. IL-23 treatment induces IL-13/IL-22 and IL-13/IL-17A double-producing populations and elevates IL-13/IL-22 double production in Rag1 deficient mouse. (e) Levels of IL-13 (x axis) and IL-22 (y axis) measured by intracellular cytokine staining of skin ILCs in wild type (top), Rag1$^{-/-}$ (middle) and Tcrd$^{-/-}$ (bottom) mice. (f) Mean number of cells (y axis) among single producers and co-producers in each mouse genotype (x axis). FIG. 4G. Flow cytometry analysis and scATAC-seq confirms activity of transcription factors identified in quiescent-like ILCs. Intracellular staining indicates downregulation of GILZ encoded by Tsc22d3 in PBS (bottom) compared to IL-23 (top) treated mice measured in sorted skin ILCs. UMAP (Uniform Manifold Approximation and Projection) plot represents transcription factor activity score for KLF4 in untreated and IL-23 treated ILCs. FIG. 4H. ILC2-ILC3 plasticity revealed by IL-5 fate mapping and IL-22$^{BFP}$ and IL-17A$^{GFP}$ reporter mouse. Alternative psoriasis model using imiquimod indicates similar results. IL-17A producing cells increase including exIL-5 cells after treatment. IL-22 production is less induced in imiquimod model over IL-23 injection model. Number of cells (y axis) with each reporter configuration (top label) in untreated mice (squares) and topically treated with imiquimod over 10 days (circles). FIG. 4I. IL-13 fate mapping model confirmed the plasticity of ILC2 and their ability to express ILC3 genes. qRT-PCR gene expression analysis of genes of interest (top labels) in skin ILCs sorted from PBS treated (circles) and IL-23 treated (squares) mice. ILCs sorted as RFP$^+$ are IL-13 fate mapped, RFP$^-$ did not express IL-13 on the protein level. Error bars, SD; *p<0.0332, p<0.021, *p<0.0002, ****p<0.0001 by two-way ANOVA.

FIG. 5A-FIG. 5I—Characterization of skin immune cells to IL-23 induction. FIG. 5A. Increase in ear skin thickness is significantly higher in response to IL-23 treatment than PBS vehicle and is dependent on Rorc. Increase in ear thickness (y axis, mm) following treatment with IL-23 or PBS vehicle in WT (top) or Rorc$^{-/-}$ (bottom) mice. FIG. 5B-5C. Immune cell composition and skin phenotype in different mouse genotypes. (b) Top: Number of cells (y axis) producing IL-22 or IL-17 (x axis) among ILCs (black bars), αβT cells (grey bars) and γδ T cells (white bars) in WT, Tcrd$^{-/-}$ (lack γδ T cells), Rag1$^{-/-}$ (lack all T and B cells), and Rag2$^{-/-}$ Il2rg$^{-/-}$ mice (also lack ILCs) mice. Bottom: Number of total CD45+ (right, y axis) or total ILCs (left, y axis) in WT, Tcrd$^{-/-}$, Rag1$^{-/-}$, and Rag2$^{-/-}$ Il2rg$^{-/-}$ mice (x axis). (c) H&E stains of ear sections in each genotype except Rag2$^{-/-}$ Il2rg$^{-/-}$ mice. Arrows: Acanthosis. FIG. 5D. Expression of type 2 and type 3 related genes in cultured naïve skin ILCs. Shown are relative expression levels (y axis, by qPCR) in ILCs cultured with different cytokines (x axis, table at bottom). FIG. 5E. FTY720 treatment does not impact increased susceptibility to a secondary challenge with IL-23. Skin thickness (y axis, 0.1 mm) over time (x axis, days) in mice following treatment with either IL-23 or IL-23 and FTY720. Bottom bars: period of primary (left bar) and secondary (right bar) challenge. FIG. 5F-5G. ATAC-seq of sorted skin ILCs from untreated mice. Mapped ATAC-seq reads from sorted skin ILCs from untreated mice (top tracks) at different loci (bottom tracks) of interest. Shaded areas: TSS and open chromatin peaks at key TF binding sites, previously identified in CD4+ T cell ChIP-seq data (middle tracks). (f) Open chromatin peaks at TSS of Gata3 (associated with mature ILC2) but not Rorc (ILC3) and Tbx21 (ILC1). (g) Open chromatin peaks at TF binding sites in the Il17a and Il17f promoter, and at the TSS of Il13 but not Il17a, Il17f. FIG. 5H. Cluster B reflects cycling ILCs. tSNE of 27,998 single ILC profiles (dots) shaded by expression level (log TPX) of Stmn1. FIG. 5I. scATAC-seq of sorted skin ILCs from untreated and IL-23 treated mice. TF activity score indicated on UMAP plot of FOS::JUN, STAT3 and TCF7.

FIG. 6A. Selecting the number of topics. Akaike Information Criterion (AIC, circle) and Bayesian Information Criterion (BIC, triangle) value (y axis) for a range of the number K of topics. K=15 (dotted line) is at a point where the AIC curve decreases less steeply and the BIC curve begins to rise. FIG. 6B-6C. Expression of example genes associated with key topics. (b) tSNE of 27,998 single ILC profiles (dots) Shaded by expression level (log TPX (Methods)) for genes in Topics 2, 4, 8, 11, 13, and 15. (c) Gene expression (y axis, log TPX) as a function of the topic weight (log θ*,j, x axis), for each of these topics, for repressive gene Zfp3612 and activation-associated gene Ly6a. FIG. 6D Summary of remaining topics not included in FIG. 2c. For each topic shown are a bar plot of top scoring genes (y axis), ranked by a score (x axis, logarithmic scale) of how well the gene distinguishes this from other topics (Methods); a tSNE (as in b) with cells shaded by the topic's weight in the cells (column j of the cell-by-topic weight matrix θ (θ*,j) for Topic j); and a graph of the empirical cumulative density function (y axis) of topic weights θ*,j (x axis) for cells grouped by treatment or genotype (as in FIG. 2c).

FIG. 7A-7C. Cell selection for diffusion map in FIG. 3a,b. (a) Chosen topic weight thresholds. Empirical cumulative density function (y axis) of topic weights θ*$^j$ (x axis) of cells grouped and shaded by in vivo treatment and genotype. Dotted line: topic weight threshold. (b,c) Cells with high weights in at least one key topic are chosen for the diffusion map. tSNE of 27,998 single ILC profiles (dots), with cells shaded if they are weighted above the corresponding topic threshold from a (b) and chosen for the diffusion map (c, black), if they are highly weighted for Topics 2, 8, 11, 4, 13, or 15, but not for Topics 6 or 7. FIG. 7D-7E. Topics 8, 13, and 15 highlight a potential naïve-induced trajectory across DC1. Plots of DC1 (x axis), DC3 (y axis), and DC4 (z axis) show cells (dots) shaded by either in vivo treatment and genotype (d) or by topic weight (log θ*j) (e). Gray arrows (d) indicate an implicit direction of induction.

FIG. 8A-FIG. 8G—Computational and experimental quality control and data processing. FIG. 8A. IL-23 skin injection model in Il5$^{dTomatoCre}$ (Red5) mouse strain. Increase in skin thickness (mm, y axis) over time (days, x axis) in homozygote Red5/Red5 mouse strain lacking expression of IL-5 cytokine (circle) and Red5/+ mouse (square) shown little difference.

FIG. 8B-8C. Quality control and filters in scRNA-Seq. (b) Minimum and maximum thresholds (dotted line) of log UMI counts (x axis) and log gene counts (y axis) for each condition. Cells (dots) that were filtered out are indicated. (c) Left: Histogram of the % of mitochondrial genes detected across all cells. Right: Box plot of the % of mitochondrial genes of all detected genes in each sample type. Dashed lines: thresholds. FIG. 8D. Distributions for the number of UMI counts in each sample, used to compute log TPX (Methods). FIG. 8E Variable gene selection. For each sample (panel) shown are the coefficient of variation (CV, y axis) as a function of mean counts (x axis) for each gene (dot). Solid black curve: null model (Methods). Genes with sufficiently greater CV than in the null model are indicated, which are retained as variable genes. FIG. 8F-8G. Further confirmation that IL-23 treatment induces IL-13/IL-22 and IL-13/IL-17A double-producing populations and elevates IL-13/IL-22 double production in IL-13 (hCD4)/IL-17A (hNGFR) reporter mice on the WT background (f) and WT and Rag1 deficient mouse after combined IL-23/IL-1β induction measured with cytokine intracellular staining without PMA/Ionomycin ex vivo treatment (g).

FIG. 9A-FIG. 9M—Topic modeling of rapidly responding skin ILCs characterizes continuous mix of distinct transcriptional states, including a quiescent-like state. FIG. 9A. Force-directed layout (FDL) (Methods) of 26877 single-cell profiles (dots) shaded by time point indicates rapid, early transcriptional response to IL-23 stimulation. FIG. 9B-M. Results of LDA model with 17 topics on ILCs (Methods) highlights distinct features of a continuously varying transcriptional landscape. Bar plot shows top genes (y axis) by score (x axis, logarithmic scale) for capacity to distinguish Topic 10 (quiescent-like cells) from other topics (Methods) (b). FDL of cells shaded by weight for Topic 10 (gray if weight is below a minimum threshold) (c), or by normalized expression (Methods) of selected genes associated with Topic 10 (d). Analogous plots for Topic 12 (e-g), 16 (ILC2) (h-j), and 14 (induced) (k-m) are shown.

FIG. 10A-FIG. 10E—Trajectory analysis based on time course data and pseudotime analysis. FIG. 10A. Predicted ancestors of ILC3-like cells by day as inferred by Optimal Transport analysis (Methods) FIG. 10B. Distinct, inferred, IL-23-induced transcriptional trajectories give rise to Il13/Il17a/Il22-expressing ILC3-like cells. A directed diffusion approach (Methods) on scRNA-seq data identifies trajectories visible in the FDL between specific diffusion components. The experimentally validated, sparse ILC2-ILC3 trajectory (FIG. 2). (b) FDL shows cells (dots) shaded by trajectory pseudotime (x axis, Methods). Heatmap shows normalized (z-score capped at 3) gene expression (y axis, Methods) by pseudotime (x axis) for genes associated with the trajectory. FIG. 10C. Analogous plots are shown for a trajectory from quiescent-like to ILC3-like cells FIG. 10D. A continuum between quiescent-like cells and ILC2s FIG. 10E. A continuum from cells in the bulk and ILC3-like cells.

FIG. 11A. Mean normalized expression of genes involved in CGRP regulation by time point in ILC3-like cells selected by topic affinity (Methods) FIG. 11B. Normalized gene expression on FDL of the same genes (all time points).

Figure 1A:
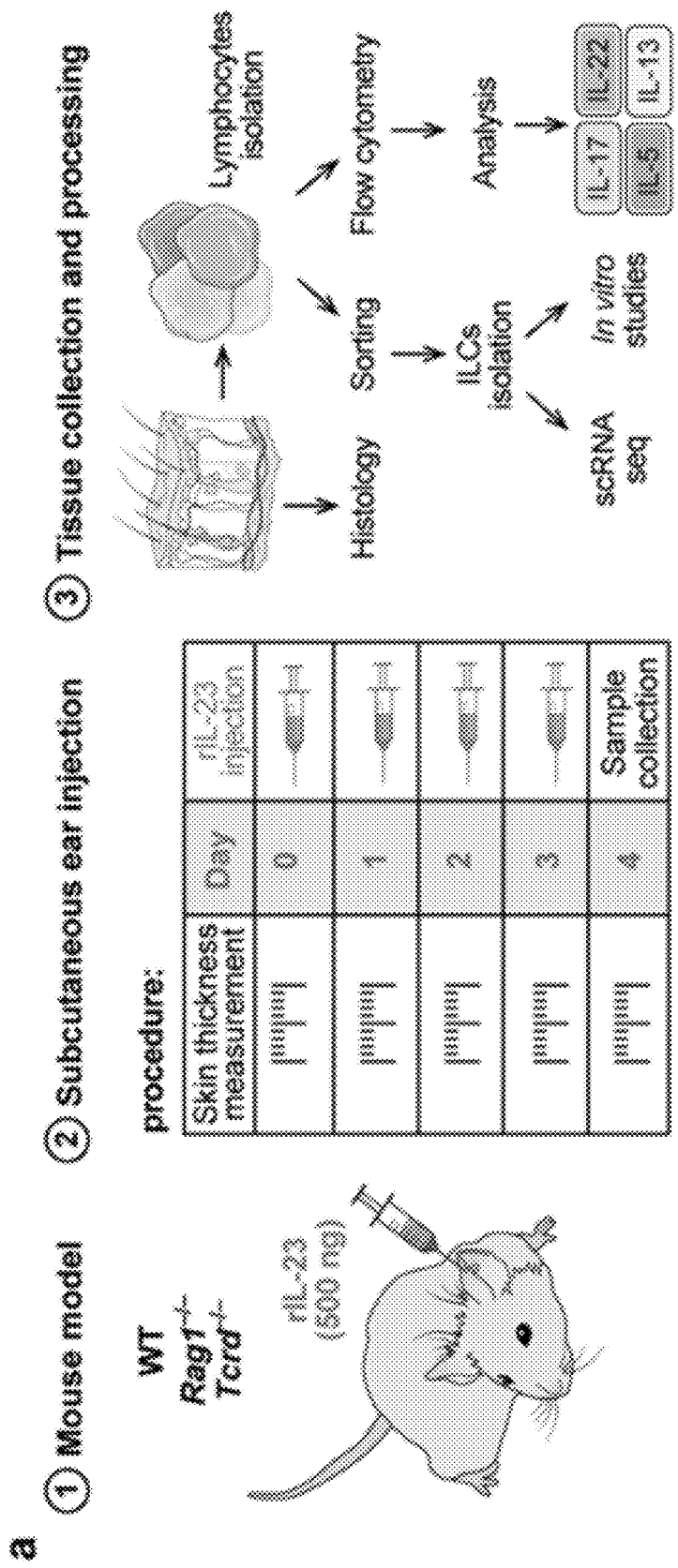
FIG. 1A-FIG. 1N—An epigenetically poised, heterogenous population of tissue-resident ILCs drive initial IL-23-induced pathology.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to PCT/US2019/030911 published as WO2019/213660 and U.S. Provisional Patent Application No. 62/818,404 filed Mar. 14, 2019. Reference is also made to Bielecki, Riesenfeld, Kowalczyk, et al., 2018 Skin inflammation driven by differentiation of quiescent tissue-resident ILCs into a spectrum of pathogenic effectors. bioRxiv 461228. All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods and compositions for modulating and detecting ILC inflammatory and autoimmune responses. Embodiments disclosed herein also provide methods of screening for agents capable of modulating ILC inflammatory and autoimmune responses. Here, Applicants used mouse models, single-cell RNA-seq (scRNA-seq), computational inference and cell lineage mapping to show that psoriasis induction reconfigures the functionality of skin-resident ILCs to initiate disease. Tissue-resident ILCs amplified an initial IL-23 trigger and were sufficient, without circulatory ILCs, to drive pathology, indicating that ILC tissue remodeling initiates psoriasis. Skin ILCs expressed type 2 cytokines IL-5 and IL-13 in steady state, but were epigenetically poised to become ILC3-like cells. ScRNA-seq profiles of ILCs from psoriatic and naïve skin of wild type (WT) and Rag1$^{-/-}$ mice form a dense continuum, consistent with this model of fluid ILC states. Applicants inferred biological "topics" underlying these states and their relative importance in each cell with a generative model of latent Dirichlet allocation, showing that ILCs from untreated skin span a spectrum of states, including a naïve/quiescent-like state and one expressing the Cd74 and Il13 but little Il5. Upon disease induction, this spectrum shifts, giving rise to a greater proportion of classical Il5- and Il13-expressing "ILC2s" and a new, mixed ILC2/ILC3-like subset, expressing Il13, Il17, and Il22. Using these key topics, Applicants related the cells through transitions, revealing a quiescence-ILC2-ILC3s state trajectory. Applicants demonstrated this plasticity in vivo, combining an IL-5 fate mouse with IL-17A and IL-22 reporters, validating the transition of IL-5-producing ILC2s to IL-22- and IL-17A-producing cells during disease initiation. Thus, steady-state skin ILCs are actively repressed and cued for a plastic, type 2 response, which, upon induction, morphs into a type 3 response that drives psoriasis. This suggests a general model where specific immune activities are primed in healthy tissue, dynamically adapt to provocations, and left unchecked, drive pathological remodeling.

Innate Lymphoid Cell Responses

Innate lymphoid cells (ILCs) are a group of innate immune cells that are derived from a common lymphoid progenitor (CLP) and belong to the lymphoid lineage. These cells are defined by absence of antigen specific B or T cell receptors because of the lack of recombination activating gene (RAG). ILCs have varying physiological functions; some functions are analogous to helper T cells, while the group also includes cytotoxic NK cells. Accordingly, they have an important role in protective immunity and the regulation of homeostasis and inflammation, so their dysregulation can lead to immune pathology such as allergy, bronchial asthma and autoimmune disease. In addition, they can regulate adipose function and metabolic homeostasis, in part by eliciting beiging.

ILCs do not express myeloid or dendritic cell markers. ILCs can be divided based on the cytokines that they can produce, and the transcription factors that regulate their development and function.

Group 1 ILCs constitutively express transcription factor T-bet and is able to produce Th1 cytokines (notably IFNγ and TNF) after stimulation with IL-12 or IL-18. ILC1 cells comprise NK cells, CD127low CD103+ intraepithelial ILC1s and CD127high ILC1s.

Group 2 ILCs can produce type 2 cytokines (e.g. IL-4, IL-5, IL-9, IL-13). ILC2s (also termed natural helper cells, nuocytes, or innate helper 2 cells) play the crucial role of secreting type 2 cytokines in response to helminth infection. They have also been implicated in the development of allergic lung inflammation. They express characteristic surface markers and receptors for chemokines, which are involved in distribution of lymphoid cells to specific organ sites. They require IL-7 for their development, which activates two transcription factors (both required by these cells)—RORα and GATA3. After stimulation with Th2 polarizing cytokines (e.g. IL-25, IL-33, TSLP) ILC2s start to produce IL-5, IL-13, IL-9, IL-4. ILC2s are critical for primary responses to local Th2 antigens e.g. helminths and viruses, and that is why ILC2s are abundant in tissues of skin, lungs, livers and gut.

Group 3 ILCs are defined by their capacity to produce cytokines IL-17A and/or IL-22. They are the innate counterpart to Th17 cells, and share the common transcription factor of RORγt. They comprise ILC3s and lymphoid tissue-inducer (LTi) cells. ILC3s are a lymphoid cell population that can produce IL-22 and expresses NKp46 (an NK cell activating receptor). Nevertheless, ILC3s differ from NK cells, as they are dependent on transcription factor RORγt, they lack cytotoxic effectors (perforin, granzymes and death receptors) and they do not produce IFNγ or TNF. They are found mainly in mucosal tissues and particularly in the intestinal tract. Lymphoid tissue inducer (LTi) cells are a subset of ILCs expressing molecules required for the development of lymphoid tissue. They are essential for development of lymphoid organs during embryogenesis and after birth regulate the architecture of lymphoid tissue. Additionally, they have been linked to the maintenance of T cell memory.

ILC immune responses are associated with several diseases. The present invention provides for therapeutic, diagnostic and screening methods applicable to the ILC associated diseases. ILCs affect the initial stages of immunity in response to microbes and participate in immunity, inflammation, and tissue repair. ILCs modulate immunity through resistance to the pathogens and regulation of autoimmune inflammation and metabolic homeostasis. The dysregulation of ILCs can lead to chronic inflammation and autoimmune diseases, including, but not limited to allergies (i.e., asthma, food), inflammation (i.e., inflammatory bowel disease), autoimmunity (i.e., psoriasis, atopic dermatitis, rheumatoid arthritis, multiple sclerosis, and ankylosing spondylitis), and graft-versus-host disease, (see, e.g., Xiong and Turner, Innate lymphoid cells in autoimmunity and chronic inflammatory diseases. Semin Immunopathol. 2018 July; 40(4): 393-406; Mohammadi, et al., The role of innate lymphoid cells in health and disease. J Cell Physiol. 2018 June; 233(6):4512-4529; Ebbo, et al., Innate lymphoid cells: major players in inflammatory diseases. Nat Rev Immunol. 2017 November; 17(11):665-678; Shikhagaie, et al., Innate lymphoid cells in autoimmunity: emerging regulators in rheumatic diseases. Nat Rev Rheumatol. 2017 March; 13(3): 164-173; and Zeng, et al., ILC3 function as a double-edged sword in inflammatory bowel diseases. Cell Death Dis. 2019 April; 10(4): 315). The compositions and methods described further herein are applicable to any of these diseases or conditions.

In certain embodiments, an aberrant ILC response leads to skin inflammation (e.g., psoriasis). ILC3s are critical effector cells in the development of psoriasis (Ebbo et al., 2017). Psoriasis is a long-lasting autoimmune disease characterized by patches of abnormal skin. These skin patches are typically red, dry, itchy, and scaly. On people with darker skin the patches may be purple in color. Psoriasis varies in severity from small, localized patches to complete body coverage. There are five main types of psoriasis: plaque, guttate, inverse, pustular, and erythrodermic. Plaque psoriasis, also known as psoriasis vulgaris, makes up about 90 percent of cases. It typically presents as red patches with white scales on top. Areas of the body most commonly affected are the back of the forearms, shins, navel area, and scalp. Guttate psoriasis has drop-shaped lesions. Pustular psoriasis presents as small non-infectious pus-filled blisters. Inverse psoriasis forms red patches in skin folds. Erythrodermic psoriasis occurs when the rash becomes very widespread, and can develop from any of the other types. Fingernails and toenails are affected in most people with psoriasis at some point in time. This may include pits in the nails or changes in nail color. There currently is no cure for psoriasis; however, various treatments can help control the symptoms. These treatments include steroid creams, vitamin D3 cream, ultraviolet light and immune system suppressing medications, such as methotrexate. Psoriasis is associated with an increased risk of psoriatic arthritis, lymphomas, cardiovascular disease, Crohn's disease and depression. Psoriatic arthritis affects up to 30 percent of individuals with psoriasis.

In certain embodiments, an aberrant ILC response leads to an inflammatory bowel disease (IBD). IBD is composed mainly of Crohn's disease (CD) and ulcerative colitis (UC), and is strongly implicated in the development of intestinal inflammation lesions. Its exact etiology and pathogenesis are still undetermined. Recently accumulating evidence supports that group 3 innate lymphoid cells (ILC3) are responsible for gastrointestinal mucosal homeostasis through moderate generation of IL-22, IL-17, and GM-CSF in the physiological state (Zeng et al., 2019). IBD is a chronic non-specific inflammatory disease without effective drug treatment. At present, medical therapy focuses mainly on usage of anti-inflammatory drugs, such as thiopurines, mercaptopurine, 5-aminosalicylic acid and methotrexate. In general, anti-inflammatory drugs are the first clinical practice in the process of IBD treatment to attenuate intestinal inflammation, but cause various adverse effects (Zeng et al., 2019). Moreover, many patients with IBD do not procure clinical remission with the treatment of mesalazine, immunosuppressant and monoclonal antibodies against the inflammatory cytokine TNF (Zeng et al., 2019). Thus, it is urgent to identify and develop novel drugs with high efficiency and low toxicity.

Gene Signatures and Biological Programs

Applicants have discovered gene signatures or biological programs that shift along a trajectory from naïve/quiescent ILCs to type 2 ILCs (ILC2) and ILC2s to ILC3-like cells. The ILC3-like cells are characterized by expression of Il13, Il17 and Il22. The naïve/quiescent ILCs cells are characterized by expression of Klf2, Klf4, Tsc22d3, Zfp36l2, and Cebpb. The ILC2s are characterized by expression of Il5 and Il13. In certain embodiments, the gene signature that shifts includes Klf2, Tsc22d3, Klf4, Fosb, Zfp36l2, Fos, Zfp36, Pnrc1, Rgs2, Ier2, Nr4a1, Cebpb, Ramp3, Il13, Hilpda, Cd83, Il5, Cxcl2, Bcl2a1b, Pkm, Srgn, Ly6a, Avpi1, Cyb5a, Cd3g, Il22, Batf, Ckb, Cryba4, Lpcat3, Ltb4r1, Pdcd1, Ecm1, Gzmb, Timp1, Ccr5, Il23r, Tnfrsf8, Iltifb, Il17f and Il17a (see, FIG. 3E). The signature shows continuous expression changes from naïve/quiescent ILCs to ILC2s to ILC3-like cells. When the genes are analyzed by a diffusion map the signature is correlated with expression of the gene Srgn, a proteoglycan that is critical for the trafficking and storage of Gzmb (Sutton, V. R. et al. Serglycin determines secretory granule repertoire and regulates natural killer cell and cytotoxic T lymphocyte cytotoxicity. FEBS J (2016) 283, 947-961). In certain embodiments, Srgn is an early indicator of a trajectory toward type 3 activation. In certain embodiments, Srgn is visible before expression of either Gzmb or type 3 cytokines. In certain embodiments, Srgn is used in a diagnostic assay. In certain embodiments, Srgn is used to monitor a treatment. In certain embodiments, Srgn expression increases during a shift toward type 3 activation and expression is monitored over a time course. The time course may be after treatment. In certain embodiments, Srgn is a key regulator of the shift of naïve/quiescent ILCs to ILC2s to ILC3-like cells. In certain embodiments, an agent targeting Srgn is capable of inducing or blocking the shift of naïve/quiescent ILCs to ILC2s to ILC3-like cells. In certain embodiments, genes in the signature decrease in expression during a shift toward type 3 activation (e.g., Klf4).

All gene name symbols refer to the gene as commonly known in the art. The examples described herein that refer to the mouse gene names are to be understood to also encompasses human genes, as well as genes in any other organism (e.g., homologous, orthologous genes). Mouse gene symbols are generally italicized, with only the first letter in upper-case (e.g., Il13). Mouse protein symbols are generally not italicized, and all letters are in upper-case (e.g., IL-13). As used herein mouse gene symbols may be shown with only the first letter in upper-case and not italicized (e.g., Il13). Any reference to the gene symbol is a reference made to the entire gene or variants of the gene. Any reference to the gene symbol is also a reference made to the gene product (e.g., protein). The term, homolog, may apply to the relationship between genes separated by the event of speciation (e.g., ortholog). Orthologs are genes in different species that evolved from a common ancestral gene by speciation. Normally, orthologs retain the same function in the course of evolution. Gene symbols may be those referred to by the HUGO Gene Nomenclature Committee (HGNC) or National Center for Biotechnology Information (NCBI). The signature as described herein may encompass any of the genes described herein.

As used herein a "signature" or "biological program" may encompass any gene or genes, protein or proteins, or epigenetic element(s) whose expression profile or whose occurrence is associated with a specific cell type, subtype, or cell state of a specific cell type or subtype within a population of cells. For ease of discussion, when discussing gene expression, any of gene or genes, protein or proteins, or epigenetic element(s) may be substituted. As used herein, the terms "signature", "biological program", "expression profile", "transcriptional program" or "expression program" may be used interchangeably. It is to be understood that also when referring to proteins (e.g. differentially expressed proteins), such may fall within the definition of "gene" signature.

As used herein the term "biological program" may further refer to a set of genes that share a role in a biological function (e.g., an activation program, cell differentiation program, proliferation program). Biological programs can include a pattern of gene expression that result in a corresponding physiological event or phenotypic trait. Biological programs can include up to several hundred genes that are expressed in a spatially and temporally controlled fashion. Expression of individual genes can be shared between biological programs. Expression of individual genes can be shared among different single cell types; however, expression of a biological program may be cell type specific or temporally specific (e.g., the biological program is expressed in a cell type at a specific time). Multiple biological programs may include the same gene, reflecting the gene's roles in different processes. Expression of a biological program may be regulated by a master switch, such as a nuclear receptor or transcription factor. As used herein, a biological program may be referred to as a "topic." The biological program can be modeled as a distribution over expressed genes.

One method to identify biological programs in cells is non-negative matrix factorization (NMF) (see, e.g., Lee D D and Seung H S, Learning the parts of objects by non-negative matrix factorization, Nature. 1999 Oct. 21; 401 (6755):788-91). As an alternative, a generative model based on latent Dirichlet allocation (LDA) (Blei, D. M., Ng, A. Y., and Jordan, M. I. (2003). Latent Dirichlet allocation. J Mach Learn Res 3, 993-1022), or "topic modeling" may be created. Topic modeling is a statistical data mining approach for discovering the abstract topics that explain the words occurring in a collection of text documents. Originally developed to discover key semantic topics reflected by the words used in a corpus of documents (Dumais, S. T., Furnas, G. W., Landauer, T. K., and Harshman, R. (1990). Indexing by Latent Semantic Analysis. Journal of the American Society for Information Science 41, 391-407), topic modeling can be used to explore gene programs ("topics") in each cell ("document") based on the distribution of genes ("words") expressed in the cell. A gene can belong to multiple programs, and its relative relevance in the topic is reflected by a weight. A cell is then represented as a weighted mixture of topics, where the weights reflect the importance of the corresponding gene program in the cell. Topic modeling using LDA has recently been applied to scRNA-seq data (see, e.g., Bielecki, Riesenfeld, Kowalczyk, et al., 2018 Skin inflammation driven by differentiation of quiescent tissue-resident ILCs into a spectrum of pathogenic effectors. bioRxiv 461228; and duVerle, D. A., Yotsukura, S., Nomura, S., Aburatani, H., and Tsuda, K. (2016). CellTree: an R/bioconductor package to infer the hierarchical structure of cell populations from single-cell RNA-seq data. BMC Bioinformatics 17, 363). Other approaches include word embeddings. Identifying cell programs can recover cell states and bridge differences between cells. Single cell types may span a range of continuous cell states (see, e.g., Shekhar et al., Comprehensive Classification of Retinal Bipolar Neurons by Single-Cell Transcriptomics Cell. 2016 Aug. 25; 166(5): 1308-1323.e30; and Bielecki, et al., 2018).

Applicants identified 15 topics (biological programs) that captured important changes during disease induction, as well as other signals, without obvious signs of overfitting. In certain embodiments, detection or modulation of the biological programs represented by the topics can be used for therapeutic intervention, diagnostic methods, or screening methods described herein. In certain embodiments, the genes in a biological program co-vary in expression and one, or two, or three, or up to five agents can be used to shift the entire biological program. As used herein, the term "co-vary" refers to genes that are upregulated and downregulated together. A correlation between genes refers to genes that co-vary. In preferred embodiments, one or two agents are used to modulate a biological program.

In certain embodiments, Topic 1 includes one or more genes selected from Rpl32, Rps7, Rps15a, Rps4x, Rpl13, Rps18, Rps14, Rps5, Rps16, Rpl17, Rpl13a, Rpl18a, Rps23, Rps19, Rpl23, Rps24, Rps13, Rpl26, Rps3al and Rpl14.

In certain embodiments, Topic 2 includes one or more genes selected from Vps37b, Rps25, Rpl12, Rps24, Bcl2a1d, Tgfb1, Rps23, Rps29, Tesc, Eprs, Rps28, Mest, Pde10a, Amz2, Tmsb4x, Fxd4, Rps15a, Rpl30, Impa2 and Rpl21.

In certain embodiments, Topic 3 includes one or more genes selected from Rpl17, Eef2, Ctla2a, Smpdl3a, Rps11, Itm2b, Rpl18a, Eefla1, Rpl11, Rpl37, Rpl24, Rpl26, Rgs2, Rabac1, Eif3e, Cebpb, Btg1, Rpl9, Gltscr2 and Eif3f.

In certain embodiments, Topic 4 includes one or more genes selected from Tmsb4x, Crip1, S100a4, Lgals1, Actb, S100a6, Pfn1, Sh3bgrl3, Myl6, Serf2, Ly6a, Arhgdib, mt-Atp6, S100a10, Ucp2, S100a13, Rgs1, Cd3g, H3f3b and Ptprcap.

In certain embodiments, Topic 5 includes one or more genes selected from Rps18, Hsp90ab1, Rps27a, S100a11, Actg1, Prdx1, Atp5b, Rplp0, Hspd1, Rps8, Ebna1bp2, H2-D1, Hspa8, Slc25a5, Psma7, Rps2, Mif, Rps6, Cct3 and C1qbp.

In certain embodiments, Topic 6 includes one or more genes selected from mt-Atp6, my-Co3, mt-Co1, mt-Nd1, mt-Co2, mt-Cytb, mt-Nd4, mt-Nd2, mt-Nd3, mt-Nd5, Uba52, S100a6, Gm42418, mt-Atp8, Pxdc1, AY036118, Rplp2, Rpl30, Madd and mt-Nd41.

In certain embodiments, Topic 7 includes one or more genes selected from Fcer1g, Tsc22d1, Xcl1, Klrd1, Tyrobp, Gzmc, Dapk2, Avil, Cd3g, Zmat4, Cd244, Cd7, Gzmf, Fermt2, C1gtnf6, Ifitm2, Kir3d12, Fth1, Adora3 and Pik3r6.

In certain embodiments, Topic 8 includes one or more genes selected from Ubb, Junb, Klf2, Dusp1, Fos, Rgs2, Klf4, Ubc, Zfp36, Zfp36l2, Fosb, Rgcc, Atf3, Jund, Nr4a1, Ier2, Crip1, Csmp1, Pnrc1 and Tsc22d3.

In certain embodiments, Topic 9 includes one or more genes selected from Crip1, Serpinb1a, S100a6, Lmna, Ctla2a, Lgals1, Socs2, Fam107b, Tagln2, Kcnn4, Raph1, S100a10, Plaur, Samsn1, Crip2, Myadm, Dmxl2, Rgcc, Eepd1 and Nudt4.

In certain embodiments, Topic 10 includes one or more genes selected from Fth1, Odc1, Malat1, Ctla2a, Ppia, Ubald2, mt-Co3, Cdkn1a, Tgfb1, Cdk2ap2, Lpxn, Ramp3, Ninj1, Rpl41, Ptprcap, Phlda1, Ftl1, Crem, Blcap and Egln3.

In certain embodiments, Topic 11 includes one or more genes selected from Ccl1, Cd74, Cd70, Cd83, Tnfrsf4, Dgat2, Cd82, Il13, Syngr2, Tph1, Cyba, Rel, Ikzf2, Ltb, H2afz, Rplp0, mt-Co2, Ccl22, Timp and Bhlhe40.

In certain embodiments, Topic 12 includes one or more genes selected from Malat1, Fth1, Srrm2, Prrc2c, Prpf4b, Zcchc7, Ankrd11, Luc712, S100a6, Atrx, Whscl11, Rbm25, Nrd1, Rps29, Pnn, Ddx46, Klf6, Prpf38b, Akap13 and Arglu1.

In certain embodiments, Topic 13 includes one or more genes selected from Cxcl2, Actg1, Hilpda, Pim1, Nr4a1, Il5, Gm20186, Ly6a, Malat1, Satb1, Odc1, Srgn, Il1rl1, H2-Q7, Kdm6b, Cd3e, Cxcl10, Gdd45b, Vps37b and Pdcd1.

In certain embodiments, Topic 14 includes one or more genes selected from Stmn1, 2810417H13Rik, Birc5, Ube2c, Rrm2, Ccnb2, Cdca3, Spc24, Cdca8, Cdk1, Ptma, Mki67, Nusap1, Hist1h2ap, Ccna2, Hmgb2, Cenpm, Tuba1b, Top2a and Tubb5.

In certain embodiments, Topic 15 includes one or more genes selected from Il22, Il17f, Il17a, Gzmb, Ly6a, Timp1, Iltifb, Cxcl2, Gzmc, Gm1045, Cystm1, Cryba4, Ccr5, Il13, Hsdl7b10, Dnaja1, Tnfrsf8, Cyb5a, Serpine2 and Srgn.

Levels of expression or activity or prevalence of genes, gene signatures, or biological programs may be compared between different cells in order to characterize or identify, for instance, signatures specific for cell (sub)populations. Increased or decreased expression or activity or prevalence of signature genes may be compared between different cells in order to characterize or identify, for instance, specific cell (sub)populations. The detection of a signature in single cells may be used to identify and quantitate, for instance, specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a differentiation state of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples, thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory, the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory, the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular pathological condition (e.g. ILC3 inflammatory response), or linked to a particular outcome or progression of the disease, or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular immune cell (sub)population if it is upregulated or only present, detected or detectable in that particular inflammatory cell (sub)population, or alternatively is downregulated or only absent, or undetectable in that particular inflammatory cell (sub)population. In this context, a signature consists of one or more differentially expressed genes/proteins or differential epigenetic elements when comparing different cells or cell (sub)populations, including comparing different ILC cells or ILC cell (sub)populations, as well as comparing disease (sub)populations with non-disease cells or non-disease cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of immune cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least two, at least three, at least four, at least five, at least six, or all genes/proteins and/or epigenetic elements of the signature.

Signatures may be functionally validated as being uniquely associated with a particular immune phenotype. Induction or suppression of a particular signature may consequentially be associated with or causally drive a particular immune phenotype.

Various aspects and embodiments of the invention may involve analyzing gene signatures, protein signatures, and/or other genetic or epigenetic signatures based on single cell analyses (e.g. single cell RNA sequencing) or alternatively based on cell population analyses, as is defined herein elsewhere.

In further aspects, the invention relates to gene signatures, protein signatures, and/or other genetic or epigenetic signatures of particular ILC cell subpopulations, as defined herein elsewhere. The invention hereto also further relates to particular ILC cell subpopulations, which may be identified based on the methods according to the invention as discussed herein; as well as methods to obtain such cell (sub)populations and screening methods to identify agents capable of inducing or suppressing particular ILC cell (sub)populations.

The invention further relates to various uses of the gene signatures, protein signatures, and/or other genetic or epigenetic signatures as defined herein, as well as various uses of the ILC cells or ILC cell (sub)populations as defined herein. Particular advantageous uses include methods for identifying agents capable of inducing or suppressing particular ILC cell (sub)populations based on the gene signature, protein signature, and/or other genetic or epigenetic signature as defined herein. The invention further relates to agents capable of inducing or suppressing particular ILC cell (sub)populations based on the gene signature, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular gene signature, protein signature, and/or other genetic or epigenetic signature may modify overall ILC composition, such as ILC cell composition, such as ILC cell subpopulation composition or distribution, or functionality.

The signature genes of the present invention were discovered by analysis of expression profiles of single-cells within a population of ILC cells, thus allowing the discovery of novel cell subtypes and states that were previously invisible in a population of cells. The presence of subtypes and states may be determined by specific signature genes. The presence of these specific cell types may be determined by applying the signature genes to bulk sequencing data in a patient sample. In certain embodiments, a sample is a conglomeration of many cells that make up a microenvironment, whereby the cells communicate and affect each other in specific ways. As such, specific cell types within this microenvironment may express signature genes specific for this microenvironment. Not being bound by a theory, the signature genes of the present invention may be microenvironment specific. The signature gene may indicate the presence of one particular cell type. In one embodiment, the signature genes of the present invention are applied to bulk sequencing data from a sample obtained from a subject, such that information relating to disease outcome and personalized treatments is determined. In one embodiment, the novel signature genes are used to detect multiple cell states that occur in a subpopulation of ILC cells that are linked to inflammation.

Therapeutic Methods

In certain embodiments, a subject having an inflammatory or autoimmunity disease as described herein is treated with one or more therapeutic agents capable of modulating an ILC immune response (e.g., psoriasis, IBD). In certain embodiments, a subject having, at risk for having or having a history of a type III inflammatory response (e.g., psoriasis, IBD) is treated with an effective amount of a modulating agent (e.g., therapeutic agent). The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

In certain embodiments, an innate lymphoid cell (ILC) inflammatory response is prevented or reduced in a subject in need thereof or in a population of cells by contacting or administering one or more agents capable of preventing a shift of naïve/quiescent ILCs to type 2 ILCs (ILC2) and/or ILC2s to ILC3-like cells; and/or capable of shifting ILC3-like cells to ILC2s and/or naïve/quiescent ILCs. As used herein, the terms "shift" refers to modulation of a system (e.g., ILC cells) in one direction from a reference state. In preferred embodiments, the reference state is a healthy state. In certain embodiments, a healthy state or an unhealthy state is defined by having a certain percentage of one cell type as compared to another (e.g., naïve/quiescent ILCs, ILC2s and/or ILC3-like cells). In certain embodiments, a shift refers to the percentage of cell types within a population of cells. For example, a specific ILC cell type (e.g., ILC3-like) may be 1, 5, 10, 20, 30, 40, 50, 60, 70, 80, 90, 95, 99, or 100% of all of the ILCs in a population of cells. Thus, the ILCs may be shifted when there is a certain percentage of one ILC type. A shift may be represented when a certain cell becomes greater than 50% of the cells in a population. A disease state may also be the reference state and cells are shifted to a healthy state. A shift may also refer to any change of the current cell state (e.g., any change in gene expression along a trajectory of expression in either direction).

As used herein, "treatment" or "treating," or "palliating" or "ameliorating" are used interchangeably. These terms refer to an approach for obtaining beneficial or desired results including, but not limited to, a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein "treating" includes ameliorating, curing, preventing it from becoming worse, slowing the rate of progression, or preventing the disorder from re-occurring (i.e., to prevent a relapse).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

Modulating Agents

In certain embodiments, the present invention provides for one or more therapeutic agents targeting any of the genes, signatures, or cell subtypes identified herein. In certain embodiments, the present invention provides for one or modulating agents capable of shifting ILC balance. In certain embodiments, one or more modulating agents against one of the targets may be used in combination with a treatment already known or used clinically. In certain embodiments, the one or more agents comprise a small molecule, small molecule degrader, genetic modifying agent, antibody, antibody-like protein scaffold, aptamer, protein, or any combination thereof. CGRP In certain embodiments, the agent modulates CGRP signaling. In certain embodiments, the agent is an agonist or antagonist of CGRP receptor activity. The term "agonist of the CGRP receptor" may refer to a compound that binds to a CGRP receptor and activates said CGRP receptor (see, e.g., US20160106813A1).

In one aspect, methods of maintaining or inducing homeostasis of ILCs may comprise administering a CGRP, or functional domain thereof, to a subject in need thereof. In certain example embodiments, a subject in need thereof may be a subject at risk for or having an aberrant ILC inflammatory response. As used herein "maintaining" means that if ILCs are at homeostasis they are maintained in that current state and do not become inflammatory. As used herein "inducing homeostasis" means increasing the amount of homeostatic ILCs or switching inflammatory ILCs to homeostatic ILCs.

The CGRP protein (HUGO Gene Nomenclature Committee ID NO. HGNC:10489) may be any α-CGRP or β-CGRP, their functional variants, functional fragments or any mammalian orthologues thereof. In certain example embodiments, CGRP also includes peptides having undergone post-translational modifications, such as peptides having covalent attachment of glycosyl groups, acetyl groups, phosphate groups, lipid groups, and the like.

The human peptide α-CGRP (UniProtKB/Swiss-Prot ref.: P06881.3) is encoded by the human gene CALCA (NCBI ref: NG_015960.1, NP_001029125.1) and has the sequence: Ala-Cys-Asp-Thr-Ala-Thr-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser- Lys-Ala-Phe-NH2 (SEQ ID NO: 3). In certain example embodiments, the CGRP to be administered is human α-CGRP. In certain example embodiments, the human α-CGRP to be administered is SEQ ID NO: 3 or a functional variant or fragment thereof.

The human peptide s-CGRP (UniProtKB/Swiss-Protref.: P10092.1) is encoded by the human gene CALCB (NCBI ref: NM_000728.4, NP_000719.1), and has the sequence: Ala-Cys-Asn-Thr-Ala-Thr-Cys-Val-Thr-His-Arg-Leu-Ala-Gly-Leu-Leu-Ser-Arg-Ser-Gly-Gly-Met-Val-Lys-Ser-Asn-Phe-Val-Pro-Thr-Asn-Val-Gly-Ser-Lys- Ala-Phe-NH2 (SEQ ID NO: 4). In certain example embodiments, the CGRP to be administered is human β-CGRP. In certain example embodiments, the human α-CGRP to be administered is SEQ ID NO: 4 or a functional variant or fragment thereof.

The gene name Calca or CALCA may refer to the Calcitonin/calcitonin-related polypeptide, alpha gene or polypeptide according to NCBI Reference Sequence accession numbers NM_001033954.3, NM_007587.2, NM_001033952.2, NM_001033953.2 or NM_001741.2. The gene name Ramp1 or RAMP1 may refer to the Receptor (calcitonin) activity modifying protein 1 gene or polypeptide according to NCBI Reference Sequence accession numbers NM_016894.3, NM_001168392.1, or NM_005855.3.

By functional variant or fragment of CGRP, it is herein referred to peptides which peptide sequence differ from the amino acid sequence of wild type CGRP, but that generally retains all the biological activity of CGRP. In certain embodiments, functional variants of CGRP are ligands binding to and activating the CGRP receptor. Functional variants may also include modified peptides, fusion proteins (e.g., fused to another protein, polypeptide or the like, such as an immunoglobulin or a fragment thereof), or peptides having non-natural amino acids. Functional variants may have an extended residence time in body fluids. In certain embodiments, a variant of CGRP has at least 80, 85, 90, 95, 99% of the biological activity of CGRP. In certain embodiments, a variant of α-CGRP has at least 80, 85, 90, 95, 99% of the biological activity of α-CGRP. In certain embodiments, a variant of β-CGRP has at least 80, 85, 90, 95, 99% of the biological activity of β-CGRP. Preferably, a functional variant of α-CGRP has at least 85%, at least 90%, at least 91%, at least 92%, at least 93%, at least 94%, at least 95%, at least 96%, at least 96%, at least 97%, at least 98%, at least 99% sequence identity with α-CGRP. Preferably, a functional variant of β-CGRP has at least 85%, at least 90%, at least 91%, at least 92%, at least 93%, at least 94%, at least 95%, at least 96%, at least 96%, at least 97%, at least 98%, at least 99% sequence identity with β-CGRP.

As used herein, the term "functional fragments" refers to a specific peptide that has a biological activity of interest, which peptide sequence is a part of the peptide sequence of the reference peptide, and that can be of any length, provided the biological activity of peptide of reference is retained by said fragment.

In another aspect, methods of maintaining or inducing homeostasis of intestinal ILC cells may comprise administering a CGRP receptor agonist, or functional domain thereof, to a subject in need thereof. In certain example embodiments, a subject in need thereof may be a subject at risk for or having aberrant activation and expansion of ILC cells.

CGRP receptors have been described as heterodimeric molecules formed of the calcitonin receptor-like receptor (CRLR), linked to RAMP1 (CALCRL). RAMP1 is a transmembrane domain protein of the RAMP family, which further comprises RAMP2 and RAMP3. Several types of receptors are known that can be activated by CGRP: CGRP receptor (formed of CRLR and of RAMP1), $AM_2$ receptor (formed of CRLR and of RAMP3), and $AMY_1$ and $AMY_3$ receptors (formed of the calcitonin receptor and of RAMP1 and RAMP3, respectively). The CGRP receptors can therefore be distinguished from the $AM_2$, $AMY_1$ and $AMY_3$ receptors by the nature of the transmembrane domain of the RAMP family interacting with CRLR.

As used herein, "CGRP receptor", refers to a protein receptor comprising the CRLR protein Ref NCBI: NP_005786.1), bound to the protein Receptor Activity Modifying Protein 1 (RAMP1) (Ref NCBI: NP_005846.1).

Thus, CGRP receptors do not comprise the CRLR protein bound to RAMP2 or RAMP3.

Small Molecules

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking an enzyme active site or activating or blocking a receptor by binding to a ligand binding site).

One type of small molecule applicable to the present invention is a degrader molecule. Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Bondeson and Crews, Targeted Protein Degradation by Small Molecules, Annu Rev Pharmacol Toxicol. 2017 Jan. 6; 57: 107-123; Lai et al., Modular PROTAC Design for the Degradation of Oncogenic BCR-ABL Angew Chem Int Ed Engl. 2016 Jan. 11; 55(2): 807-810; and Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481).

Genetic Modifying Agents

In certain embodiments, the one or more modulating agents may be a genetic modifying agent. The genetic modifying agent may comprise a CRISPR system, a zinc finger nuclease system, a TALEN, a meganuclease or RNAi system.

CRISPR

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence is, in this instance, a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen, Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US2013/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example, reference is made to Platt et al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in, for instance, eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects, the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regard to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words, samples comprising a masking construct may be delivered to a cell, for example, in a suitable delivery vesicle and, if the target is present in the delivery vesicle, the CRISPR effector is activated and a detectable signal generated.

The vector(s) can include a regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-12, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA (s). By simple arithmetic and well established cloning protocols and the teachings in this disclosure, one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector is to express an array of promoter-RNAs separated by cleavable sequences in the intron of a coding sequence or gene; and, in this instance, it is advantageous to use a polymerase II promoter, which can have increased expression and enable the transcription of long RNA in a tissue specific manner. (See, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure, the skilled person can readily make and use vector(s), e.g., a single vector, expressing multiple RNAs or guides under the control or operatively or functionally linked to one or more promoters—especially as to the numbers of RNAs or guides discussed herein, without any undue experimentation.

The guide RNA(s) encoding sequences and/or Cas encoding sequences can be functionally or operatively linked to regulatory element(s) and, hence, the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerate kinase (PGK) promoter, and the EF1α promoter. An advantageous promoter is the promoter U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule", in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex is formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA, may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer. In certain example embodiments, the guide sequence is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20 to 30 nt, advantageously about 20 nt, 23 to 25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15 to 30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such as deamination of nucleotides, are of interest. In alternative embodiments, it is of interest to maintain the limitation of the canonical guide sequence length.

In some embodiments, the sequence of the guide molecule (direct repeat and/or spacer) is selected to reduce the degree of secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example of folding algorithm is the online webserver RNAfold, developed at the Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemical modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl (cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl (cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to, amine, azide, alkyne, thio, dibenzocyclooctyne (DBCO), or Rhodamine. In certain embodiments, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (melΨ), 5-methoxyuridine(5moU), inosine, 7-methyl-guanosine, 2'-O-methyl 3'phosphorothioate (MS), S-constrained ethyl (cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle are chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, allyl, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment, the seed sequence (i.e. the sequence essential critical for recognition and/or hybridization to the sequence at the target locus) of the guide sequence is approximately within the first 10 nucleotides of the guide sequence.

In a particular embodiment, the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments, the direct repeat has a length longer than 16 nts, preferably more than 17 nts, and has more than one stem loop or optimized secondary structures. In particular embodiments, the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence, a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions, include guide termini and regions of the guide molecule that are exposed when complexed with the CRISPR-Cas protein and/or target, for example, the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments, the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments, the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments, these are located at the end of the stem, adjacent to the loop of the stemloop.

In particular embodiments, the susceptibility of the guide molecule to RNases or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecule's sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of an optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA, may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below, and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiments, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may, for example, be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example, using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can, for example, be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in Biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example, targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends a guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm². In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it to act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention, any naturally occurring or engineered derivative of any nuclear receptor, thyroid hormone receptor, retinoic acid receptor, estrogen receptor, estrogen-related receptor, glucocorticoid receptor, progesterone receptor, or androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference to the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 .mu·s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably, the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably, the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably, the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1 V/cm and 20 V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al. (1998) Journal of Magnetic Resonance Imaging Vol. 8, No. 1, pp. 136-142). Another form of focused ultrasound is high intensity focused ultrasound (HIFU) which is reviewed by Moussatov et al. in Ultrasonics (1998) Vol. 36, No. 8, pp. 893-900 and TranHuuHue et al. in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably, the exposure to an ultrasound energy source is at a power density of from about 0.05 to about 100 Wcm-2. Even more preferably, the exposure to an ultrasound energy source is at a power density of from about 1 to about 15 Wcm-2.

Preferably, the exposure to an ultrasound energy source is at a frequency of from about 0.015 to about 10.0 MHz. More preferably, the exposure to an ultrasound energy source is at a frequency of from about 0.02 to about 5.0 MHz or about 6.0 MHz. Most preferably, the ultrasound is applied at a frequency of 3 MHz.

Preferably, the exposure is for periods of from about 10 milliseconds to about 60 minutes. Preferably, the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably, the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as, but not limited to, a lobe of the liver) or whole organ (such as, but not limited to, the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously, there are three or four to thirty or more, e.g., about 10 or more, contiguous base pairs having complementarity to the protected sequence, the guide sequence, or both. It is advantageous that the protected portion does not impede thermodynamics of the CRISPR-Cas system interacting with its target. By providing such an extension, including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprises one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Application 62/432,240 entitled "Novel CRISPR Enzymes and Systems," U.S. Provisional Application 62/471,710 entitled "Novel Type VI CRISPR Orthologs and Systems" filed on Mar. 15, 2017, and U.S. Provisional Application 62/484,786 entitled "Novel Type VI CRISPR Orthologs and Systems," filed on Apr. 12, 2017.

In certain other example embodiments, the CRISPR system effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional Application 62/351,662 filed on Jun. 17, 2016 and U.S. Provisional Application 62/376,377 filed on Aug. 17, 2016. Reference is also made to U.S. Provisional Application 62/351,803 filed on Jun. 17, 2016. Reference is also made to U.S. Provisional Application 62/432,240 entitled "Novel Crispr Enzymes and Systems" filed Dec. 9, 2016. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: *Leptotrichia, Listeria, Corynebacterium, Sutterella, Legionella, Treponema, Filifactor, Eubacterium, Streptococcus, Lactobacillus, Mycoplasma, Bacteroides, Flavivola, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*, or the C2c2 effector protein is an organism selected from the group consisting of: *Leptotrichia shahii, Leptotrichia. wadei, Listeria seeligeri, Clostridium aminophilum, Carnobacterium gallinarum, Paludibacter propionicigenes, Listeria weihenstephanensis*, or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and *Ruminococcus*. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYL1. WYL1 is a single WYL-domain protein associated primarily with *Ruminococcus*.

In other example embodiments, the Type VI RNA-targeting Cas enzyme is Cas13d. In certain embodiments, Cas13d is *Eubacterium siraeum* DSM 15702 (EsCas13d) or *Ruminococcus* sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence.

In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of: Cas effector module, and a guide sequence linked to a direct repeat sequence, wherein the Cas effector module associates one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

A further aspect relates to an isolated cell obtained or obtainable from the methods described herein comprising the composition described herein or progeny of said modified cell, preferably wherein said cell comprises a hypoxanthine or a guanine in replacement of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 August 23 (2013);

Double Nicking by RNA-Guided CRISPR-Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91(2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015).

Nishimasu et al., "Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 September 16.

Cpf1 *Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specificity*, Slaymaker et al., Science 2016 January 1 351 (6268): 84-88 doi: 10.1126/science.aad5227. Epub 2015 December 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. doi: 10.1126/science.aaq0180. Epub 2017 October 25.

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of Streptococcus pneumoniae and Escherichia coli. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multi-nucleotide changes carried on editing templates. The study showed that simultaneous use of two crRNAs enabled multiplex mutagenesis. Furthermore, when the approach was used in combination with recombineering, in S. pneumoniae, nearly 100% of cells that were recovered using the described approach contained the desired mutation, and in E. coli, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR-Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors showed that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of Streptococcus pyogenes Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from Streptococcus pyogenes loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences;

thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al. (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al. (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al. (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein may be designed for use with Cas13, a type II nuclease that does not make use of tracrRNA. Orthologs of Cas13 have been identified in different bacterial species as described herein. Further, type II nucleases with similar properties can be identified using methods described in the art (Shmakov et al. 2015, 60:385-397; Abudayeh et al. 2016, Science, 5; 353(6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung, Nature Biotechnology 32(6): 569-77 (2014), relates to dimeric RNA-guided FokI nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 A1 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-027323 A1 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 A1 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 A1 (U.S. application Ser. No. 14/183,429); US 2015-0184139 A1 (U.S. application Ser. No. 14/324,960); 14/054,414 European Patent Applications EP 2771468 (EP13818570.7), EP 2764103 (EP13824232.6), and EP 2784162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. Provisional Application No. 62/180,709, filed 17 Jun. 2015, PROTECTED GUIDE RNAS (PGRNAS); U.S. Provisional Application No. 62/091,455, filed 12 Dec. 2014, PROTECTED GUIDE RNAS (PGRNAS); U.S. Provisional Application No. 62/096,708, filed 24 Dec. 2014, PROTECTED GUIDE RNAS (PGRNAS); US Provisional Application Nos. 62/091,462, filed 12 Dec. 2014, 62/096,324, filed 23 Dec. 2014, 62/180,681, filed 17 Jun. 2015, and 62/237,496, filed 5 Oct. 2015, DEAD GUIDES FOR CRISPR TRANSCRIPTION FACTORS; US Provisional Application Nos. 62/091,456, filed 12 Dec. 2014 and 62/180,692, filed 17 Jun. 2015, ESCORTED AND FUNCTIONALIZED GUIDES FOR CRISPR-CAS SYSTEMS; U.S. Provisional Application No. 62/091,461, filed 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. Provisional Application No. 62/094,903, filed 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. Provisional Application No. 62/096,761, filed 24 Dec. 2014, ENGINEERING OF SYSTEMS, METHODS AND OPTIMIZED ENZYME AND GUIDE SCAFFOLDS FOR SEQUENCE MANIPULATION; U.S. Provisional Application No. 62/098,059, filed 30 Dec. 2014, 62/181,641, filed 18 Jun. 2015, and 62/181,667, filed 18 Jun. 2015, RNA-TARGETING SYSTEM; U.S. Provisional Application No. 62/096,656, filed 24 Dec. 2014 and 62/181,151, filed 17 Jun. 2015, CRISPR HAVING OR ASSOCIATED WITH DESTABILIZATION DOMAINS; U.S. Provisional Application No. 62/096,697, filed 24 Dec. 2014, CRISPR HAVING OR ASSOCIATED WITH AAV; U.S. Provisional Application 62/098,158, filed 30 Dec. 2014, ENGINEERED CRISPR COMPLEX INSERTIONAL TARGETING SYSTEMS; U.S. Provisional Application No. 62/151,052, filed 22 Apr. 2015, CELLULAR TARGETING FOR EXTRACELLULAR EXOSOMAL REPORTING; U.S. Provisional Application No. 62/054,490, filed 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. Provisional Application No. 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. Provisional Application No. 62/055,484, filed 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. Provisional Application No.

62/087,537, filed 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. Provisional Application No. 62/054,651, filed 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. Provisional Application No. 62/067,886, filed 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; US Provisional Application Nos. 62/054,675, filed 24 Sep. 2014 and 62/181,002, filed 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. Provisional Application 62/054,528, filed 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. Provisional Application No. 62/055,454, filed 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. Provisional Application No. 62/055,460, filed 25 Sep. 2014, MULTIFUNCTIONAL-CRISPR COMPLEXES AND/OR OPTIMIZED ENZYME LINKED FUNCTIONAL-CRISPR COMPLEXES; U.S. Provisional Application No. 62/087,475, filed 4 Dec. 2014 and 62/181,690, filed 18 Jun. 2015, FUNCTIONAL SCREENING WITH OPTIMIZED FUNCTIONAL CRISPR-CAS SYSTEMS; U.S. Provisional Application 62/055,487, filed 25 Sep. 2014, FUNCTIONAL SCREENING WITH OPTIMIZED FUNCTIONAL CRISPR-CAS SYSTEMS; U.S. Provisional Application No. 62/087,546, filed 4 Dec. 2014 and 62/181,687, filed 18 Jun. 2015, MULTIFUNCTIONAL CRISPR COMPLEXES AND/OR OPTIMIZED ENZYME LINKED FUNCTIONAL-CRISPR COMPLEXES; and U.S. Provisional Application 62/098,285, filed 30 Dec. 2014, CRISPR MEDIATED IN VIVO MODELING AND GENETIC SCREENING OF TUMOR GROWTH AND METASTASIS.

Mention is made of US Provisional Application Nos. 62/181,659, filed 18 Jun. 2015 and 62/207,318, filed 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of US Provisional Applications Nos. 62/181,663, filed 18 Jun. 2015 and 62/245,264, filed 22 Oct. 2015, NOVEL CRISPR ENZYMES AND SYSTEMS, US Provisional Application Nos. 62/181,675, filed 18 Jun. 2015, 62/285,349, filed 22 Oct. 2015, 62/296,522, filed 17 Feb. 2016, and 62/320,231, filed 8 Apr. 2016, NOVEL CRISPR ENZYMES AND SYSTEMS, U.S. Provisional Application No. 62/232,067, filed 24 Sep. 2015, U.S. application Ser. No. 14/975,085, filed 18 Dec. 2015, European Application No. 16150428.7, U.S. Provisional Application 62/205,733, filed 16 Aug. 2015, U.S. Provisional Application 62/201,542, filed 5 Aug. 2015, U.S. Provisional Application No. 62/193,507, filed 16 Jul. 2015, and U.S. Provisional Application No. 62/181,739, filed 18 Jun. 2015, each entitled NOVEL CRISPR ENZYMES AND SYSTEMS, and of U.S. Provisional Application No. 62/245,270, filed 22 Oct. 2015, NOVEL CRISPR ENZYMES AND SYSTEMS. Mention is also made of U.S. Provisional Application No. 61/939,256, filed 12 Feb. 2014, and WO 2015/089473 (PCT/US2014/070152), filed 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of International Application No. PCT/US2015/045504, filed 15 Aug. 2015, U.S. Provisional Application No. 62/180,699, filed 17 Jun. 2015, and U.S. Provisional Application No. 62/038,358, filed 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO 2016/161516. WO 2016/161516 describes efficient transduction of polypeptide cargos using synthetic peptides comprising an endosome leakage domain (ELD) operably linked to a cell penetrating domain (CPD), to a histidine-rich domain and a CPD. Similarly, these polypeptides can be used for the delivery of CRISPR-effector based RNPs in eukaryotic cells.

Tale Systems

As disclosed herein, editing can be made by way of the transcription activator-like effector nucleases (TALENs) system. Transcription activator-like effectors (TALEs) can be engineered to bind practically any desired DNA sequence. Exemplary methods of genome editing using the TALEN system can be found, for example, in Cermak T. Doyle EL. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church GM. Arlotta P. Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$—$(X_{12}X_{13})$—$X_{14-33}$ or $_{34}$ or $_{35}$, where the subscript indicates the amino acid position and X represents any amino acid. $X_{12}X_{13}$ indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein, the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region. An exemplary amino acid sequence of a N-terminal capping region is:
MDPIRSRTPSPARELLSGPQPDGVQPTADRGVSP
PAGGPLDGLPARRTMSRTRLPSPPAPSPAFSADS
FSDLLRQFDPSLFNTSLFDSLPPFGAHHTEAATG
EWDEVQSGLRAADAPPPTMRVAVTAARPPRAKPA
PRRRAAQPSDASPAAQVDLRTLGYSQQQQEKIKP
KVRSTVAQHHEALVGHGFTHAHIVALSQHPAALG
TVAVKYQDMIAALPEATHEAIVGVGKQWSGARAL
EALLTVAGELRGPPLQLDTGQLLKIAKRGGVTAV
EAVHAWRNALTGAPLN (SEQ ID NO:1)

An exemplary amino acid sequence of a C-terminal capping region is:
RPALESIVAQLSRPDPALAALTNDHLVALACLG
GRPALDAVKKGLPHAPALIKRTNRRIPERTSHR VAD-
HAQVVRVLGFFQCHSHPAQAFDDAMTQFGM SRHGLLQLFRRVGVTELEARSGTLPPASQRWDR
ILQASGMKRAKPSPTSTQTPDQASLHAFADSLE
RDLDAPSPMHEGDQTRAS (SEQ ID NO:2)

As used herein, the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include, but are not limited to, BLAST or FASTA. Suitable computer programs for carrying out alignments, like the GCG Wisconsin Bestfit package, may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID), SID4X domain or a Krüppel-associated box (KRAB), or fragments of the KRAB domain. In some embodiments, the effector domain is an enhancer of transcription (i.e. an activation domain), such as the VP16, VP64 or p65 activation domain. In some embodiments, the nucleic acid binding is linked, for example, with an effector domain that includes, but is not limited to, a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include, but are not limited to, transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

ZN-Finger Nucleases

Other preferred tools for genome editing for use in the context of this invention include zinc finger systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to FokI cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found, for example, in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary methods for using meganucleases can be found in U.S. Pat. Nos. 8,163,514, 8,133,697, 8,021,867, 8,119,361, 8,119,381, 8,124,369, and 8,129,134, which are specifically incorporated by reference.

RNAi

In certain embodiments, the genetic modifying agent is RNAi (e.g., shRNA). As used herein, "gene silencing" or "gene silenced" in reference to an activity of an RNAi molecule, for example, a siRNA or miRNA, refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA including, but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA, siRNA, can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein and are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al. Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Antibodies

In certain embodiments, the one or more agents is an antibody. The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, VHH and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein or of chemical precursors, is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, IgM antibodies exist in pentameric form, and IgA antibodies exist in monomeric, dimeric or multimeric form.

The term "IgG subclass" refers to the four subclasses of immunoglobulin class IgG-IgG1, IgG2, IgG3, and IgG4 that have been identified in humans and higher mammals by the heavy chains of the immunoglobulins, γ1-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains. The "variable" domains of an antibody light chain are referred to interchangeably as "light chain variable regions", "light chain variable domains", "VL" regions or "VL" domains. The "variable" domains of an antibody heavy chain are referred to interchangeably as "heavy chain constant regions", "heavy chain constant domains", "VH" regions or "VH" domains.

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (1° fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins-harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1 \times 10^7$ $M^{-1}$ (or a dissociation coefficient of 1 µM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant cross reactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the $C_H1$ domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')2 fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques including, but not limited to, specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein can include recombinant peptidomimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Aptamers

In certain embodiments, the one or more agents is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents. Modifications of aptamers may also include modifications at exocyclic amines, substitution of 4-thiouridine, substitution of 5-bromo or 5-iodo-uracil, backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term "phosphorothioate" encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat et al., Nucl. Acid Res. 19:733-738 (1991); Cotten, et al., Nucl. Acid Res. 19:2629-2635 (1991); and Hobbs et al., Biochemistry 12:5138-5145 (1973). Other modifications are known to one of ordinary skill in the art. In certain embodiments, aptamers include aptamers with improved off-rates as described in International Patent Publication No. WO 2009/012418, "Method for generating aptamers with improved off-rates," incorporated herein by reference in its entirety. In certain embodiments, aptamers are chosen from a library of aptamers. Such libraries include, but are not limited to, those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colorado). In certain embodiments, the present invention may utilize any aptamer containing any modification as described herein.

Administration

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, pamoate, valerate, and the like which can be used as a dosage form for modifying the solubility or hydrolysis characteristics or can be used in sustained release or prodrug formulations. It will be understood that, as used herein, references to specific agents also include the pharmaceutically acceptable salts thereof.

Methods of administrating the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules, minicells, polymers, capsules, tablets, and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art as disclosed, for example, in U.S. Pat. Nos. 4,837,028 and 4,737,323. In yet another embodiment, the pharmacological compositions can be delivered in a controlled release system including, but not limited to, a delivery pump (see, for example, Saudek, et al., New Engl. J. Med. 321: 574 (1989)) and a semi-permeable polymeric material (see, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. In certain embodiments, suitable dosage ranges for intravenous administration of the agent are generally about 5-500 micrograms (µg) of active compound per kilogram (Kg) body weight. Suitable dosage ranges for intranasal administration are generally about 0.01 pg/kg body weight to 1 mg/kg body weight. In certain embodiments, a composition containing an agent of the present invention is subcutaneously injected in adult patients with dose ranges of approximately 5 to 5000 µg/human and preferably approximately 5 to 500 µg/human as a single dose. It is desirable to administer this dosage 1 to 3 times daily. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately, the attending physician will decide on the appropriate duration of therapy using compositions of the present invention. Dosage will also vary according to the age, weight and response of the individual patient.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In preferred embodiments, antibodies are used as agonists to depress inflammatory diseases or allergen-induced asthmatic responses. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In certain embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa.

In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of antibodies to the respiratory tract mucosa may be a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like; d) peptides and proteins, such as aspartame, human serum albumin, gelatin, and the like; e) alditols, such mannitol, xylitol, and the like; and f) polycationic polymers, such as chitosan or a chitosan salt or derivative.

For dermal application, the antibodies of the present invention may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabens, such as methyl, ethyl, propyl, p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and benzylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives, wool fats, wool alcohols, sorbitan esters, monoglycerides, fatty alcohols, fatty acid esters (e.g. triglycerides of fatty acids), and mixtures thereof.

Examples of suspending agents are, e.g., celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Examples of gel bases, viscosity-increasing agents or components which are able to take up exudate from a wound are liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carrageenan, hyaluronates (e.g. hyaluronate gel optionally containing sodium chloride), and alginates including propylene glycol alginate.

Examples of ointment bases are, e.g., beeswax, paraffin, cetanol, cetyl palmitate, vegetable oils, sorbitan esters of fatty acids (Span), polyethylene glycols, and condensation products between sorbitan esters of fatty acids and ethylene oxide, e.g., polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmellose, sodium carmellose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetearyl glucoside, collagen, carrageenan, hyaluronates and alginates and chitosans.

The dose of antibody required in humans to be effective in the treatment or prevention of allergic inflammation differs with the type and severity of the allergic condition to be treated, the type of allergen, the age and condition of the patient, etc. Typical doses of antibody to be administered are in the range of 1 µg to 1 g, preferably 1-1000 µg, more preferably 2-500 µg, even more preferably 5-50 µg, most preferably 10-20 µg per unit dosage form. In certain embodiments, infusion of antibodies of the present invention may range from 10-500 mg/m$^2$.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

In another aspect, provided is a pharmaceutical pack or kit, comprising one or more containers filled with one or more of the ingredients of the pharmaceutical compositions.

Diagnostic Methods

In certain embodiments, one or more biomarkers is detected in a subject having, at risk for, or having a history of, an inflammatory or autoimmune disease as described herein (e.g., psoriasis, IBD). The invention provides biomarkers (e.g., biological programs, signature genes) for the identification, diagnosis, prognosis and manipulation of disease phenotypes (e.g., immune state), for use in a variety of diagnostic and/or therapeutic indications. Biomarkers in the context of the present invention encompasses, without limitation nucleic acids, proteins, reaction products, and metabolites, together with their polymorphisms, mutations, variants, modifications, subunits, fragments, and other analytes or sample-derived measures. In certain embodiments, biomarkers include the signature genes or signature gene products, and/or cells as described herein.

In certain embodiments, the invention provides uses of the biomarkers for predicting risk for a certain phenotype (e.g., ILC immune response). In certain embodiments, the invention provides uses of the biomarkers for selecting a treatment. In certain embodiments, a subject having a disease can be classified based on severity of the disease.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The biomarkers of the present invention are useful in methods of identifying specific patient populations based on a detected level of expression, activity and/or function of one or more biomarkers. These biomarkers are also useful in monitoring subjects undergoing treatments and therapies for suitable or aberrant response(s) to determine efficaciousness of the treatment or therapy and for selecting or modifying therapies and treatments that would be efficacious in treating, delaying the progression of or otherwise ameliorating a symptom. The biomarkers provided herein are useful for selecting a group of patients at a specific state of a disease with accuracy that facilitates selection of treatments.

The term "monitoring" generally refers to the follow-up of a disease or a condition in a subject for any changes which may occur over time.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-A-vis a control subject or subject population.

Hence, the methods may rely on comparing the quantity of biomarkers, or gene or gene product signatures measured in samples from patients with reference values, wherein said reference values represent known predictions, diagnoses and/or prognoses of diseases or conditions as taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values can represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favorable or unfavorable prognoses for such disease or condition.

Such comparison may generally include any means to determine the presence or absence of at least one difference and optionally of the size of such difference between values being compared. A comparison may include a visual inspection, an arithmetical or statistical comparison of measurements. Such statistical comparisons include, but are not limited to, applying a rule.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or 1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

Detection of Biomarkers

In one embodiment, one or more of the signature genes are detected by immunofluorescence, immunohistochemistry (IHC), fluorescence activated cell sorting (FACS), mass spectrometry (MS), mass cytometry (CyTOF), RNA-seq, single cell RNA-seq (described further herein), quantitative RT-PCR, single cell qPCR, RNA-FISH, MERFISH (multiplex (in situ) RNA FISH) and/or by in situ hybridization. Detection may comprise primers and/or probes or fluorescently bar-coded oligonucleotide probes for hybridization to RNA (see e.g., Geiss G K, et al., Direct multiplexed measurement of gene expression with color-coded probe pairs. Nat Biotechnol. 2008 March; 26(3):317-25). Other methods including absorbance assays and colorimetric assays are known in the art and may be used herein.

In one embodiment, cells are stained for specific signature genes. In one embodiment, the cells are fixed. In another embodiment, the cells are formalin fixed and paraffin embedded. In certain embodiments, the cell types may be quantitated in a tissue section and the number of cells indicates an outcome and personalized treatment. In certain embodiments, an immune response is diagnosed, prognosed, or monitored. For example, a tissue sample may be obtained and analyzed for specific cell markers (IHC) or specific transcripts (e.g., RNA-FISH). In one embodiment, a tissue sample is stained for cell subtype specific signature genes. Not being bound by a theory, the presence of the immune cell subtypes indicate outcome and personalized treatments.

The present invention also includes a kit with one or more detection reagents for the one or more biomarkers.

Sequencing

In certain embodiments, sequencing is used to identify the expression of signature genes or biological programs in single cells. In certain embodiments, sequencing comprises high-throughput (formerly "next-generation") technologies to generate sequencing reads. Methods for constructing sequencing libraries are known in the art (see, e.g., Head et al., Library construction for next-generation sequencing: Overviews and challenges. Biotechniques. 2014; 56(2): 61-77). A "library" or "fragment library" may be a collection of nucleic acid molecules derived from one or more nucleic acid samples, in which fragments of nucleic acid have been modified, generally by incorporating terminal adapter sequences comprising one or more primer binding sites and identifiable sequence tags. In certain embodiments, the library members (e.g., cDNA) may include sequencing adaptors that are compatible with use in, e.g., Illumina's reversible terminator method, long read nanopore sequencing, Roche's pyrosequencing method (454), Life Technologies' sequencing by ligation (the SOLiD platform) or Life Technologies' Ion Torrent platform. Examples of such methods are described in the following references: Margulies et al. (Nature 2005 437: 376-80); Schneider and Dekker (Nat Biotechnol. 2012 Apr. 10; 30(4):326-8); Ronaghi et al. (Analytical Biochemistry 1996 242: 84-9); Shendure et al. (Science 2005 309: 1728-32); Imelfort et al (Brief Bioinform. 2009 10:609-18); Fox et al. (Methods Mol. Biol. 2009; 553:79-108); Appleby et al. (Methods Mol. Biol. 2009; 513:19-39); and Morozova et al. (Genomics. 2008 92:255-64), which are incorporated by reference for the general descriptions of the methods and the particular steps of the methods, including all starting products, reagents, and final products for each of the steps.

In certain embodiments, the invention involves detection of signature genes or biological programs by single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p 666-673, 2012).

In certain embodiments, the present invention involves single cell RNA sequencing (scRNA-seq). In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; Gierahn et al., "Seq-Well: portable, low-cost RNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In certain embodiments, a sample is assayed by ATAC-seq to determine open chromatin at a signature gene. The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature Methods 2013; 10 (12): 1213-1218; US20160208323A1; US20160060691A1; WO2017156336A1; J. D. Buenrostro et al., Single-cell chromatin accessibility reveals principles of regulatory variation. Nature 523, 486-490 (2015); and Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237):910-4. doi: 10.1126/science.aab1601. Epub 2015 May 7).

In certain embodiments, dimension reduction is used to cluster single cells based on differentially expressed genes. In certain embodiments, the dimension reduction technique may be, but is not limited to, Uniform Manifold Approximation and Projection (UMAP) or t-SNE (see, e.g., Becht et al., Evaluation of UMAP as an alternative to t-SNE for single-cell data, bioRxiv 298430; doi.org/10.1101/298430; and Becht et al., 2019, Dimensionality reduction for visualizing single-cell data using UMAP, Nature Biotechnology volume 37, pages 38-44).

MS Methods

Biomarker detection may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')$_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

Immunoassays

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Hybridization Assays

Hybridization assays may be used to detect biomarkers. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5xSSC plus 0.2% SDS at 65° C. for 4 hours followed by washes at 25° C. in low stringency wash buffer (1xSSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B. V. (1993) and Kricka, "Nonisotopic DNA Probe Techniques", Academic Press, San Diego, Calif. (1992).

In certain embodiments, a subject can be categorized based on signature genes or gene programs expressed by a tissue sample obtained from the subject. In certain embodiments, the tissue sample is analyzed by bulk sequencing. In certain embodiments, subtypes can be determined by determining the percentage of specific cell subtypes expressing the identified biomarkers in the sample that contribute to the phenotype. In certain embodiments, gene expression associated with the cells are determined from bulk sequencing reads by deconvolution of the sample. For example, deconvoluting bulk gene expression data can include defining the relative frequency of a set of cell types in a sample from the bulk gene expression data using cell type specific gene expression.

Screening for Modulating Agents

In certain embodiments, the invention provides for screening of therapeutic agents capable of modulating gene signatures and/or biological programs. In certain embodiments, agents capable of blocking ILCs from shifting or capable of inducing a shift are screened. In certain embodiments, the method comprises: a) applying a candidate agent to a cell population comprising ILCs; b) detecting modulation of one or more phenotypic aspects of the cell population by the candidate agent, thereby identifying the agent. The phenotypic aspects of the cell population that is modulated may be a gene signature or biological program specific to a cell type or cell phenotype or phenotype specific to a population of cells (e.g., an immune phenotype). In certain embodiments, steps can include administering candidate modulating agents to cells, detecting identified cell (sub) populations for changes in signatures, or identifying relative changes in cell (sub) populations which may comprise detecting relative abundance of particular gene signatures. The phenotype may be a change in secretion of cytokines associated with ILCs. In certain embodiments, candidate agents are screened in vivo models (e.g., mouse models as described herein). In certain embodiments, inflammation in a model is detected.

The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof, as described herein.

The methods of phenotypic analysis can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

Aspects of the present disclosure relate to the correlation of an agent with the spatial proximity and/or epigenetic profile of the nucleic acids in a sample of cells. In some embodiments, the disclosed methods can be used to screen chemical libraries for agents that modulate chromatin architecture epigenetic profiles, and/or relationships thereof.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, agents capable of shifting the signatures are screened. In certain embodiments, master regulators of the signature are identified (e.g., transcription factors). In certain embodiments, agonists or antagonists of cell receptors expressed on the ILCs are screened. The signature of the present may be used to screen for drugs that modulate or shift the signature in ILCs, ILC cell lines, or animal models. In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures or biological programs of the present invention may be used to screen for drugs that reduce the signature or biological program in cells as described herein. The signature or biological program may be used for GE-HTS. In certain embodiments, pharmacological screens may be used to identify drugs that are selectively toxic to cells having a signature.

In certain embodiments, Cmap is used to screen for in silico for agents capable of shifting the signature. The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science. 1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature or biological program of the present invention in silico.

Further embodiments are illustrated in the following Examples which are given for illustrative purposes only and are not intended to limit the scope of the invention.

EXAMPLES

Example 1—Skin Inflammation Driven by Differentiation of Quiescent Tissue-Resident ILCs into a Spectrum of Pathogenic Effectors To determine which cells are key to initiate psoriatic disease, Applicants studied a subcutaneous IL-23 injection model, which leads to increased skin thickness after five days of daily injections (FIG. 1a, FIG. 5a). First, Applicants assessed the role of different immune cell types in this model (FIG. 1b, FIG. 5b,c). Consistent with previous results, the Rag2$^{-/-}$ Il2rg$^{-/-}$ double mutant, which lacks all lymphocytes, did not show any increase in ear thickness, whereas Rag1$^{-/-}$ mice, which have intact ILCs, showed significant increase in skin thickness over the treatment course. This is also consistent with an increased number of human ILC3s recently observed in psoriatic patients[3,4]. Moreover, while γδ T cells have been implicated in a longer treatment course[2,5], analyzing Tcrd$^{-/-}$ mice, which lack only γδ T cells, Applicants found no evidence that they contribute to disease initiation (FIG. 1b). Next, to further confirm the role of ILCs in disease initiation, Applicants adoptively transferred sorted skin ILCs from untreated WT mice into Rag2$^{-/-}$ Il2rg$^{-/-}$ mice, and observed significant skin thickening in treated versus untreated recipient mice (FIG. 1c). Finally, Applicants assessed the contributions of circulatory versus tissue-resident lymphocytes in the psoriasis model, because recent studies of inflammation in several peripheral tissues suggested different involvement of circulatory and tissue resisdent ILCs[6-10]. Applicants compared disease phenotype between control mice and those treated with FTY720, which blocks signaling from the S1P1 receptor, preventing egress of T cells from secondary lymphoid tissues and limiting trafficking of induced ILC2s[7,11]. FTY720-treated mice had the expected reduction of circulating total white blood cells, but showed no difference in psoriasis phenotype induction upon IL-23 administration compared with untreated controls, in both WT or Rag1$^{-/-}$ (lacking T and B cells) mice (FIG. 1d,e). Thus, in contrast to a model of lung inflammation, in psoriasis, tissue-resident ILCs are sufficient to drive disease pathology and are critical for amplifying the response to IL-23.

Figure 5D:
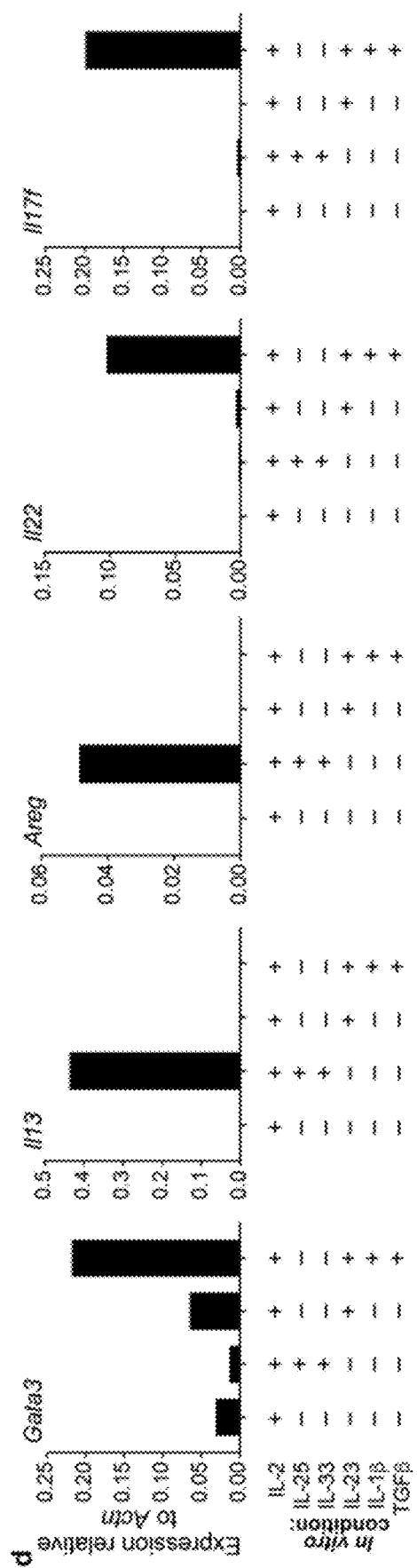
Figure 5I:
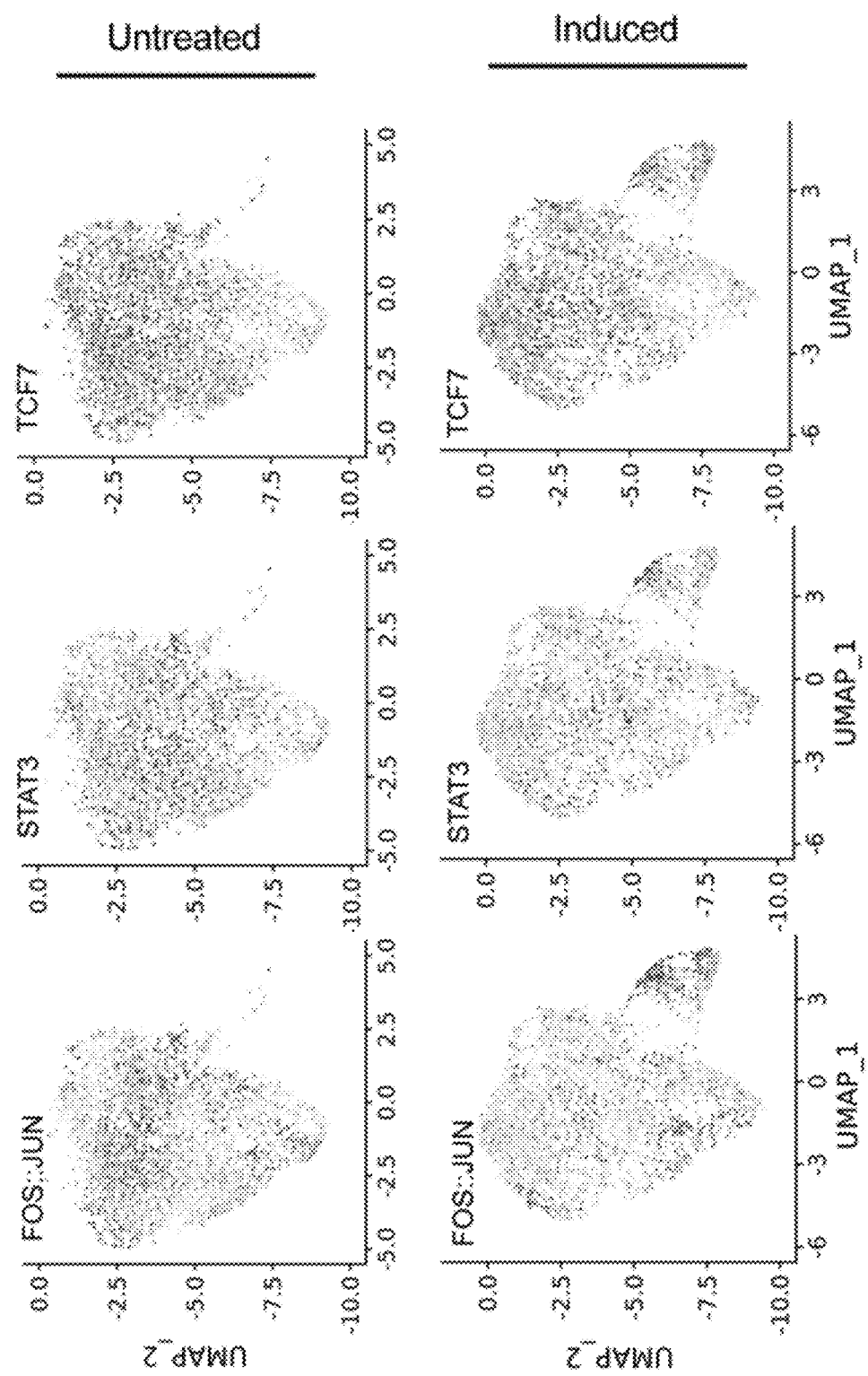

Applicants observed that skin ILCs expressed the type 2 cytokines IL-5 and IL-13 in steady state, but showed potential to plastically to assume ILC3-like states. Consistent with prior reports that naïve mouse skin ILCs are comprised almost exclusively of GATA3$^+$ ILC2s[12], total ILCs isolated from healthy mouse skin and treated with the type 2 alarmin cytokines IL-25 and L-33 had a strong type 2 activation, as indicated by expression of Areg and Il13 (FIG. 5d). However, total ILCs treated with IL-23 and IL-1s instead strongly expressed Il22 and Il17a (FIG. 5d), suggesting that tissue-resident skin ILCs may have potential for type 2-3 plasticity. Such plasticity has been previously reported in IL-17A co-expressing "inflammatory ILC2s" in the lung[13,14], similar to reported type 3-1 plasticity in gut and tonsil ILCs and type 2-1 plasticity in blood ILCs[5-20]. Moreover, while inflammation and skin thickness reverted to near-baseline levels within 10 days after the initial IL-23 injection (FIG. 1f), this initial challenge promoted a stronger type 3 response upon re-challenge. Specifically, mice showed a significantly more severe phenotype after a second series of IL-23 injections, compared to their initial response (FIG. 1f,g). This was also observed in mice treated with FTY720 during the primary injection (FIG. 5e), suggesting that the plastic psoriatic response is not due to ILC recruitment.

Figure 1H:
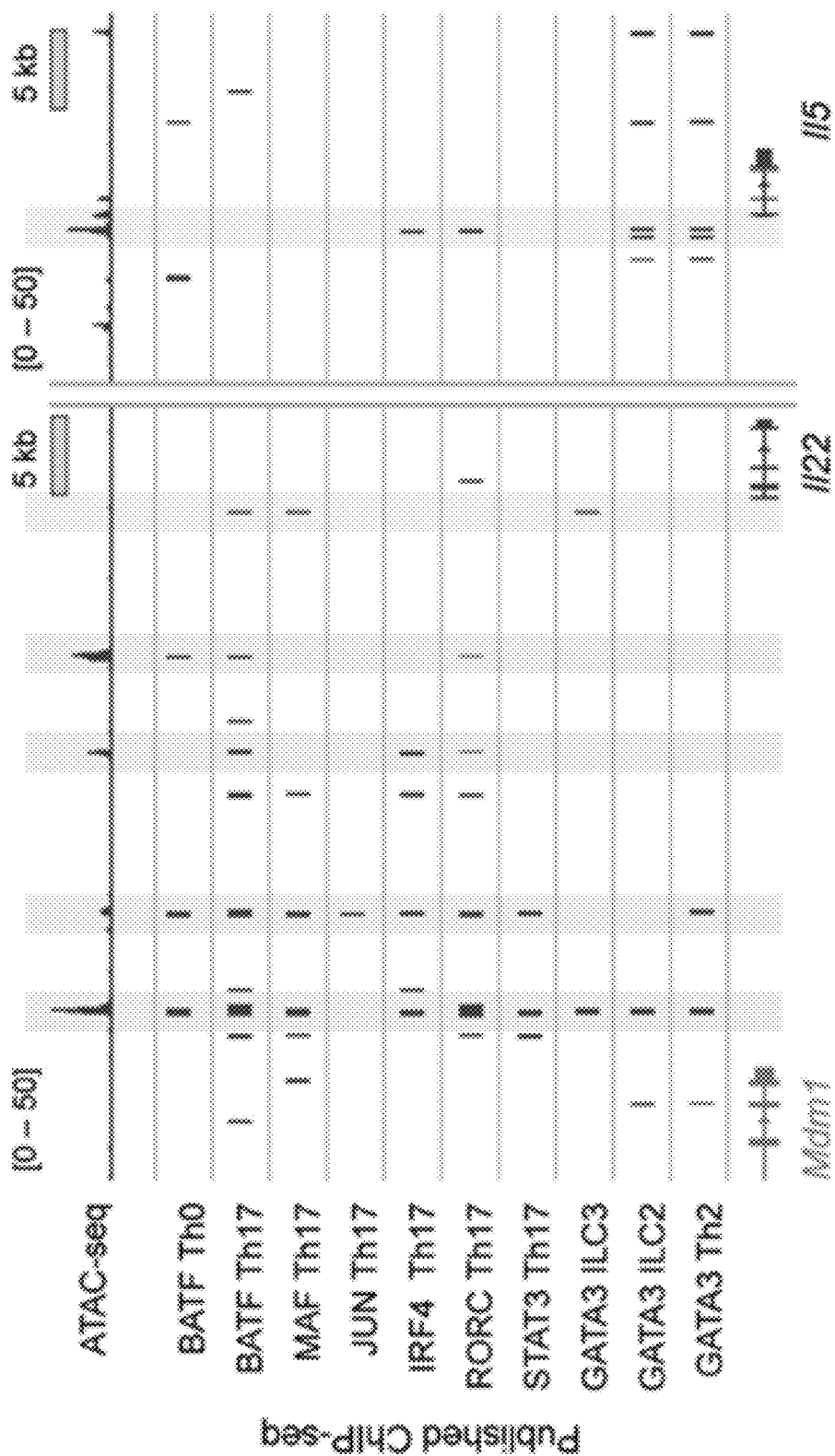
FIG. 1H. ILCs in untreated mice are epigenetically poised to become ILC3s. Mapped ATAC-seq reads (top track) at the Il22 (left) and Il5 (right) promoter loci (bottom track) from sorted skin ILCs from untreated mice, show open chromatin peaks (bars) at key TF binding sites, previously identified in CD4+ T cell ChIP-seq data (middle tracks), and at the TSS of Il5 but not Il22.

Applicants hypothesized that this plasticity may be encoded epigenetically. To test this hypothesis, Applicants profiled sorted total skin ILC populations from naïve mice by ATAC-seq. Applicants observed the expected open chromatin signature at the TSS of Gata3, Il5 and Il13 and not at the TSS of Tbx21 or Rorc, which encode T-bet and Rorγt, the hallmark transcription factors (TFs) of ILC1s and ILC3s, respectively, or at the TSS of Il22, Il17a, or Il17f (FIG. 5f,g). In support of the hypothesis, Applicants also observed strong ATAC-seq peaks at at promoters of some type 3 genes in TFs binding sites, such as Batf, Maf, and Irf[21-23] (FIG. 1h, FIG. 5g), which are known to regulate Th17 cells. (See, also, FIG. 1k-n). Taken together, the data support a model where IL-23 induces psoriasis by remodeling a heterogeneous, tissue-resident ILC population with unexpected potential for differentiation, rather than by recruiting circulating ILCs to replace a homogenous, terminally differentiated skin-resident ILC2 population.

Figure 1I:
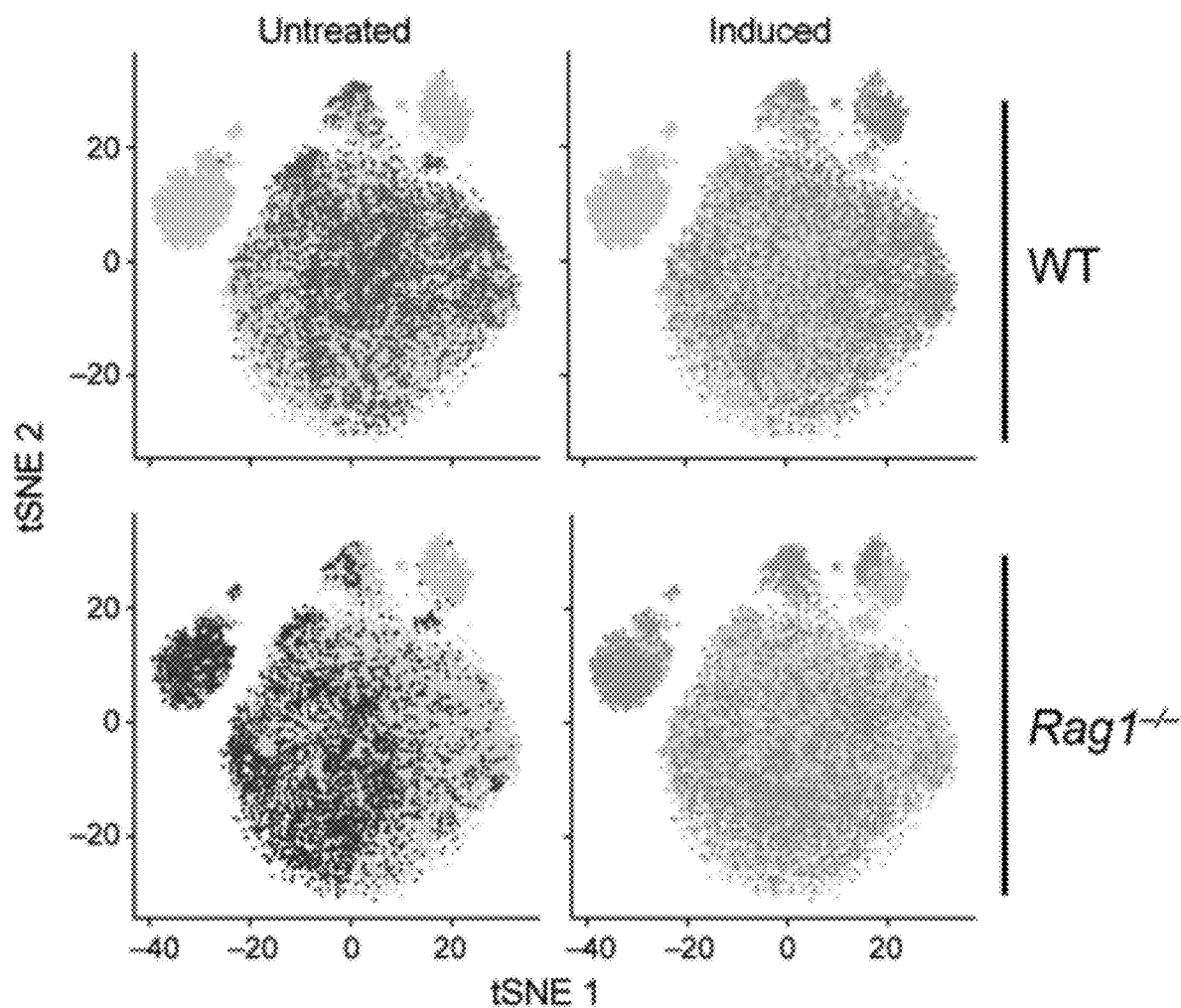
FIG. 1I-1J. ILC heterogeneity highlighted by scRNA-seq. t-Distributed stochastic neighbor embedding (tSNE) of 27,998 single cell (dots) profiles (Methods) shaded by either in vivo treatment and genotype (i), or by cluster assignment or expression of key genes (log TPX (Methods)) (j). Annotated clusters (j, top left) include a Rag1$^{-/-}$ specific cluster (A) expressing the ILC1-associated gene Klrd1, cycling cells (B), an Il22-high cluster co-expressing Il13 (C), and a heterogeneous "cloud" (D), without discrete boundaries between clusters yet with multiple patterns of graded gene expression. Error bars, SD; p<0.021, *p<0.0002, ****p<0.0001 by unpaired t test (b) or two-way ANOVA (d, e, g).
Figure 1J:
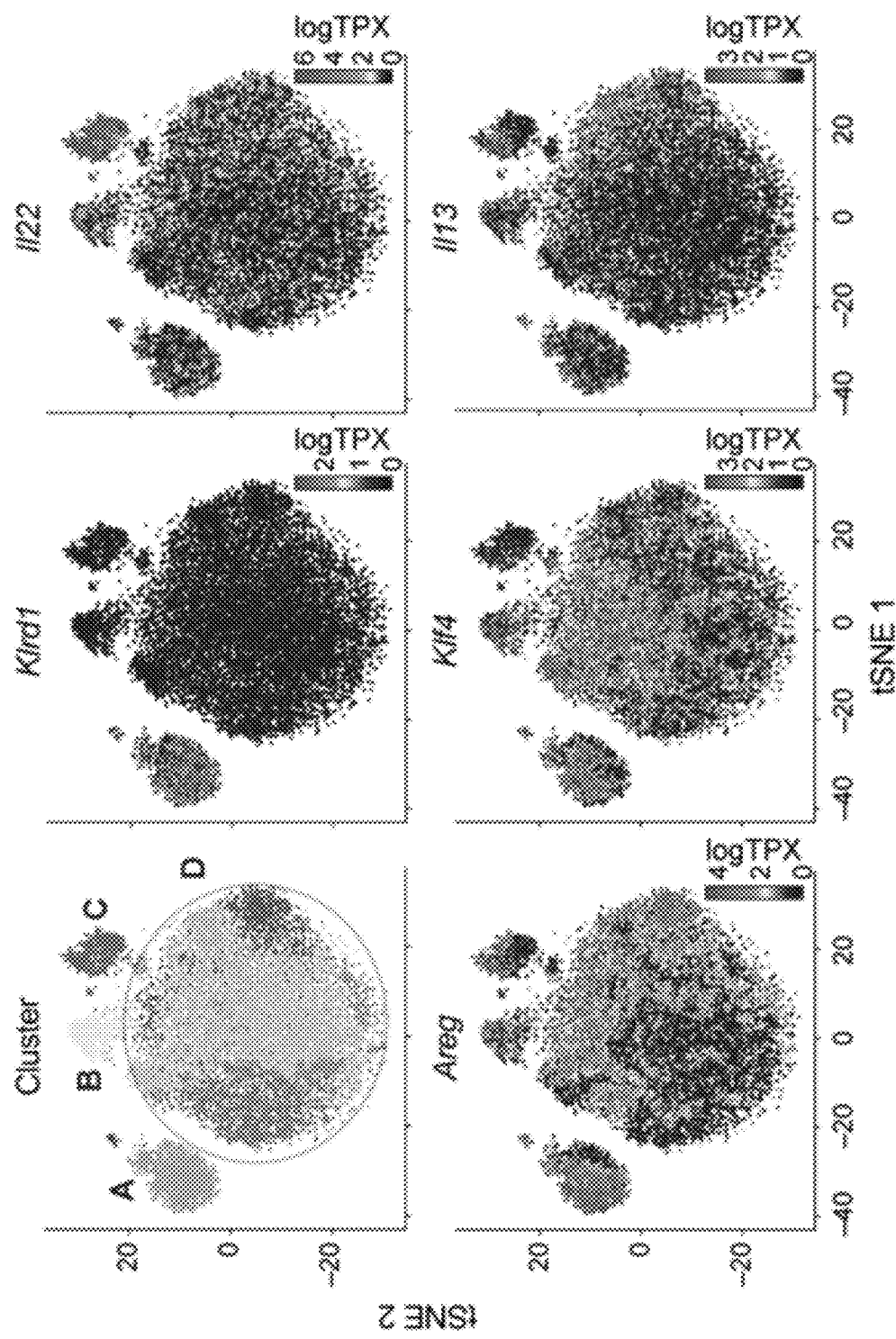
Figure 1K:
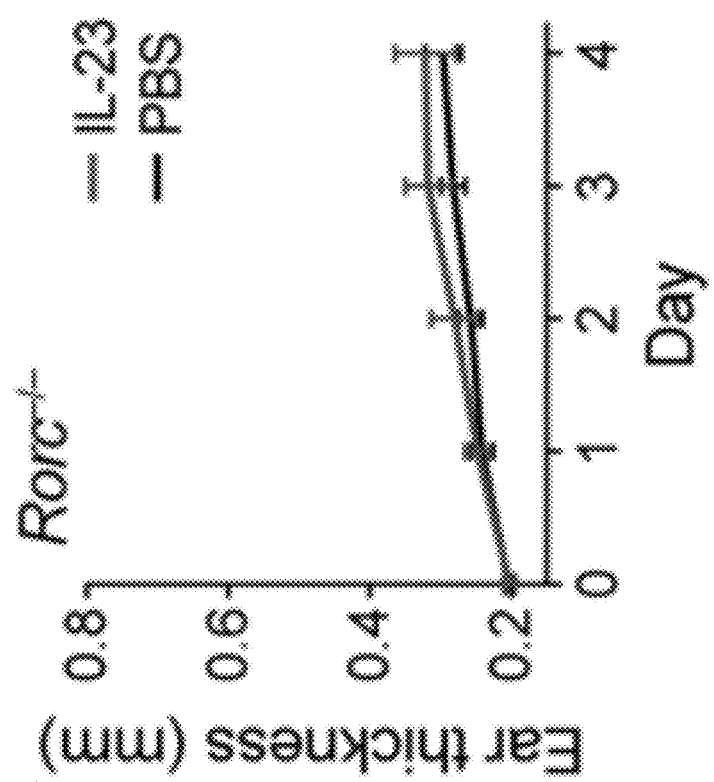
FIG. 1K. IL-23 induced inflammation is dependent on Rorc. Increase in ear thickness (y axis, mm) following treatment with IL-23 or PBS vehicle in Rorc$^{-/-}$ mice.
Figure 1L:
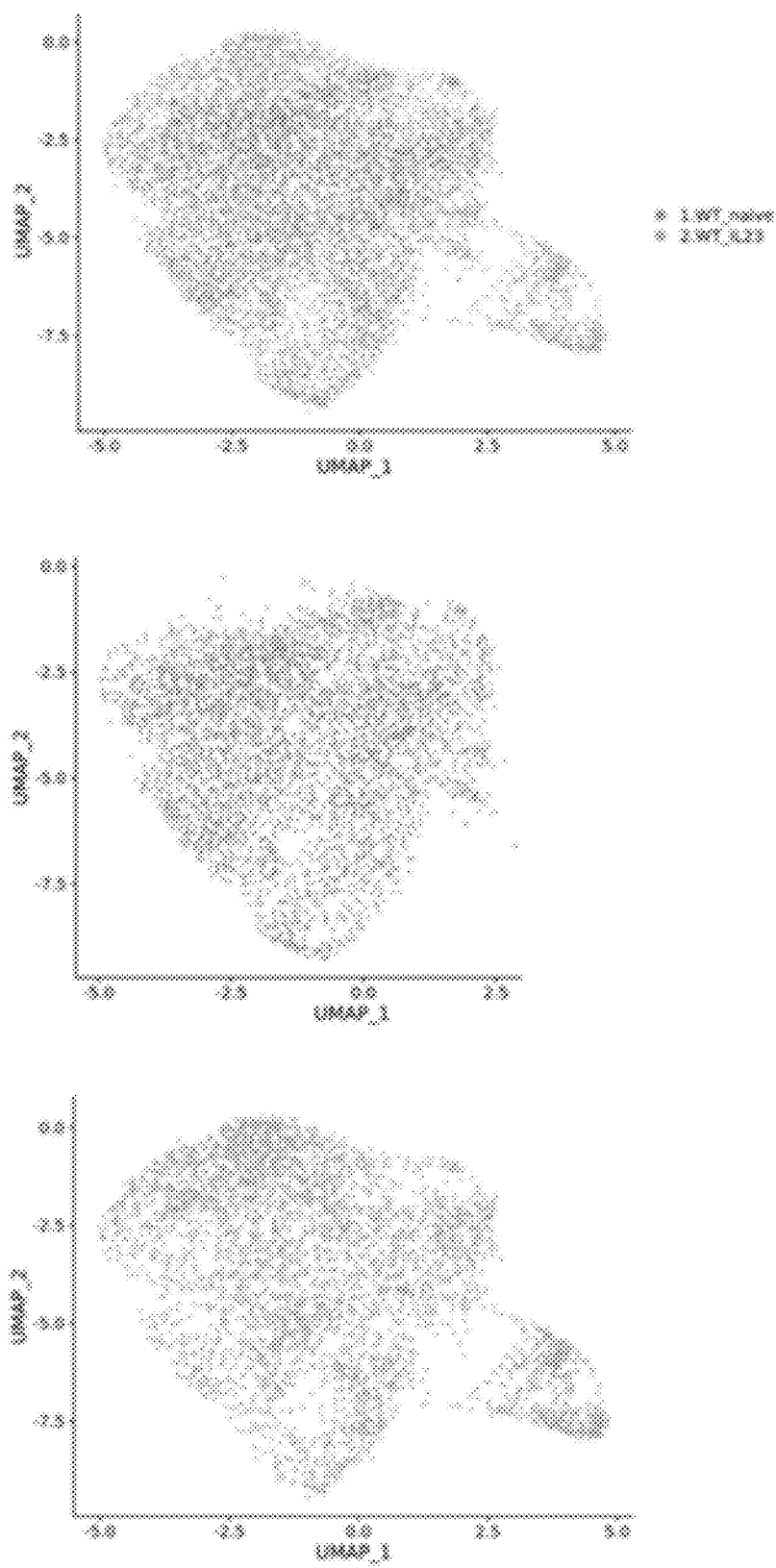
Figure 1M:
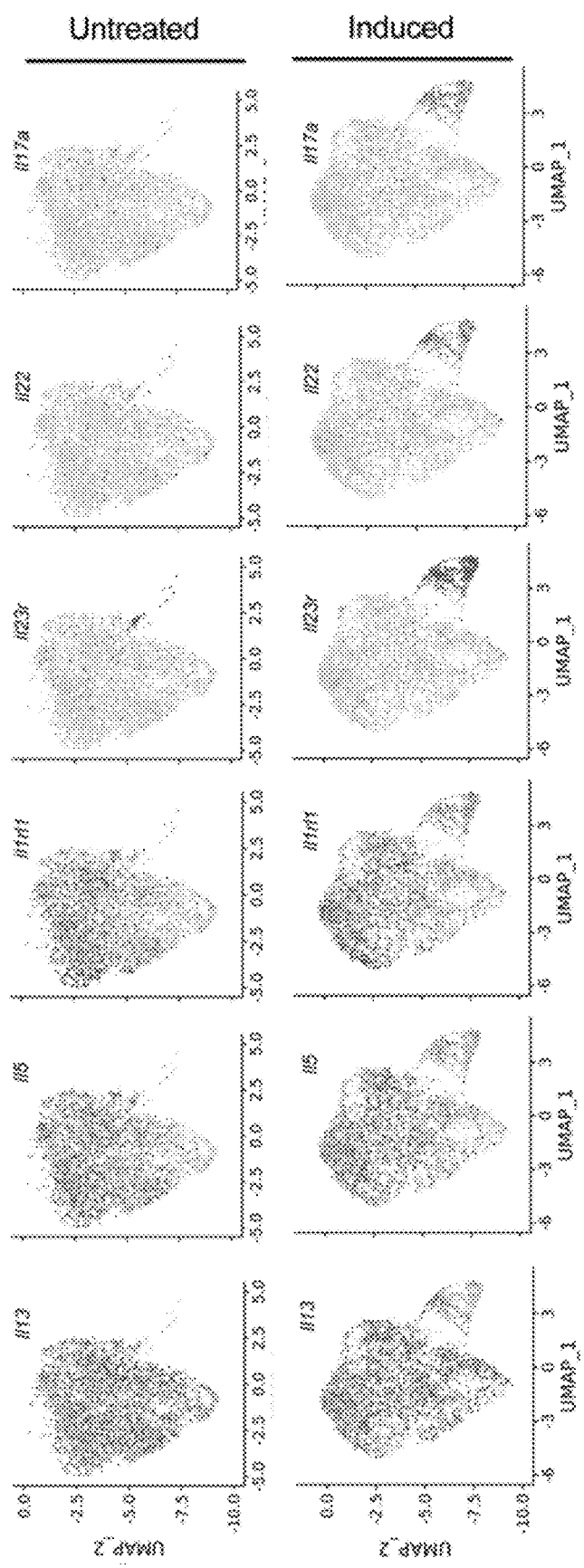
Figure 1N:
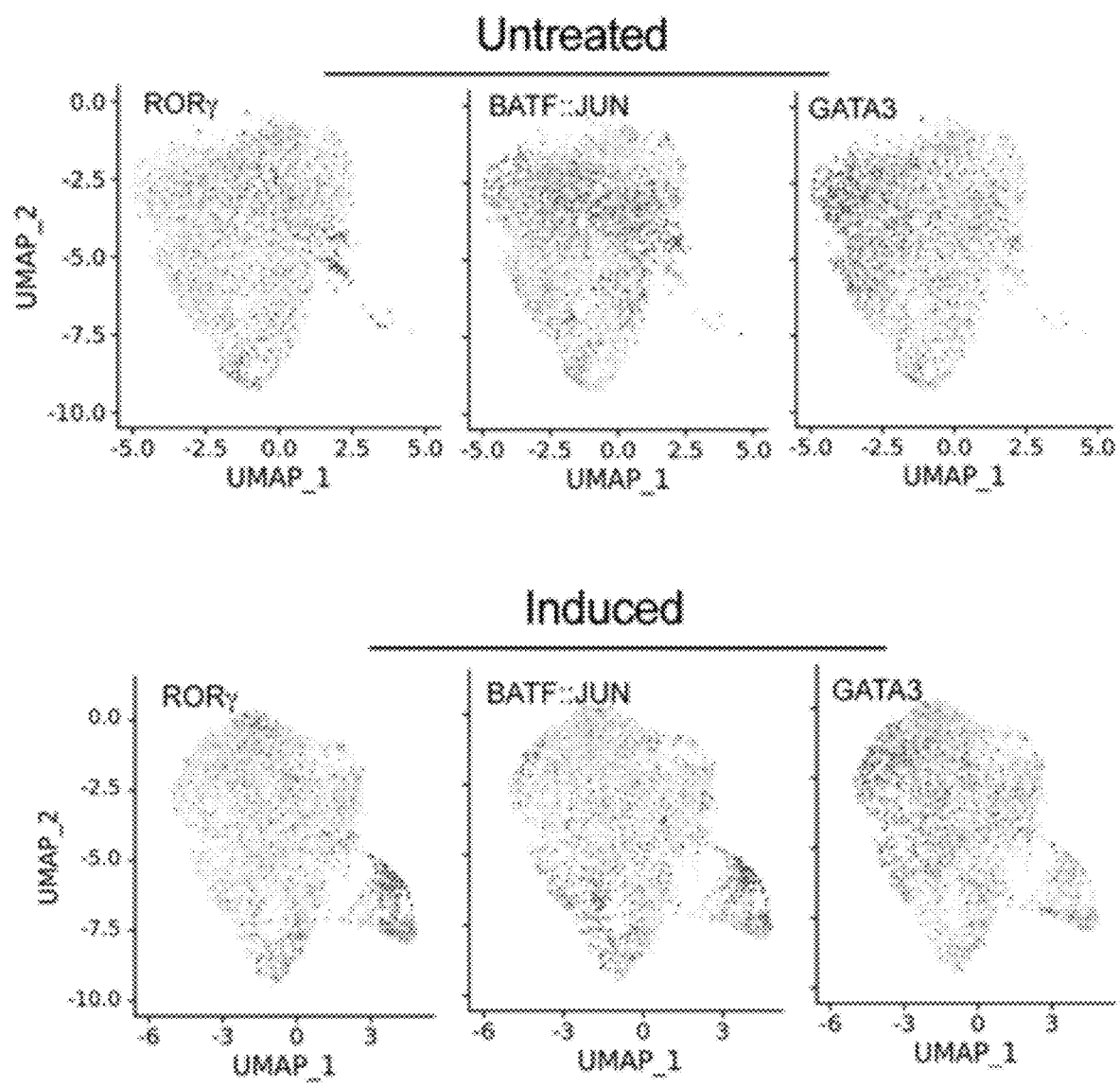

To assess the molecular heterogeneity of skin-resident ILCs and its functional implications for the IL-23 response, Applicants collected massively parallel scRNA-seq profiles from sorted pure total ILCs from WT and Rag1$^{-/-}$ mice from naïve and IL-23 induced conditions, predominantly uncovering a large heterogeneous population of cells (FIG. 1i). Specifically, clustering on principle components, followed by differential expression analysis (Methods), identified a few discrete subsets of cells, including a Rag1$^{-/-}$-specific subset (A), a cluster of proliferating cells from all conditions and genotypes (B), and a cluster specific to the induced condition with very high Il22 expression and some Il13 expression (C) (FIG. 1j, FIG. 5h). However, the vast majority of cells (81%) formed a single, large heterogeneous and continuous "cloud" (D), which was not simply driven by technical factors (Methods), with multiple sub-regions enriched for specific functional programs, including type 2 immune response (FIG. 1j). Importantly, no single partitioning conformed to the expression of key genes and processes, and moreover, some biological processes were unexpectedly shared across subsets of the cells from distinct clusters (FIG. 1j). This highlighted the diversity of potential cell states, and the need to capture them by more nuanced computational analysis.

Figure 2D:
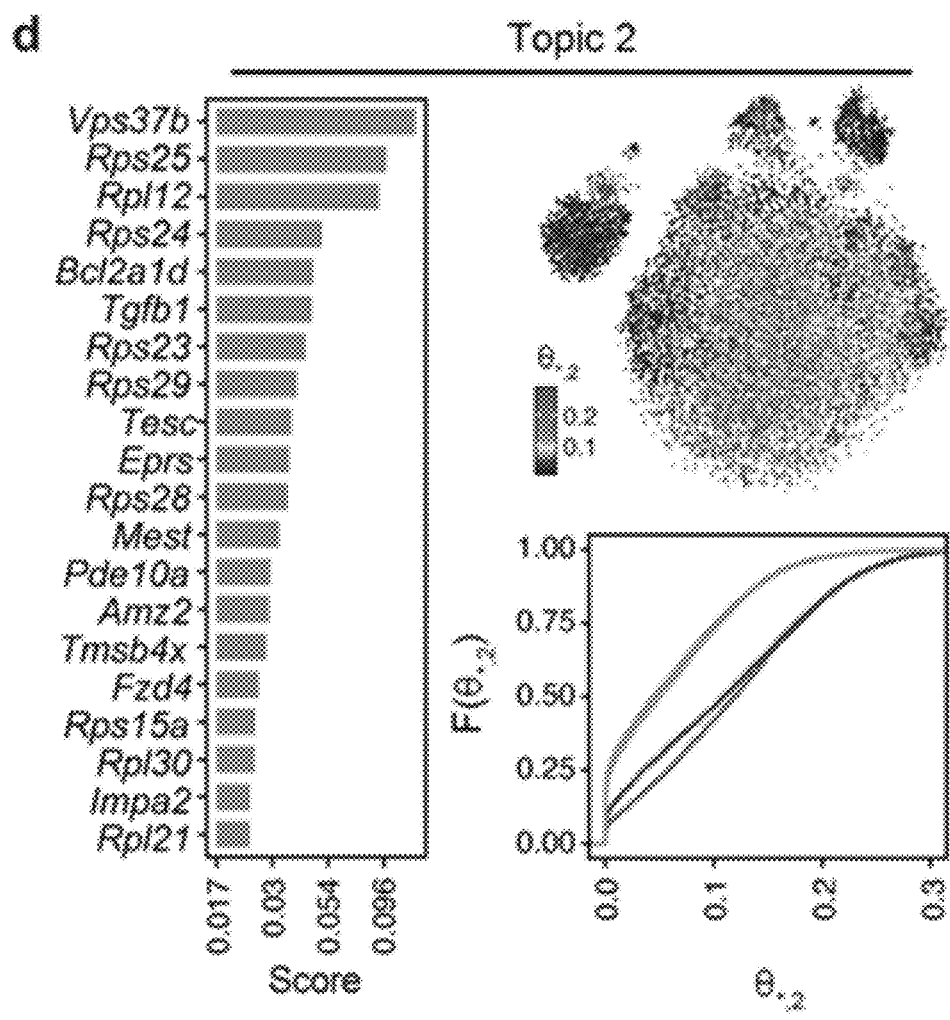
Figure 2D:
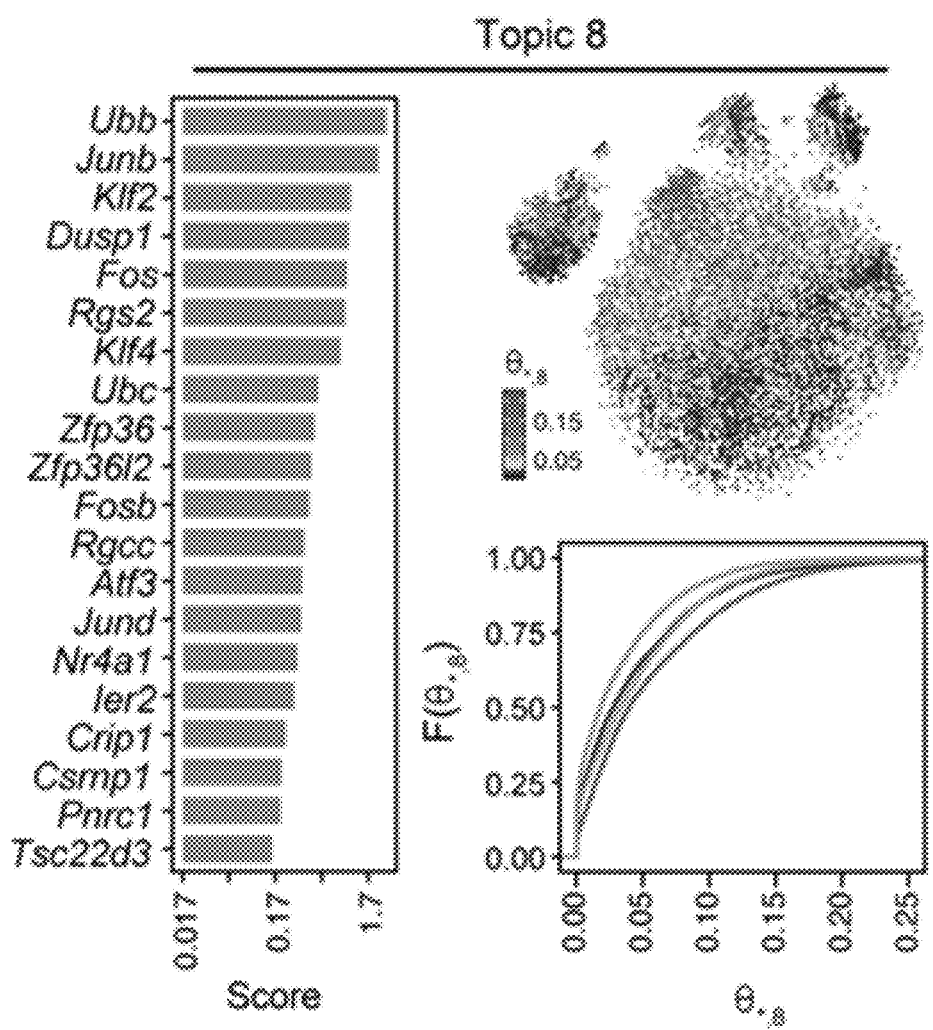
Figure 2D:
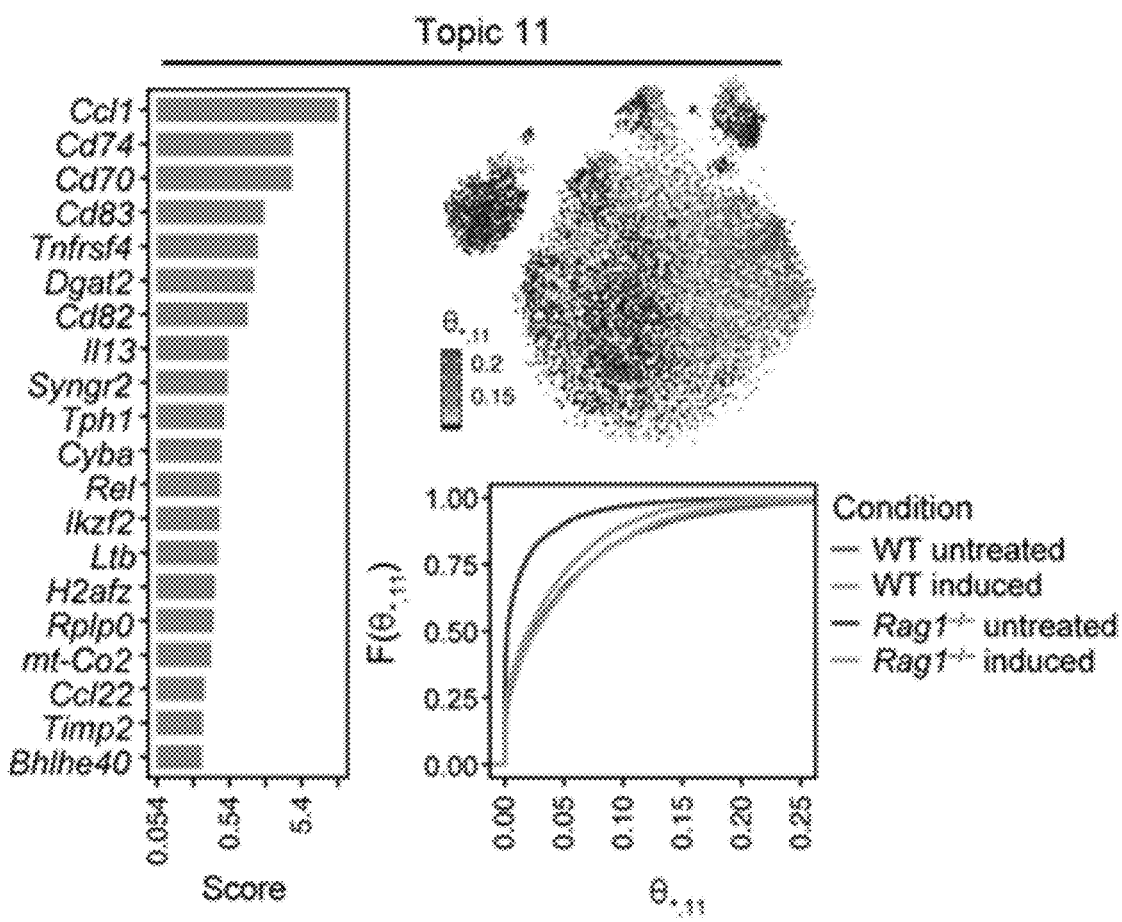
Figure 2D:
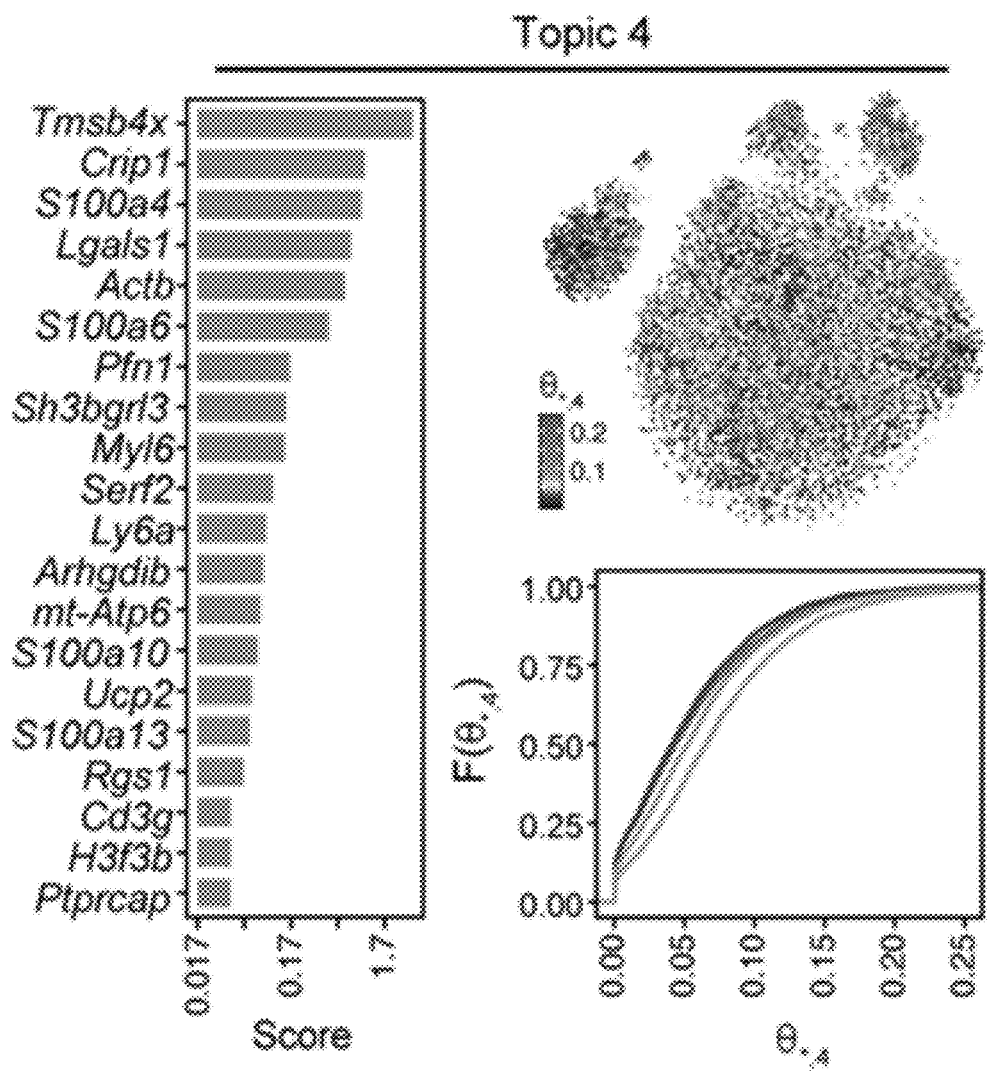
Figure 2D:
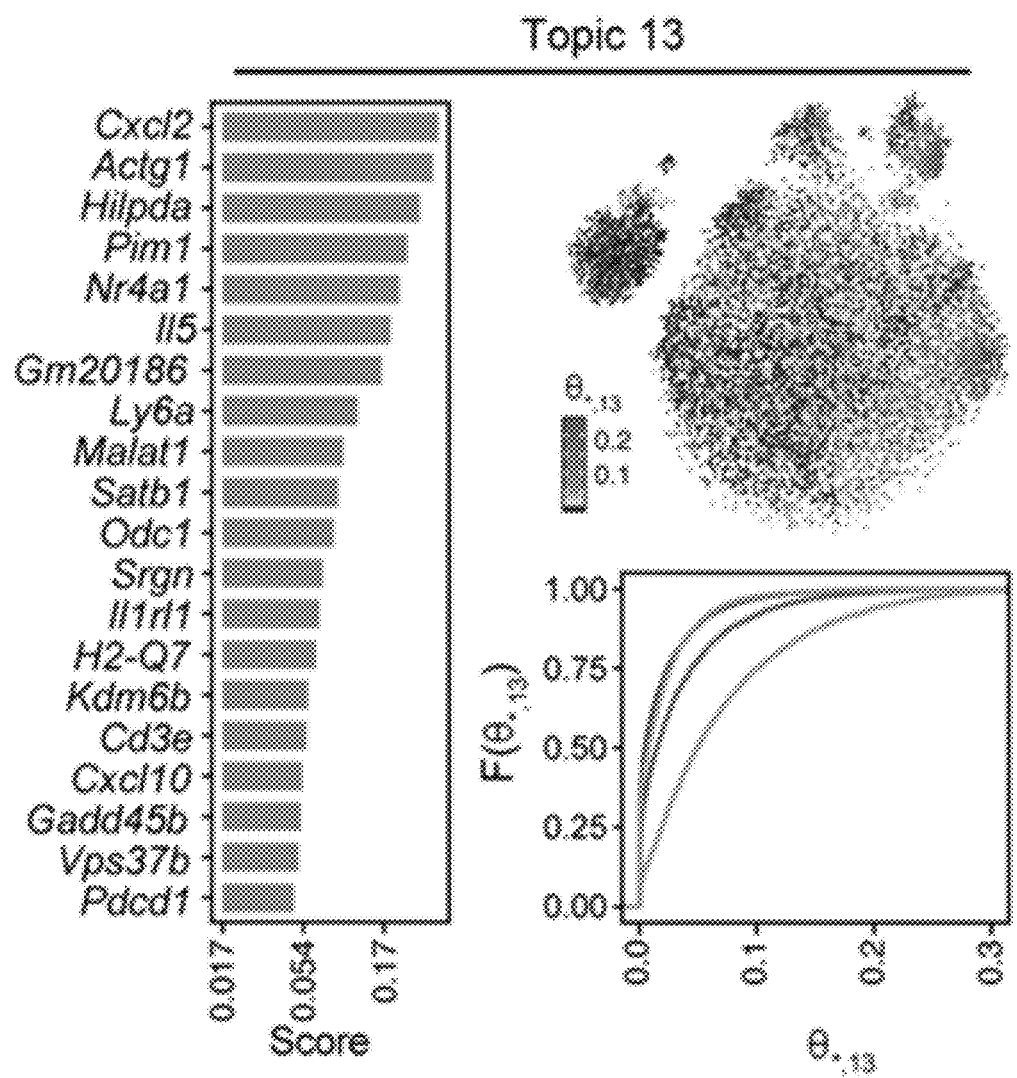
Figure 2D:
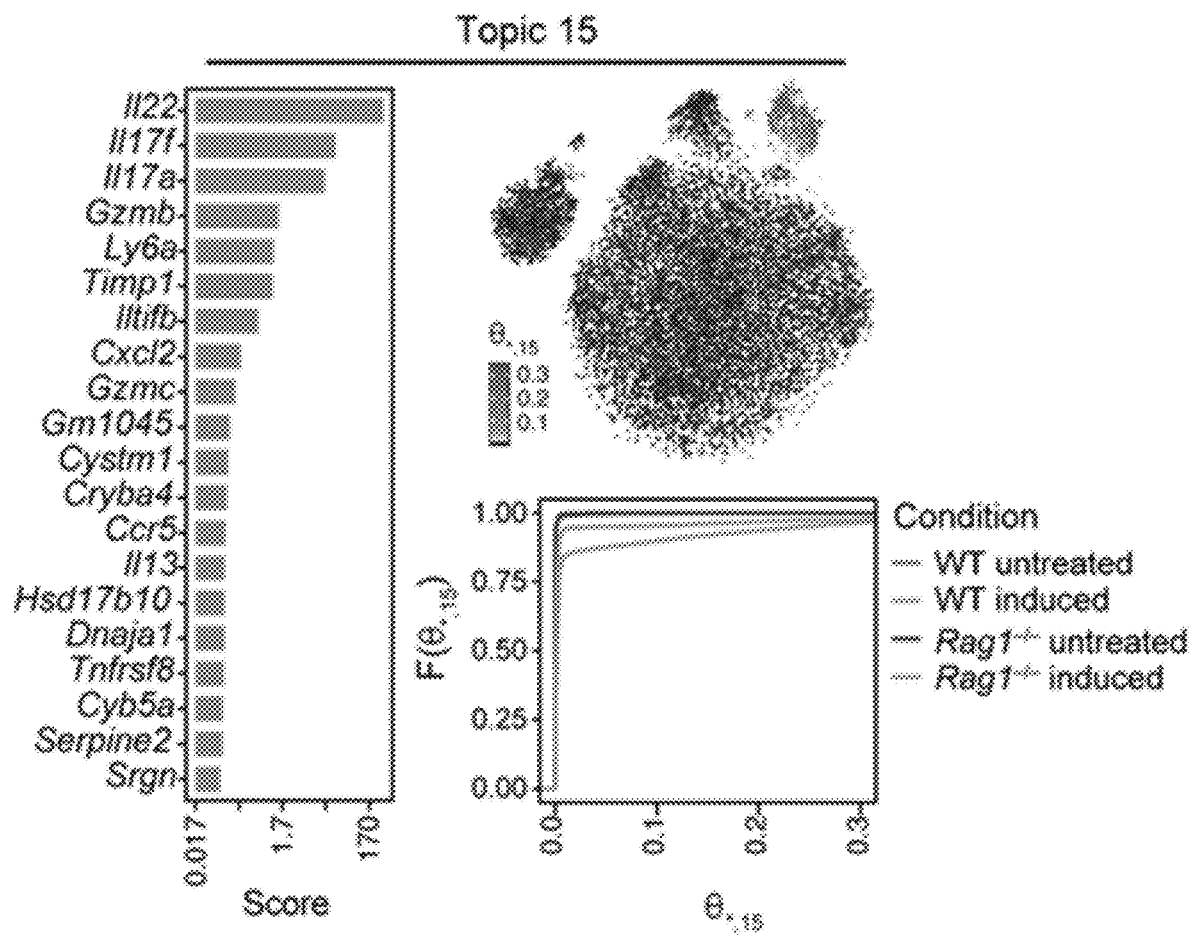
Figure 2E:
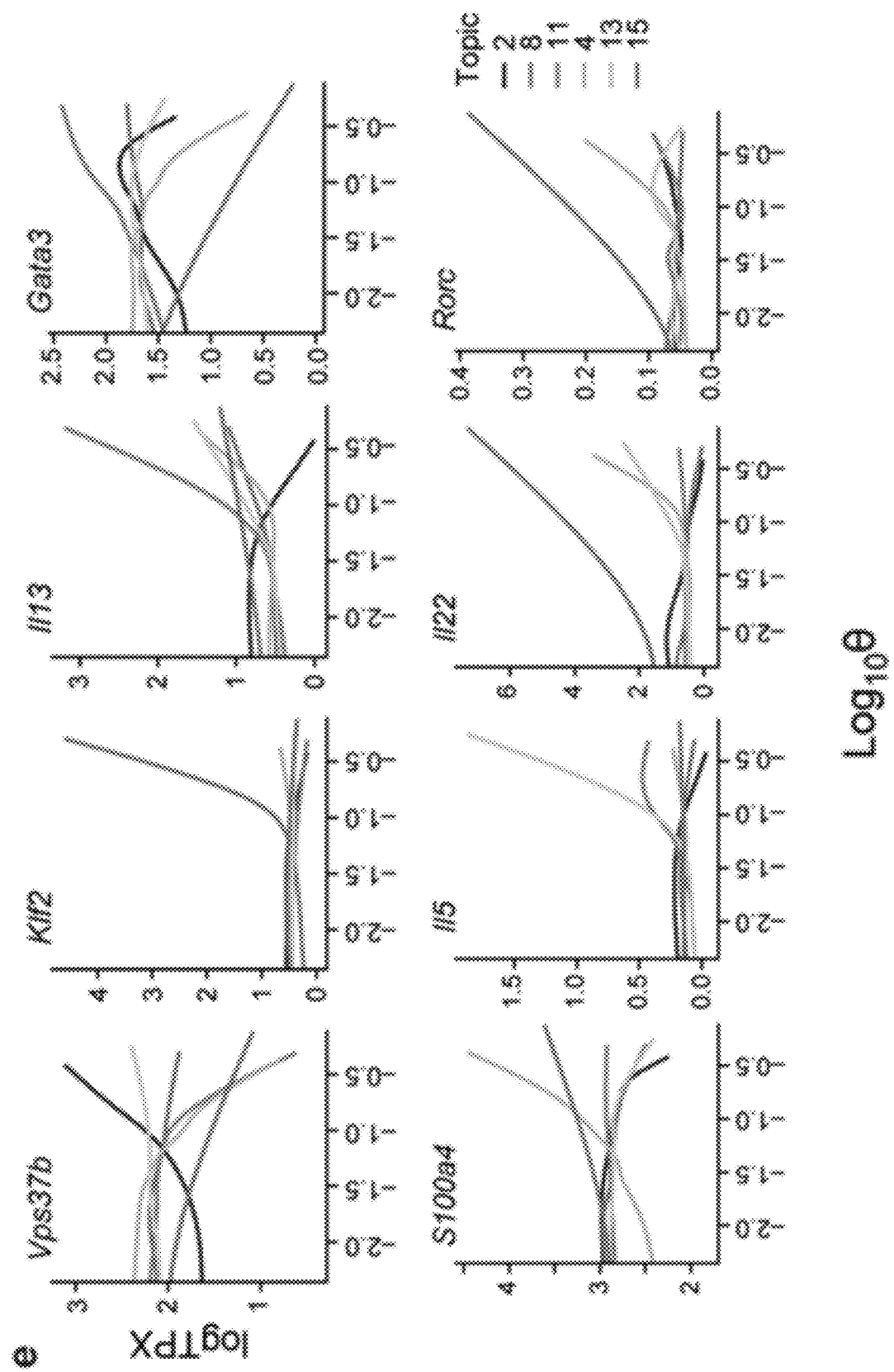

As an alternative to partitioning these continua into discrete clusters, Applicants created a generative model based on latent Dirichlet allocation (LDA), or "topic modeling", a statistical data mining approach for discovering the abstract topics that explain the words occurring in a collection of text documents[24]. Applied to scRNA-Seq, each "document" corresponds to a cell, and a "topic" corresponds to a biological program, modeled as a distribution over expressed genes, rather than words (FIG. 2a). Analogous to a text document, a cell is modeled as a mixture of a small number of topics, where the mixture weights indicate the relative prominence of the corresponding biological process in that cell. Multiple topics may include the same gene, reflecting the gene's roles in different processes. Given the number of topics as a parameter, both topics and the mixture weights in cells are inferred without supervision. Several choices for the number of topics may result in valid models, though too large a number of topics can result in overfitting and low interpretability. LDA was independently introduced in population genetics to model admixed individuals with ancestry from multiple populations[25]. In genomics, it has been applied to deconvolute cell types in population RNA-seq[26-32], and proposed for finding structure in bulk or single-cell RNA-seq, for example, in inference of confounding batch effects[33].

Figure 6A:
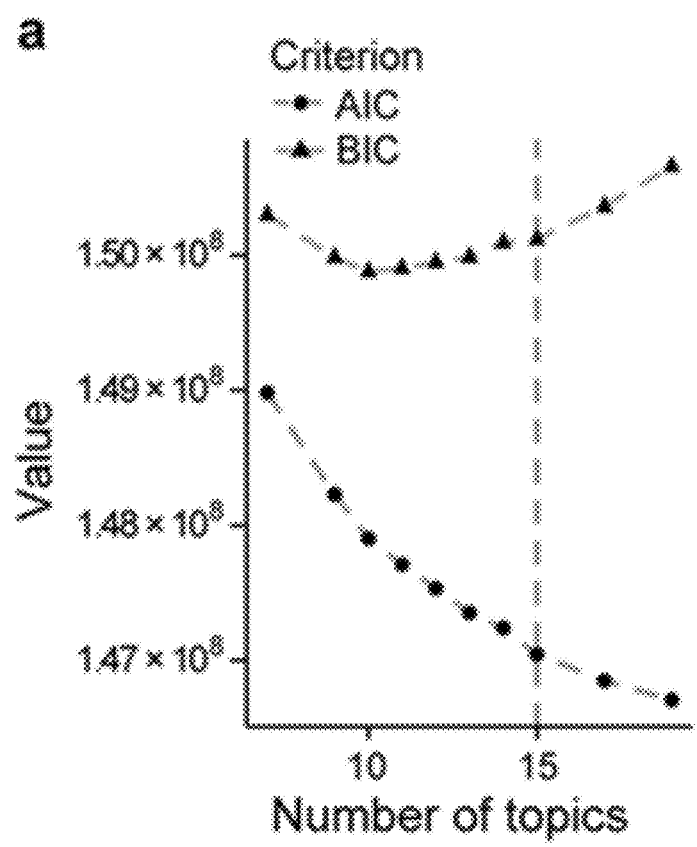
FIG. 6A-FIG. 6D—Topic modeling also distinguishes cluster-specific, cell size, and cell quality related topics.

Topic modeling thus permits a cell to have multiple, non-hierarchical "identities" that potentially differ in importance, a feature particularly relevant for analyzing cellular plasticity (FIG. 2a). Indeed, Applicants observed complex patterns of topic sharing across clusters, suggesting that topic weights capture relationships not well described by clusters and, through their functional interpretation, enable a more nuanced view of similarities and differences among cells (FIG. 2b). A choice of 15 topics captured important changes during disease induction, as well as other signals, without obvious signs of overfitting (FIG. 6a, Methods).

Figure 6B:
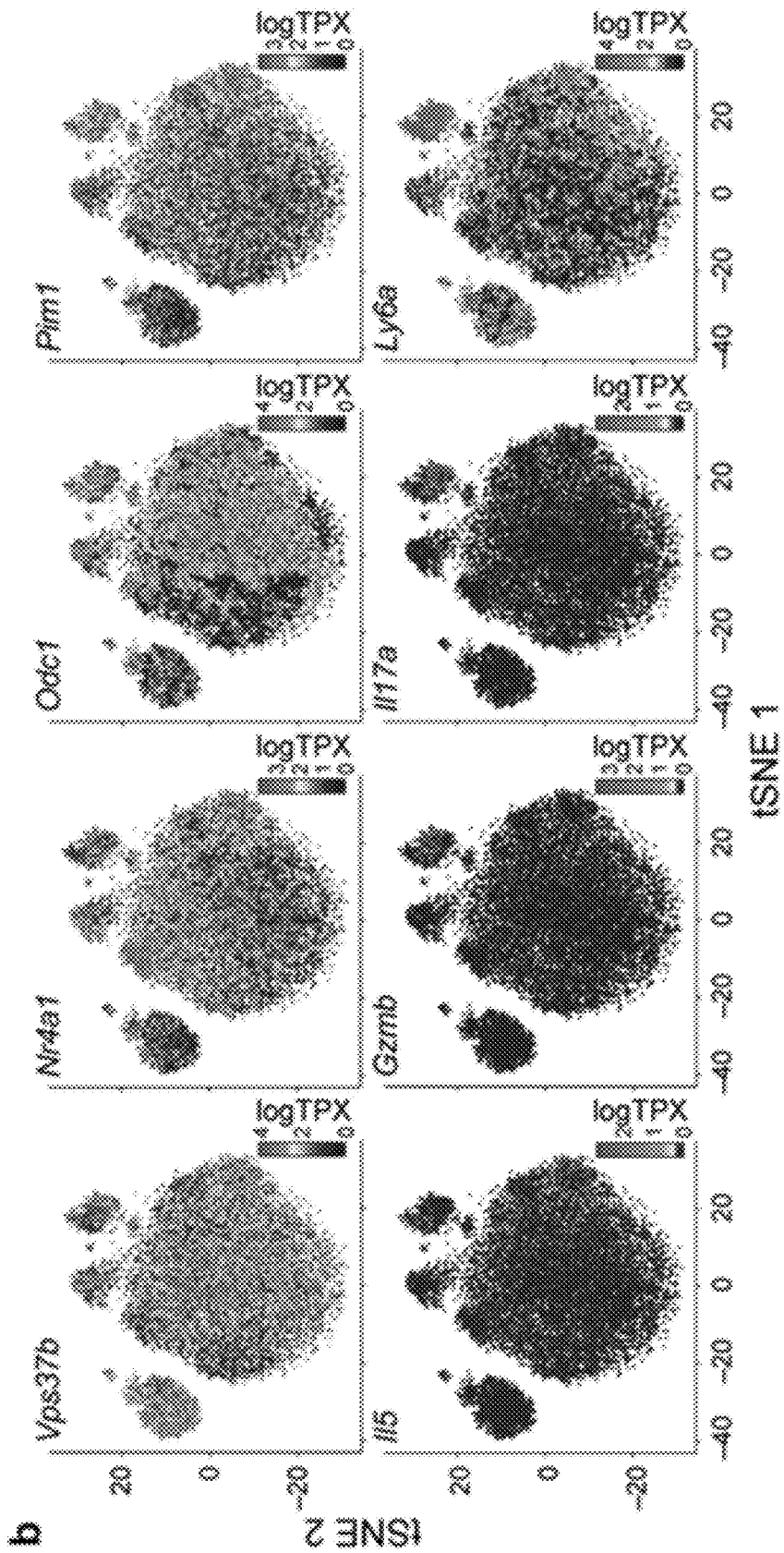
Figure 6C:
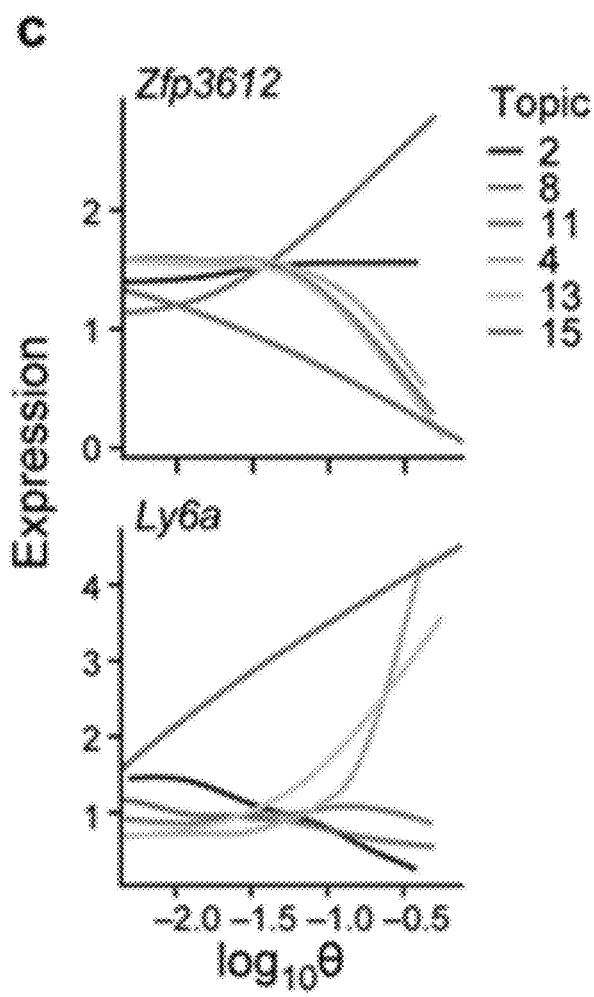
Figure 6D:
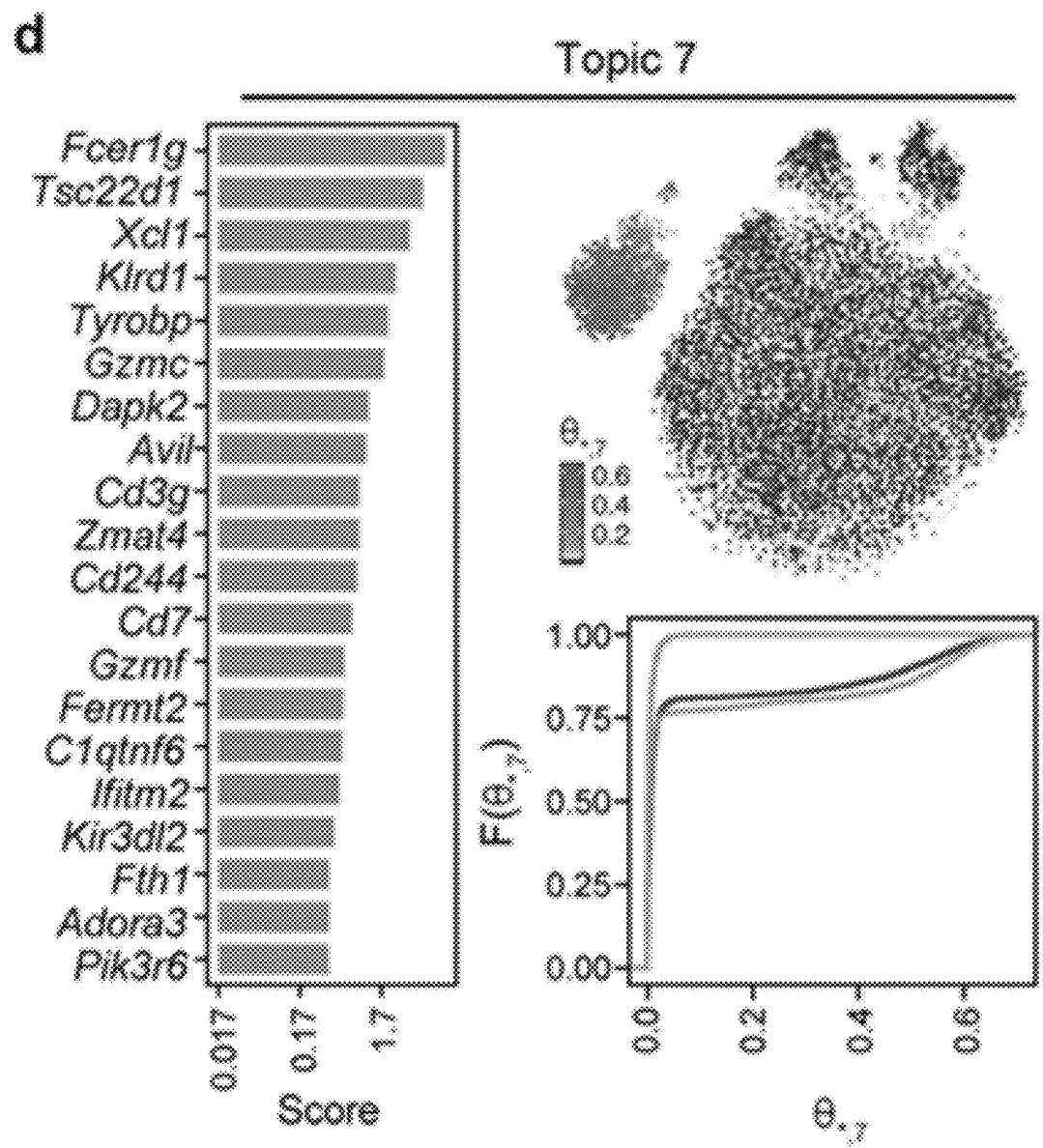
Figure 6D:
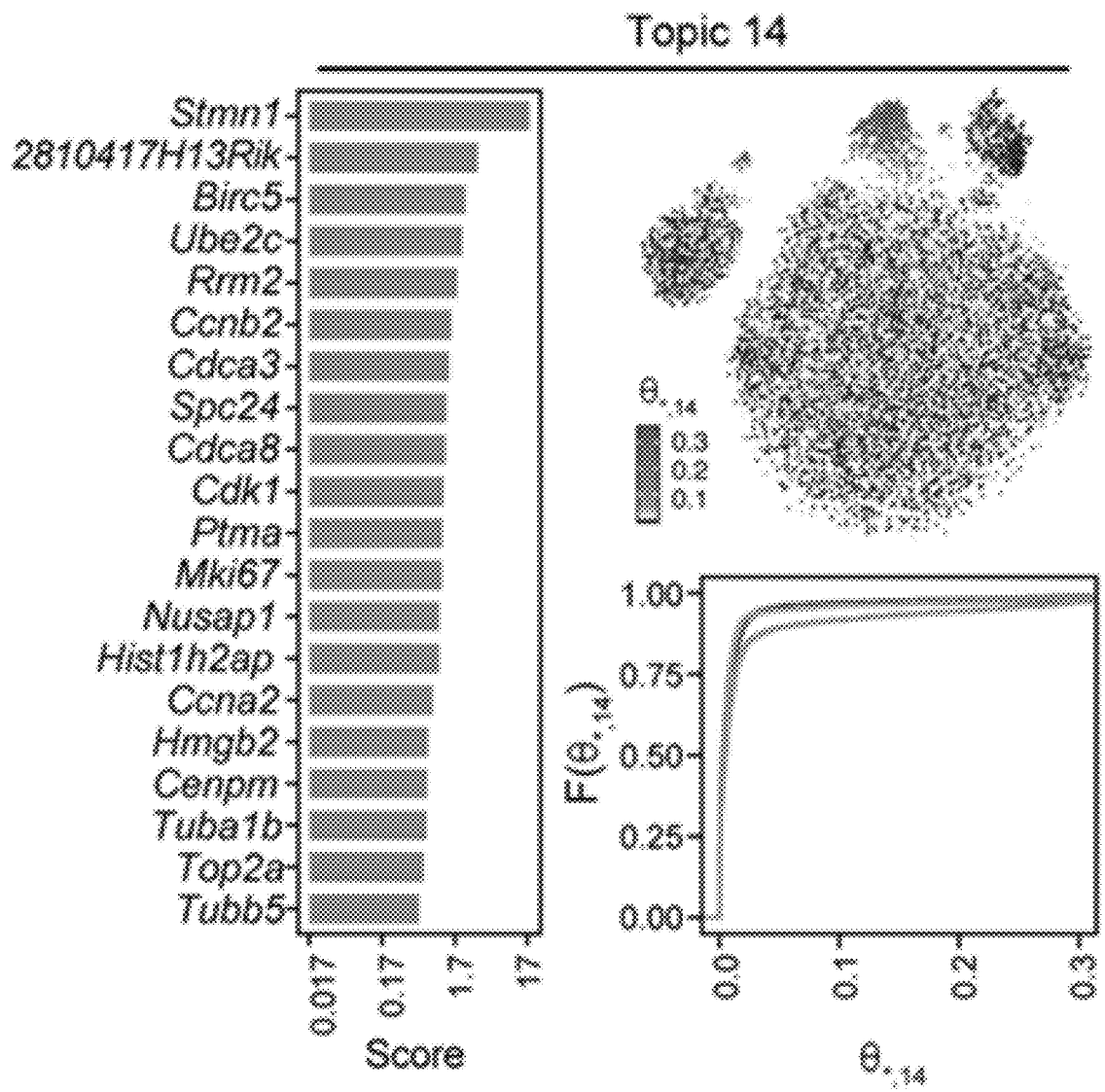
Figure 6D:
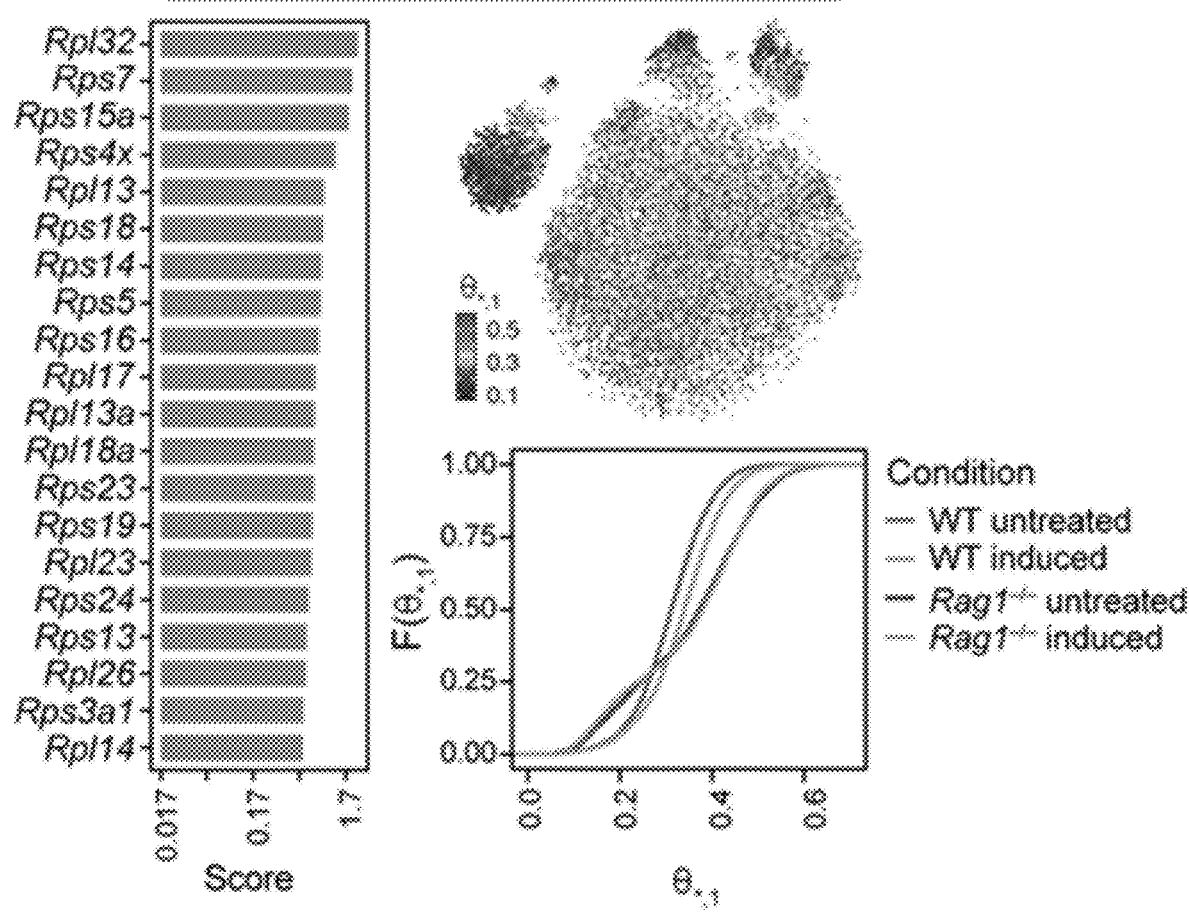
Figure 6D:
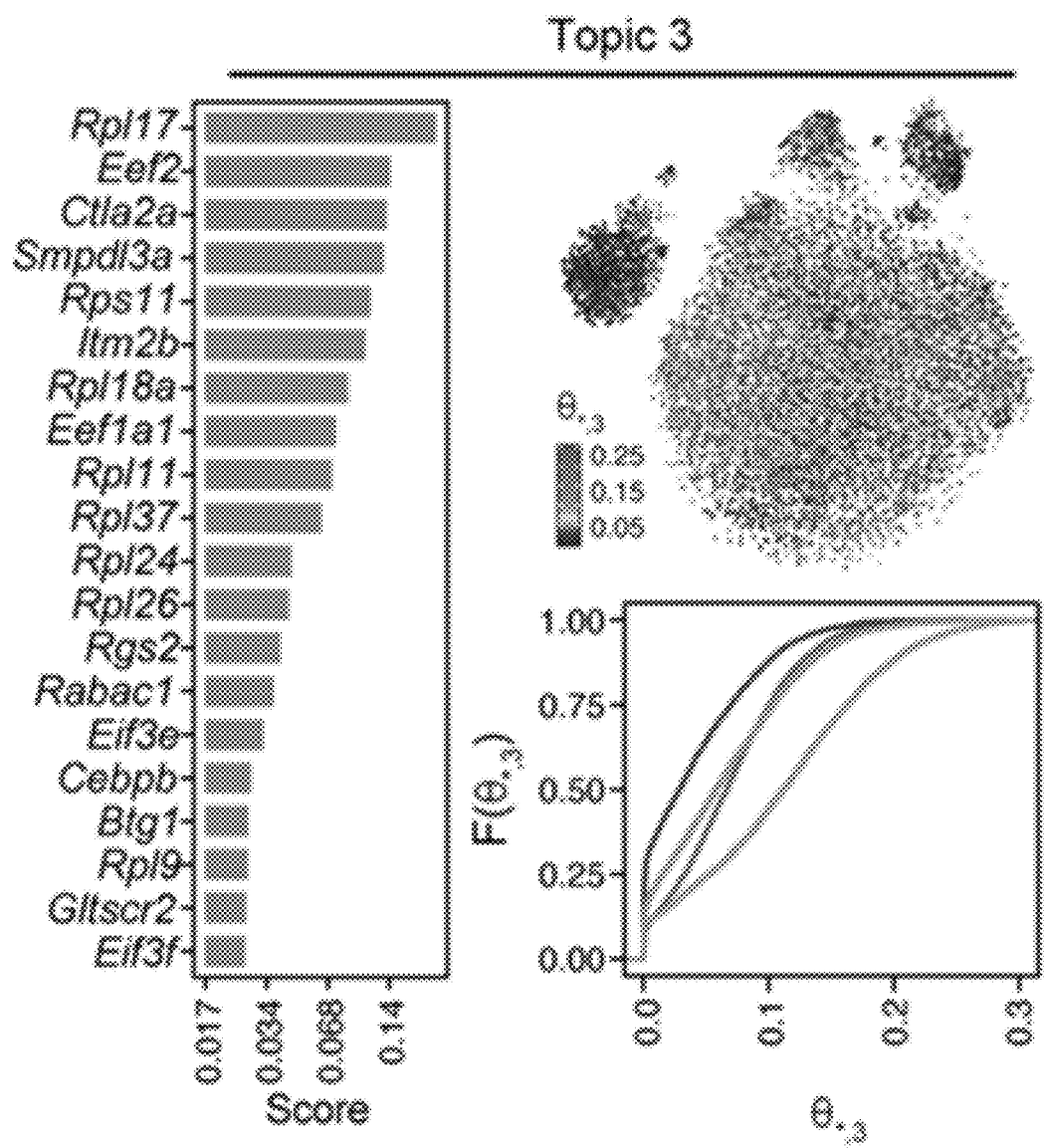
Figure 6D:
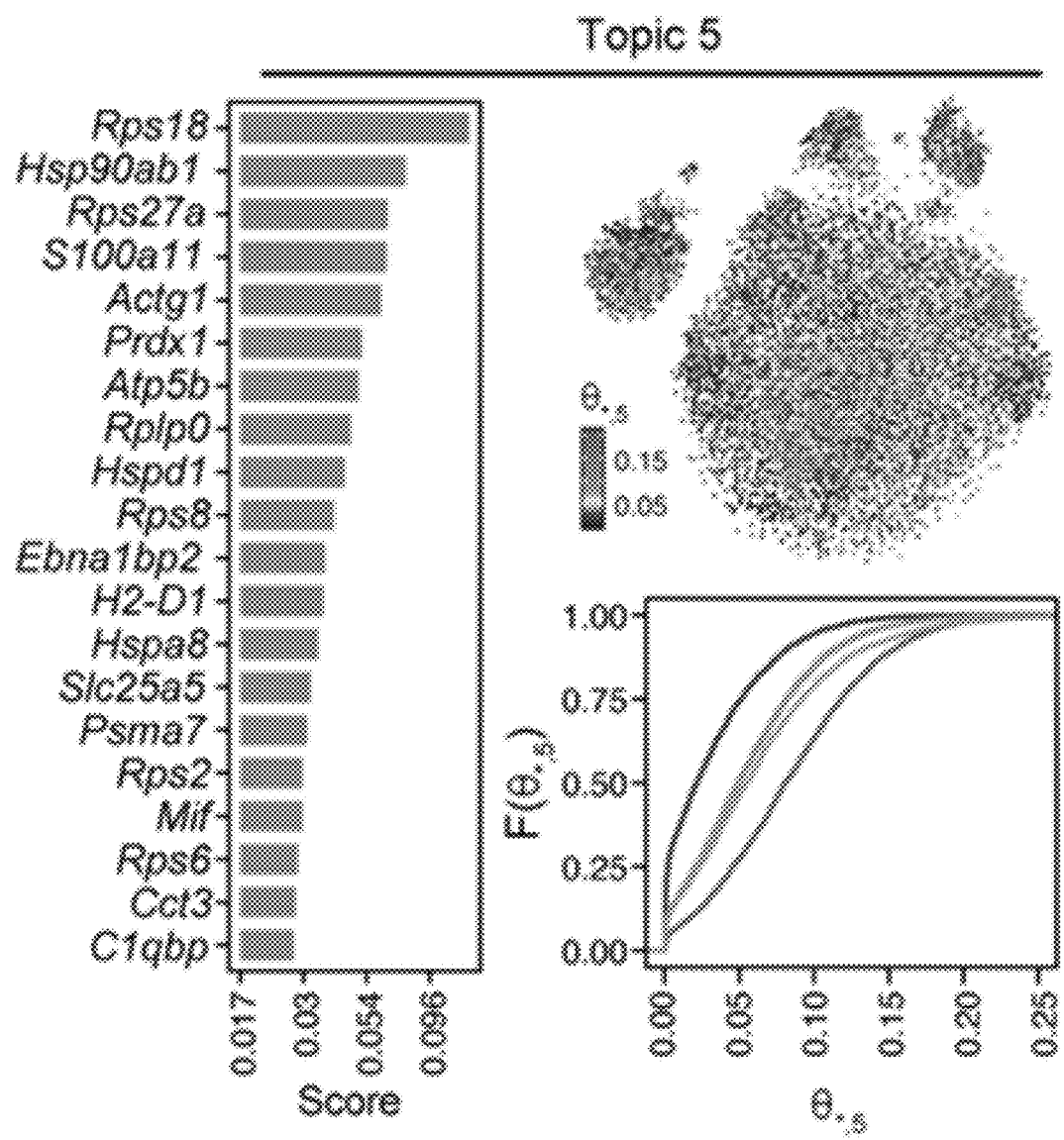
Figure 6D:
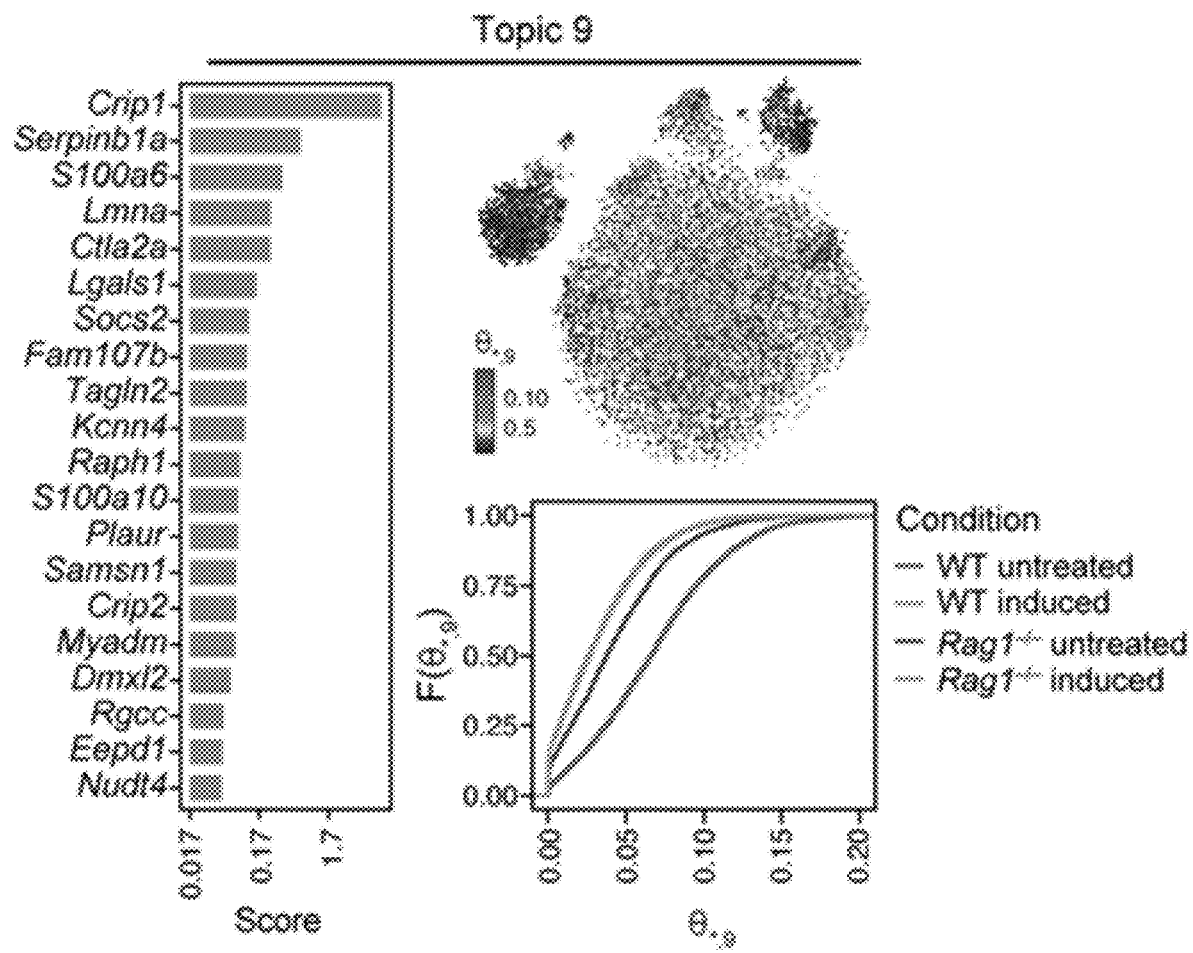
Figure 6D:
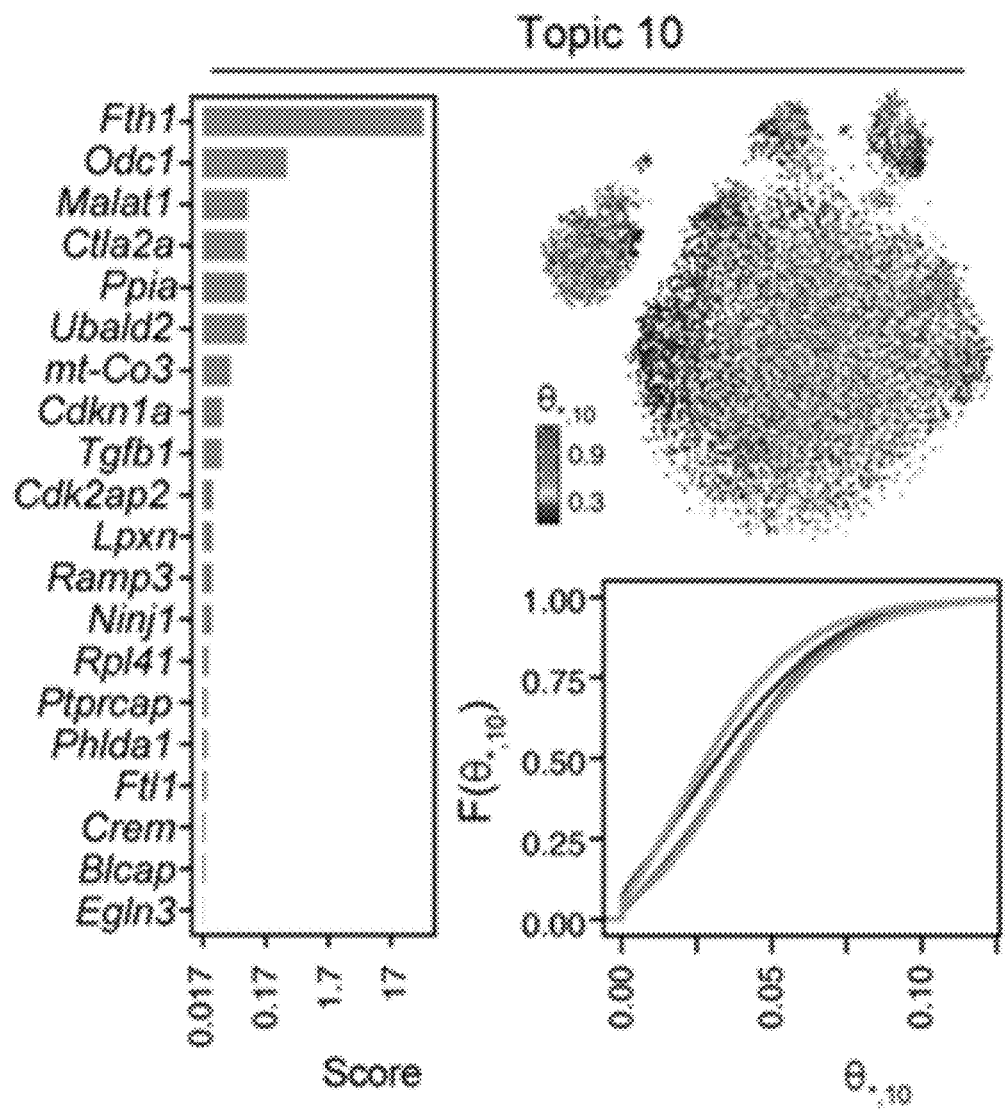
Figure 6D:
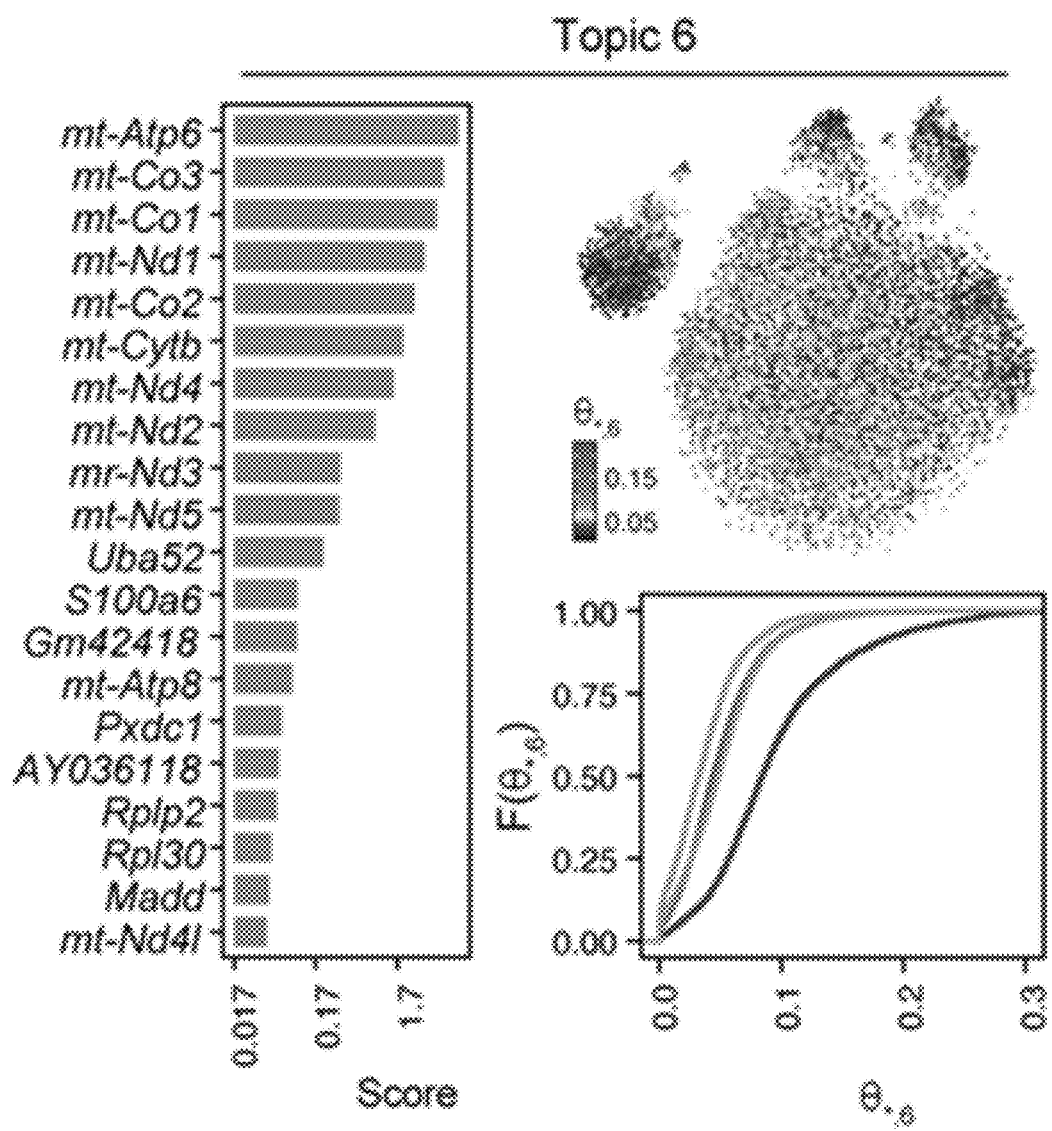
Figure 6D:
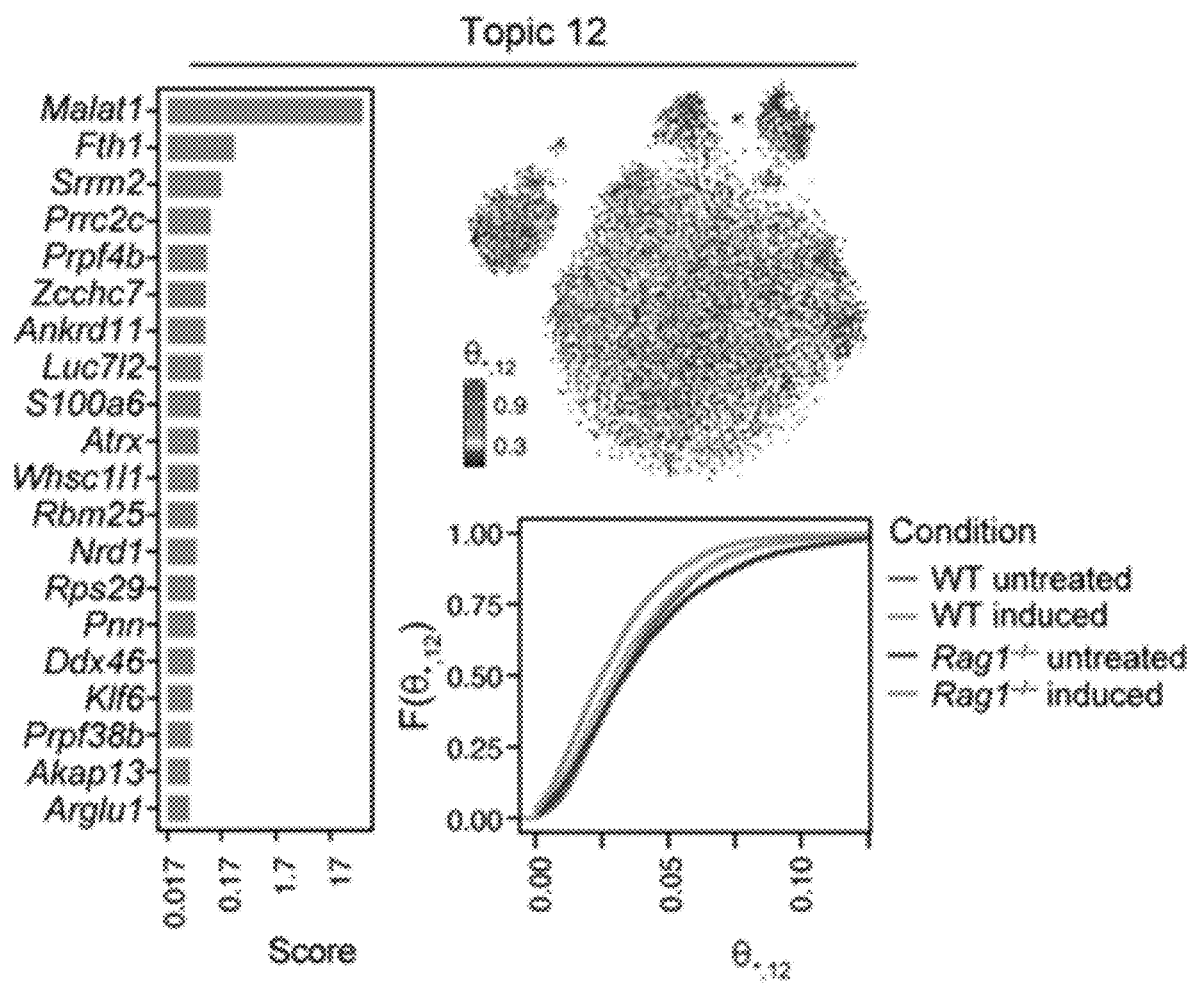

The topics spanned three categories: (1) highly ribosomal- or mitochondrial-dominated (e.g., Topic 1, 6), possibly reflecting technical quality or cell size, (2) cluster-specific topics (e.g., Topic 7, 14, 15), and (3) "sub-regional" topics, that is, those featured in sub-regions of the "cloud", also often simultaneously present in sub-regions of other clusters (e.g., Topics 2, 4, 8, 11, 13) (FIG. 2c,d, FIG. 6b-d, FIG. 9). "Cell quality" topics can help distinguish the influence of technical confounders better than simple thresholds, but also may reflect a cell's level of biological activation[34]. "Cluster-specific topics" are analogous to results from standard differential expression analysis. For example, cluster C is unique in having large weights for Topic 15, which is characterized by expression of ILC3-associated genes Il22, Il17a, and Il17f, as well as the cytotoxic gene Gzmb and the type 2 genes Ly6a (Sca-1) and Il13 (FIG. 2c,d, FIG. 6b,c). As another example, Topic 7 is uniquely highly weighted in cells from the $Rag1^{-/-}$ specific cluster A, and features the NK-associated genes Klrd1 and Tyrobp and the immunoglobulin E receptor Fcer1g, indicating that $Rag1^{-/-}$ mice might have an overrepresentation of skin-resident ILC1s (FIG. 1j, FIG. 6d).

The "sub-regional" topics highlighted functional states that are prominent within the "cloud" and span across cluster boundaries, showing that ILCs from untreated skin span a spectrum of immune states, including one characterized by Vps37b expression (Topic 2), a naïve/quiescent like state (Topic 8) and an activated state related to antigen presentation (Topic 11). Notably, this may mirror "functional compartmentalization" reported in gut ILCs in homeostasis[35]. This spectrum shifted upon disease induction, giving rise to greater representation of classical Il5- and Il13-expressing "ILC2s" (Topic 13), as well as a mixed ILC2/ILC3-like state characterized by strong expression of Il13, Il17, and Il22 (Topic 15) (FIG. 2c,d, FIG. 6b). Specifically, Topic 2, mainly present in the "cloud", distinguishes between the untreated and induced conditions, partly through ribosomal genes that may reflect differences in size between naïve and activated cells (FIG. 2c). Topic 8 is characterized by expression of TFs previously associated with both T- or B-cell quiescence, such as Klf2/Klf4[36-37] and Zfp3612[38,39], and with repression of Th17 genetic programs, such as Tsc22d3[40], and may thus reflect an actively maintained quiescent ILC state (ILC0) (FIG. 2c,d, FIG. 6c). Topic 11, which is present in cells from both WT conditions and the $Rag1^{-/-}$ induced condition, features genes associated with antigen presentation, including MHCII invariant chain and MIF receptor Cd74[41] and Cd83[42], and type 2 ILCs (e.g., Il13, Ccl1, and Dgat2, though not Il5)[34,35,43,44] (FIG. 2c,d). Topic 13, highlighting a substantial sub-region of both the "cloud" and induced-specific cluster C, is more specific to WT disease induction, uniquely expresses 115, and also includes other type 2 genes, such as Cxcl2, Il1rl1 (ST-2), Il13, and Ly6a (Sca-1), the latter of which featured in all induced topics (FIG. 2c,d, FIG. 6b,c). The presence of some cells with high weights for both Topics 13 and 15 indicates that an activated type 2 response apparently coexists with the anticipated type 3 response. Finally, Topic 4, which is largely mutually exclusive with Topic 13 across cells, includes genes involved in actin remodeling, a process previously shown to be important during T-cell activation[45] (FIG. 2c,d).

Figure 7A:
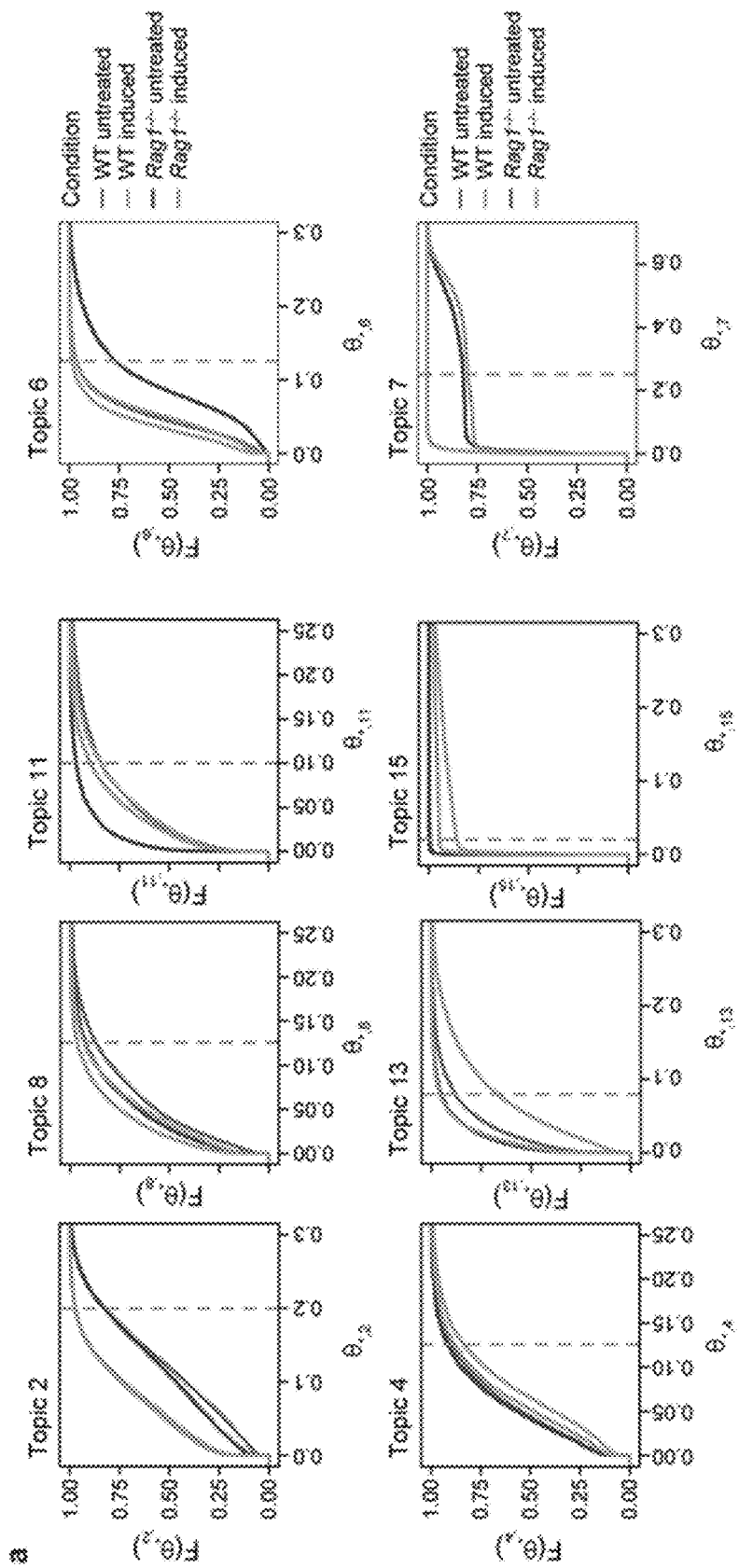
FIG. 7A-FIG. 7E—Diffusion map analysis based on topic model highlights an IL-23-induced dynamic trajectory.
Figure 7B:
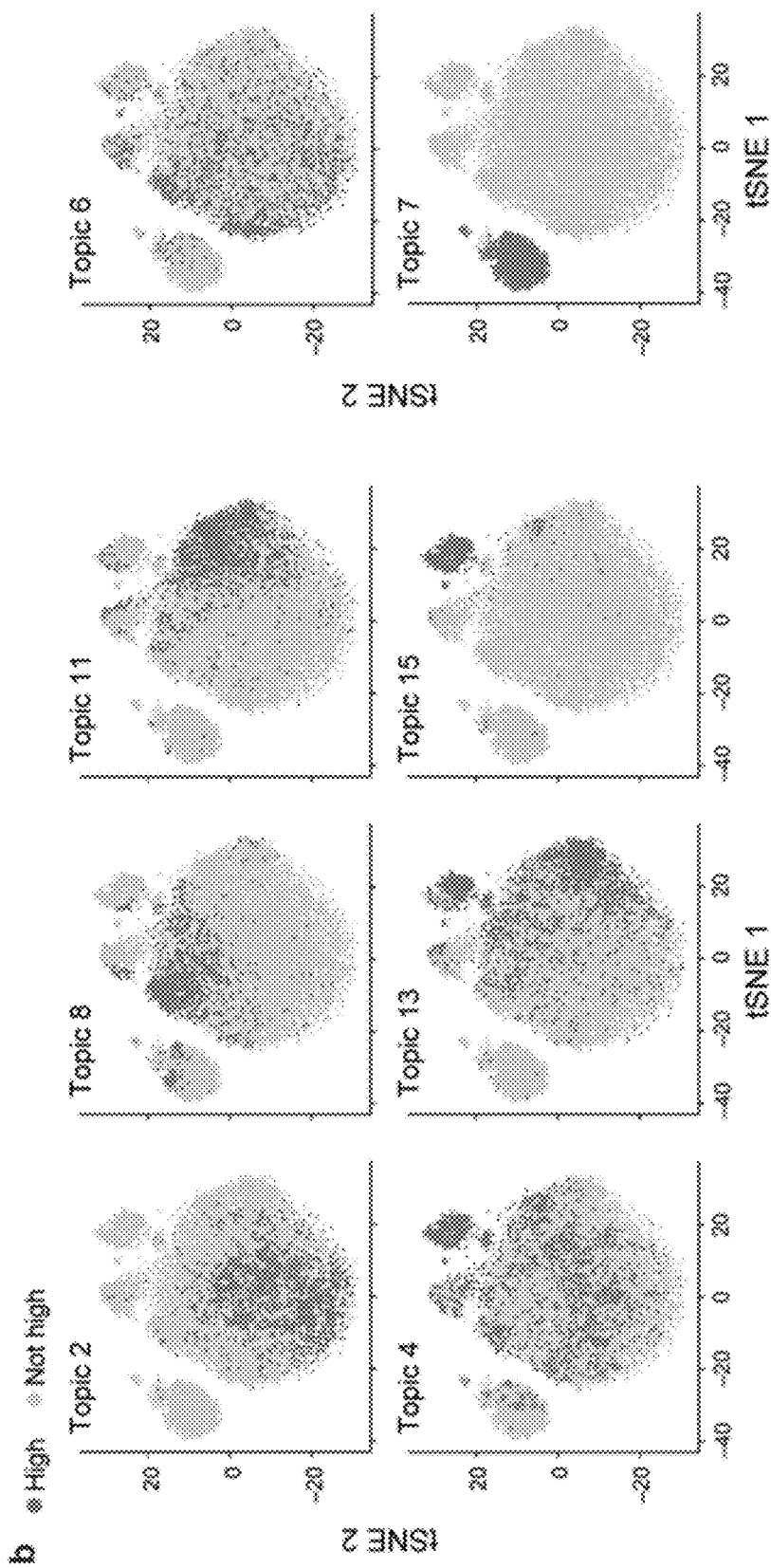
Figure 7C:
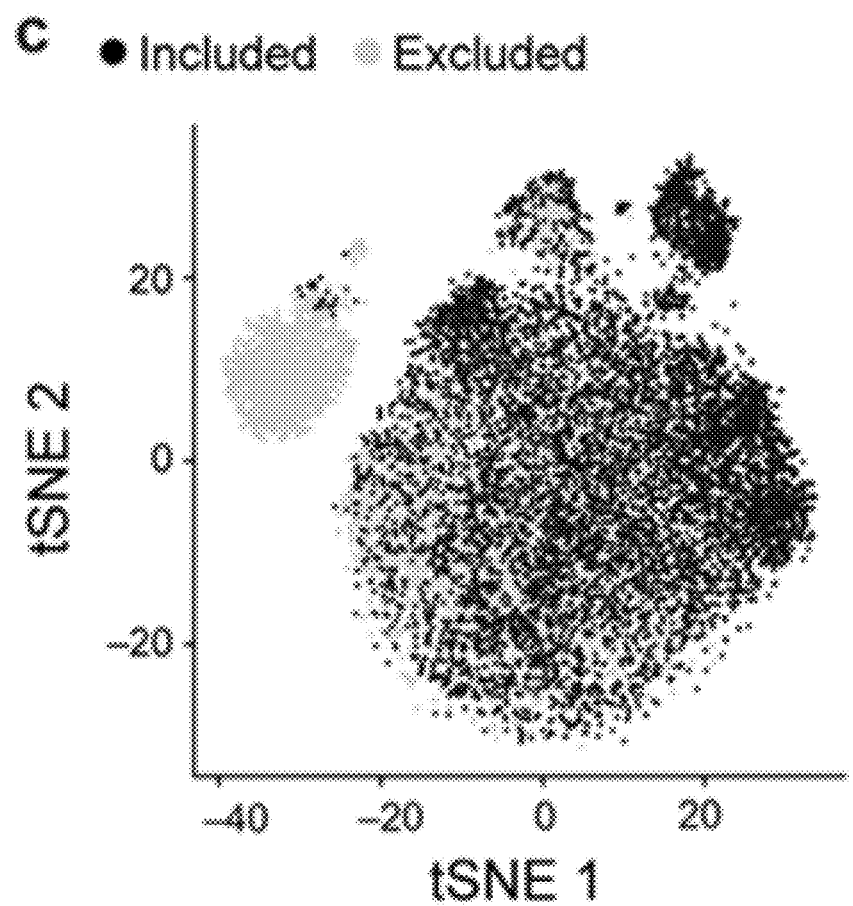

Applicants hypothesized that cells can transition between some of these programs or states, as such transitions would be consistent with the dense transcriptional continuum observed. Unlike pseudotime inference[46,47], topic modeling does not assume the existence of an "axis" of progression, which may not exist in settings such as the untreated condition. Moreover, when a trajectory does exist, it may be reflected only in specific aspects of the transcriptional profiles. Indeed, a temporal "induction" dimension in the data was revealed most clearly when Applicants focused on specific topics related to immune repression or activation. To identify transitional relationships in the context of the biological processes reflected by these topics, Applicants created a diffusion map only from those cells highly weighted for Topics 2, 4, 8, 11, 13 and 15, but not for Topics 6 or 7, and used only the most distinguishing genes for each topic as input (FIG. 7a-c, Methods).

Figure 3A:
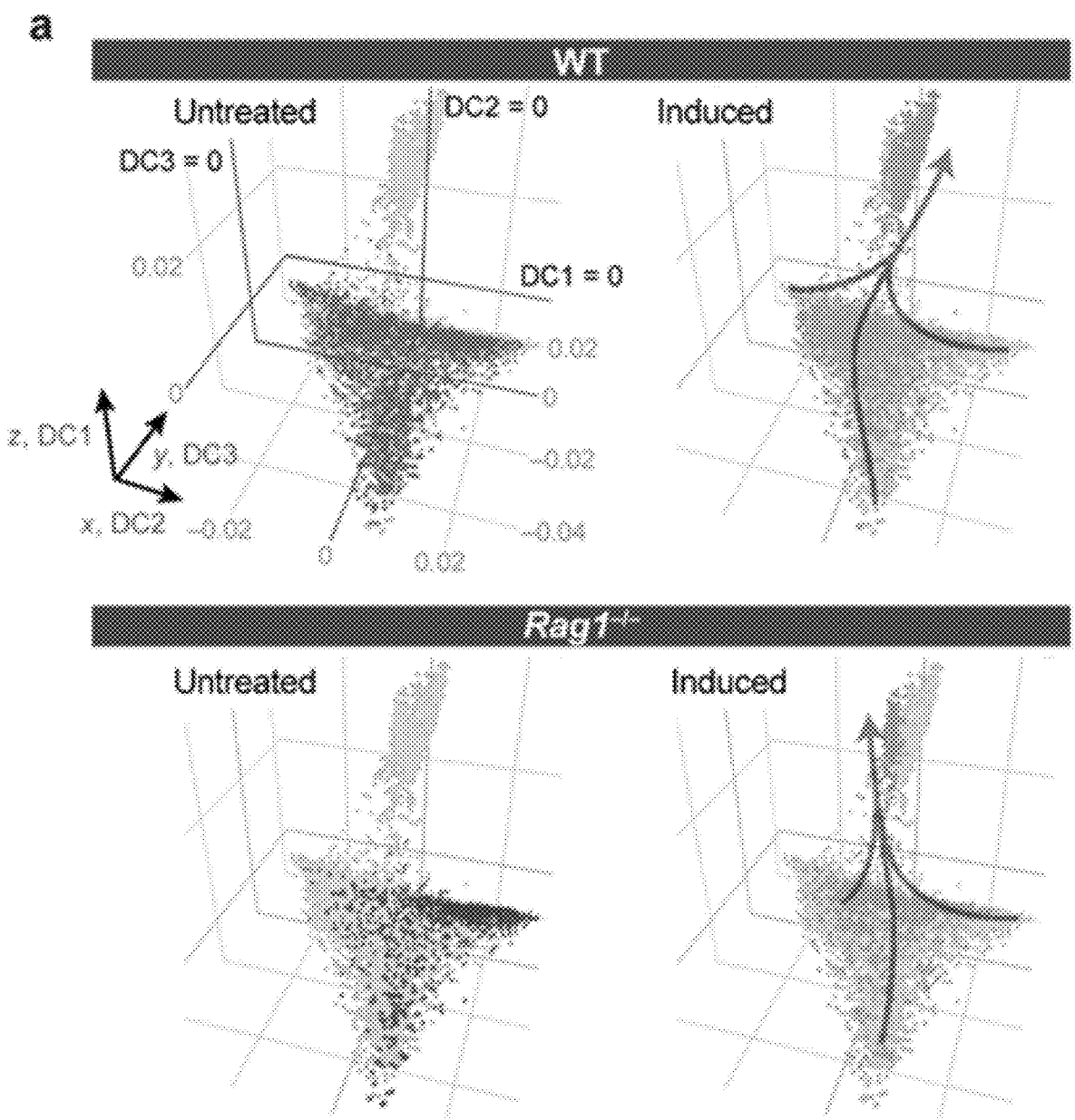
FIG. 3A-FIG. 3E—Inference of an IL-23-induced dynamic trajectory from quiescent-like ILCs through classically activated ILC2s to pathological Il13/Il17a/Il22-expressing ILC3-like cells.
Figure 3B:
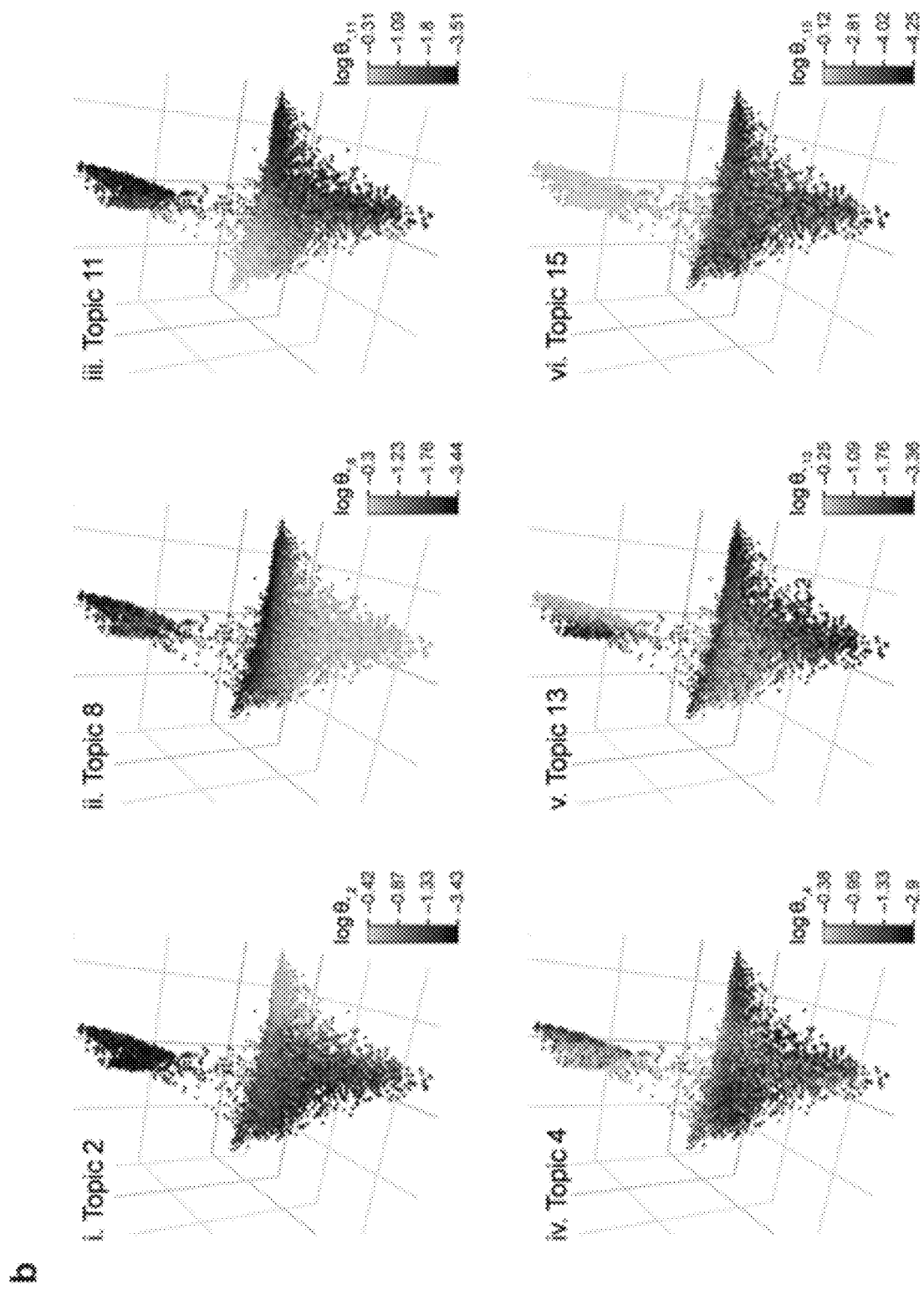
Figure 7D:
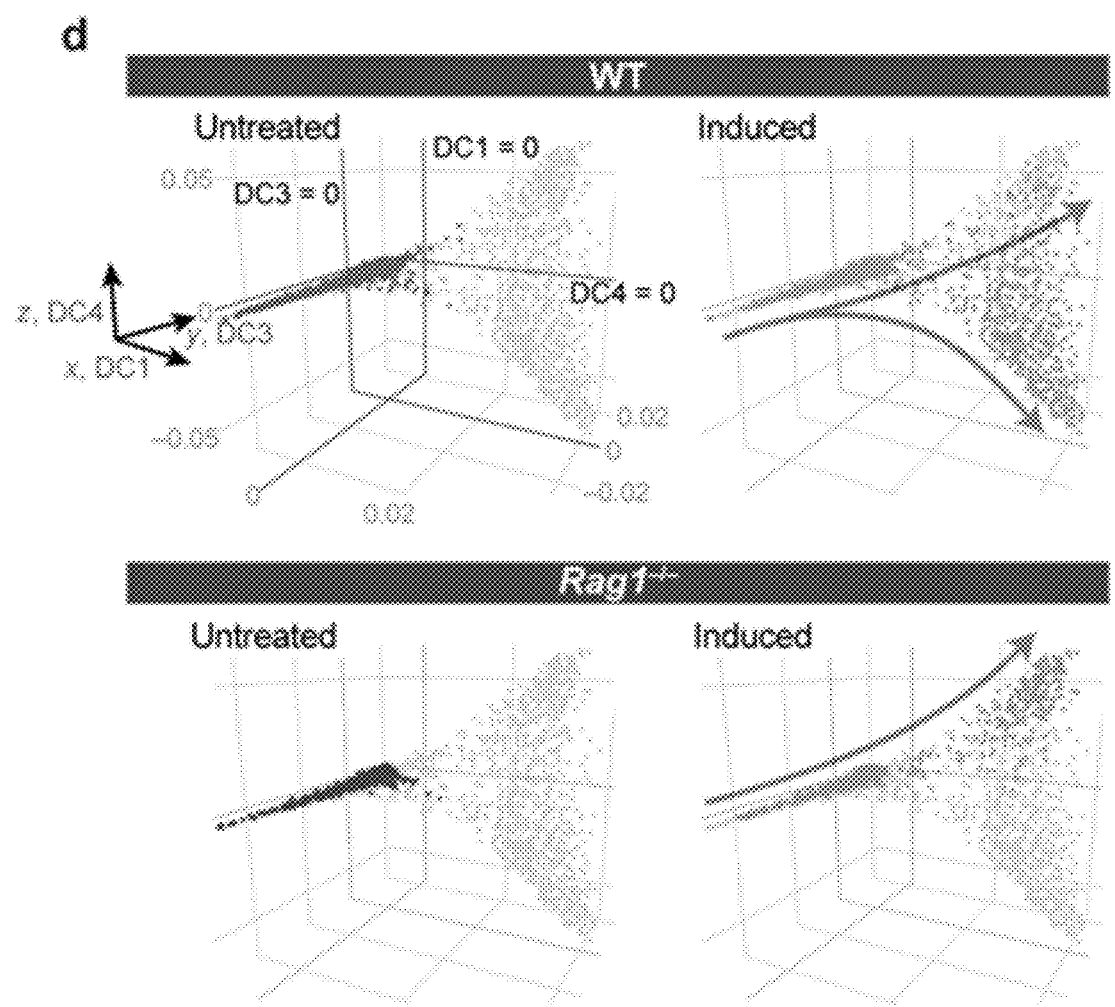
Figure 7E:
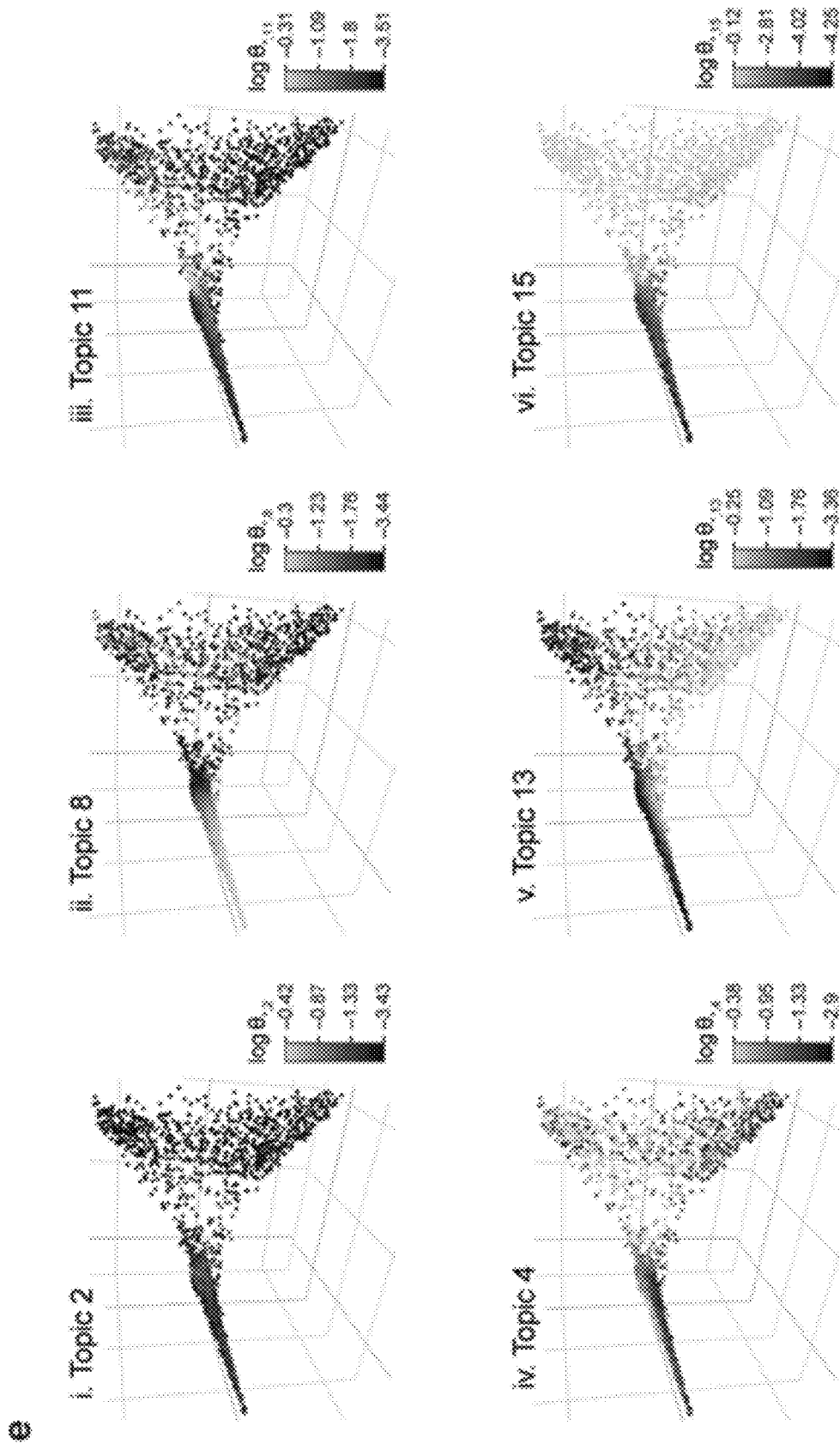

The diffusion map (FIG. 3a, FIG. 7d) proposes several parallel state transitions that cells undergo in the tissue, in particular highlighting a quiescence-ILC2-ILC3s state trajectory in the disease. First, cells from the naïve condition lie in a triangular region in the plane spanned by diffusion components (DC) 2 and 3 with corners up-weighted for Topic 2 ("resting"), 8 ("naïve-quiescent"), and 11 ("antigen presentation"), respectively (FIG. 3a,b.i-iii). Their distribution throughout the triangle suggests that in the untreated condition, cells range over all mixtures of these states. Second, DC1 captures the induced response shared in both WT and $Rag1^{-/-}$ mice (FIG. 3a, FIG. 7d), such that as their DC1 coordinate ("induction") increases, cells typically have relatively lower weights for Topics 2, 8, and 11 (FIG. 3b.i-iii, FIG. 7e.i-iii), and higher weights for Topic 15 ("Il22/Il117"), Topic 4 ("actin remodeling"), and, specifically for cells from WT mice, Topic 13 ("Il5/Cxcl2") (FIG. 3b.iv-vi, FIG. 7e.iv-vi). Genotype-specific differences in the induction response are further captured by DC4, such that cells from WT and $Rag1^{-/-}$ mice have increasingly different DC4 coordinates as DC1 coordinate increases (FIG. 7d).

Figure 3C:
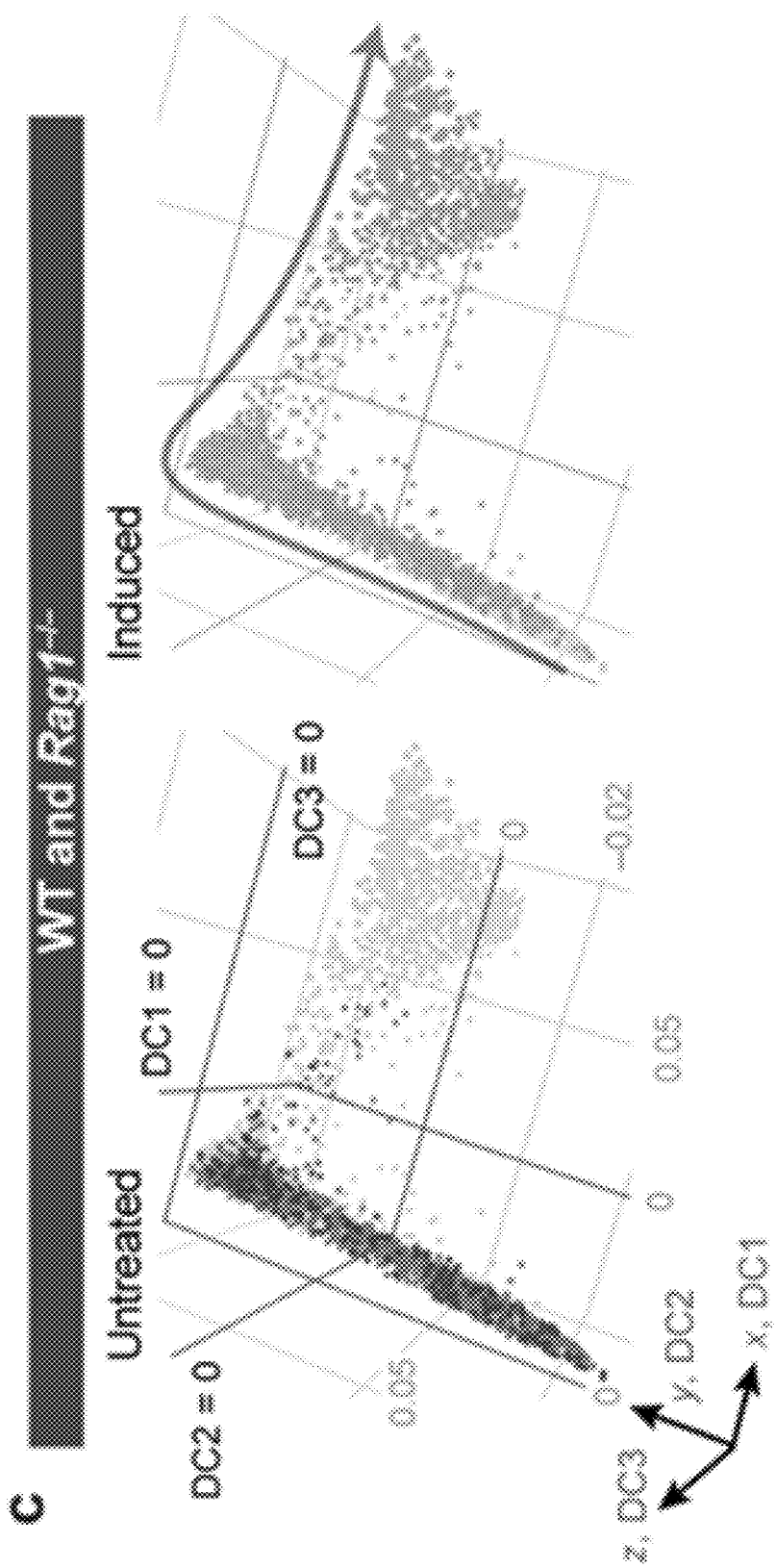
Figure 3D:
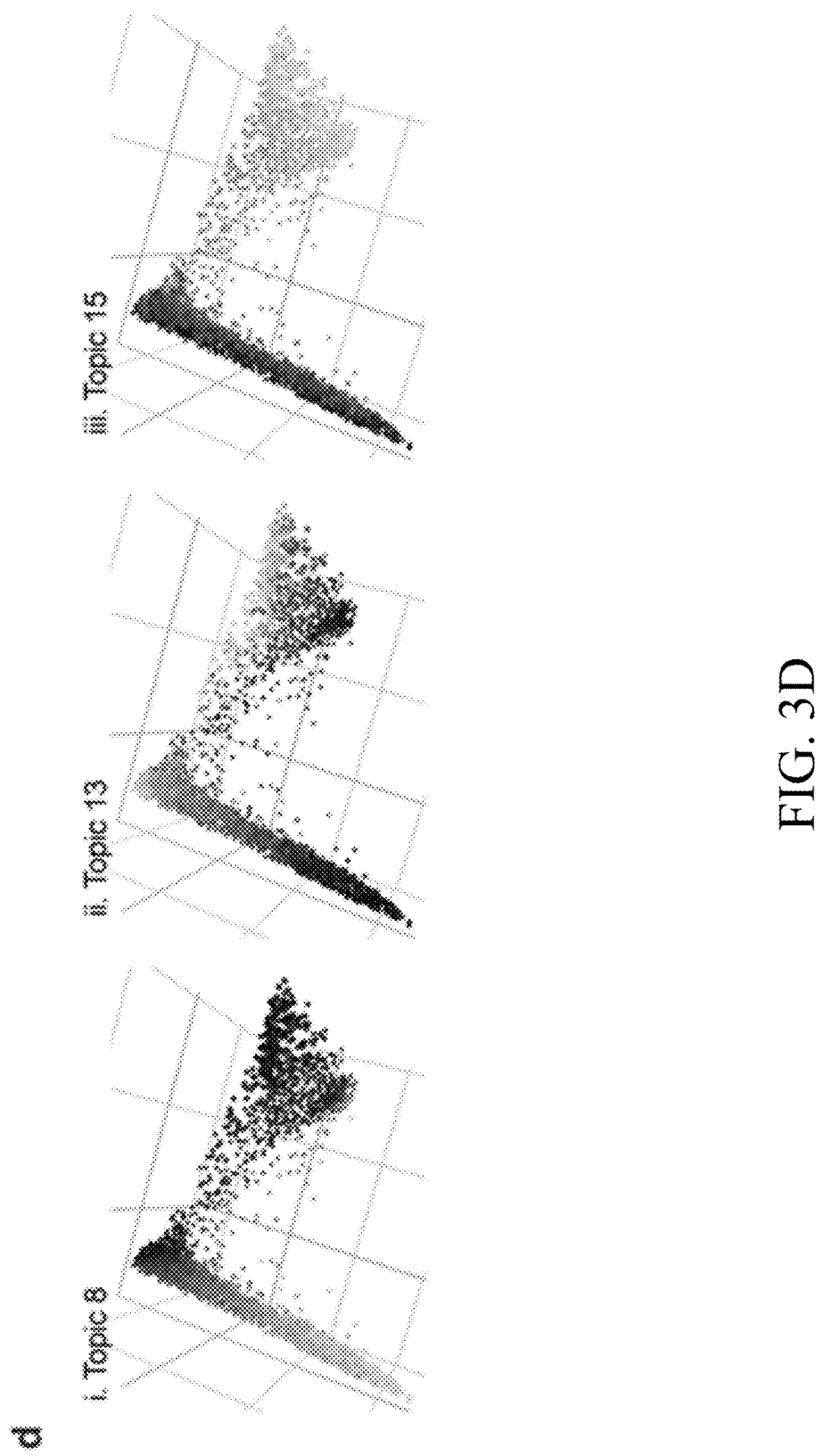
Figure 3E:
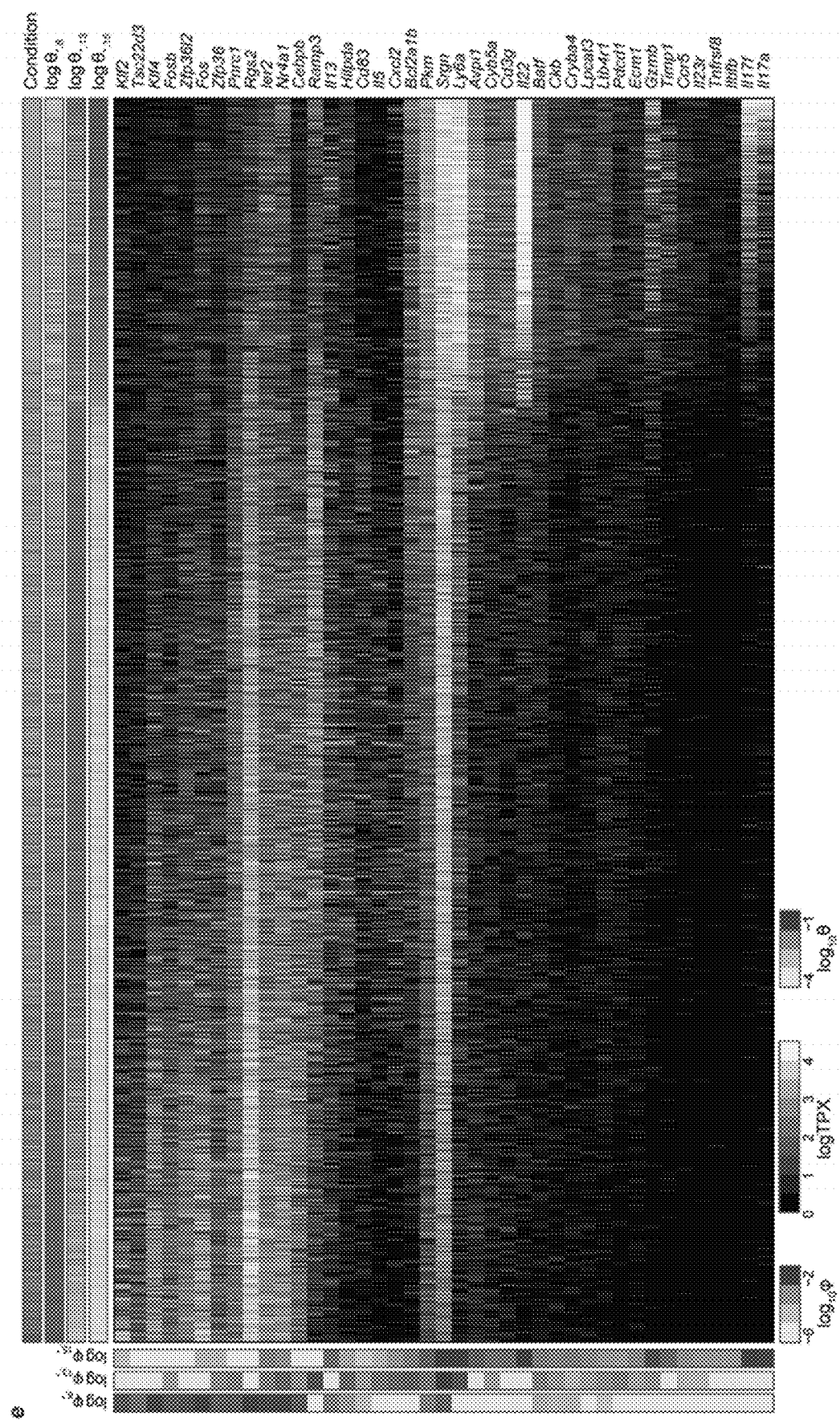
Figure 10A:
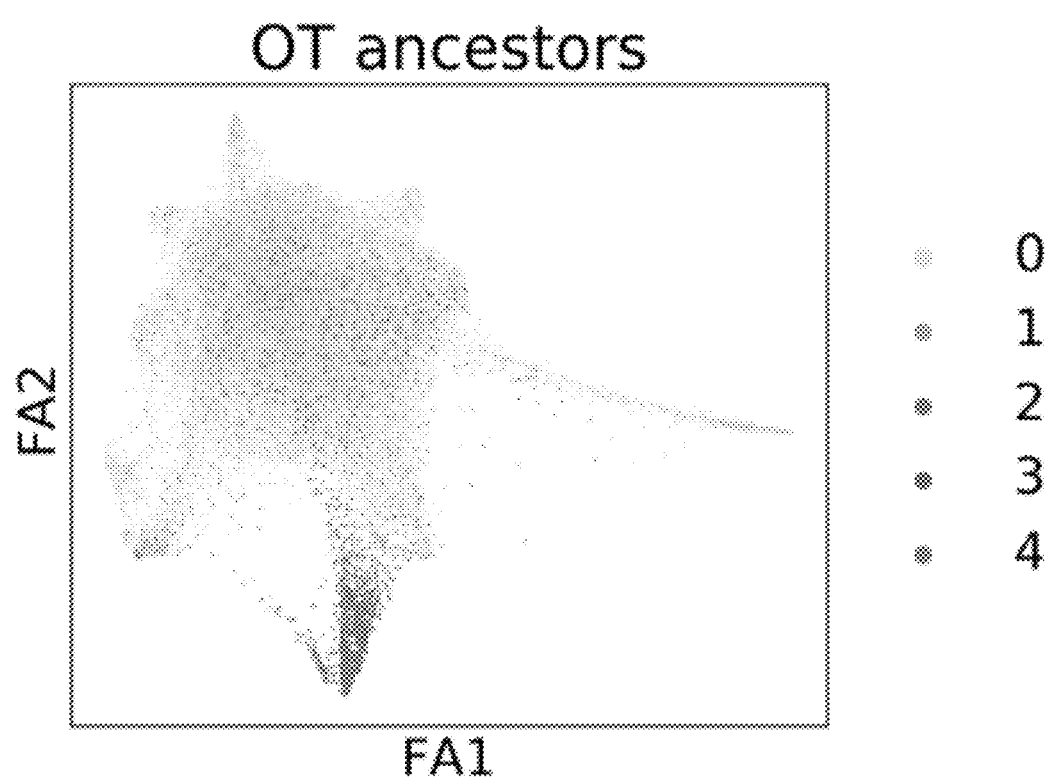
Figure 11A:
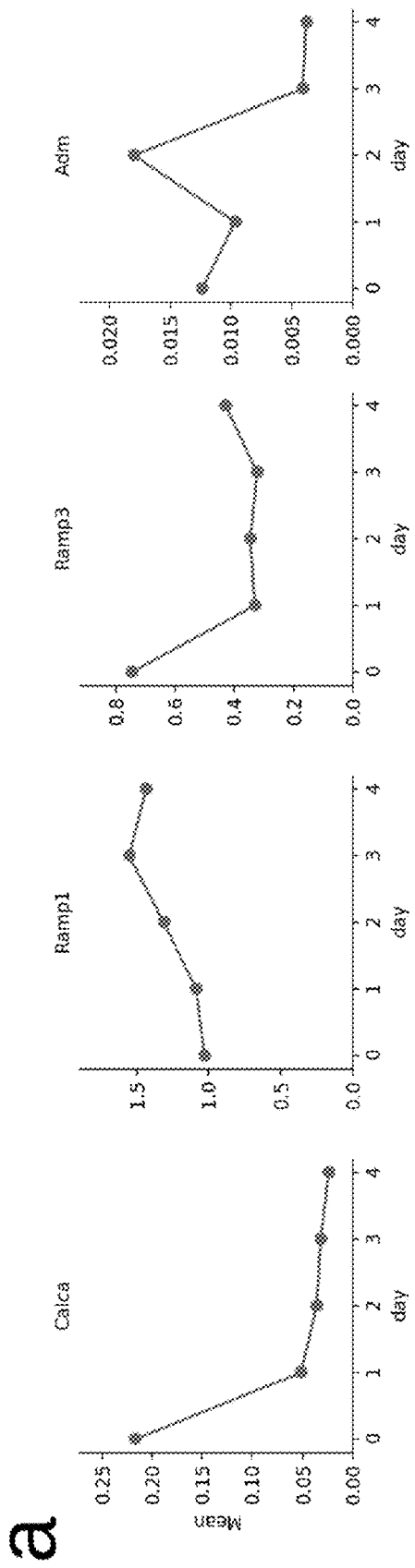
FIG. 11A-FIG. 11B—CGRP regulation in ILC3-like cells.
Figure 11B:
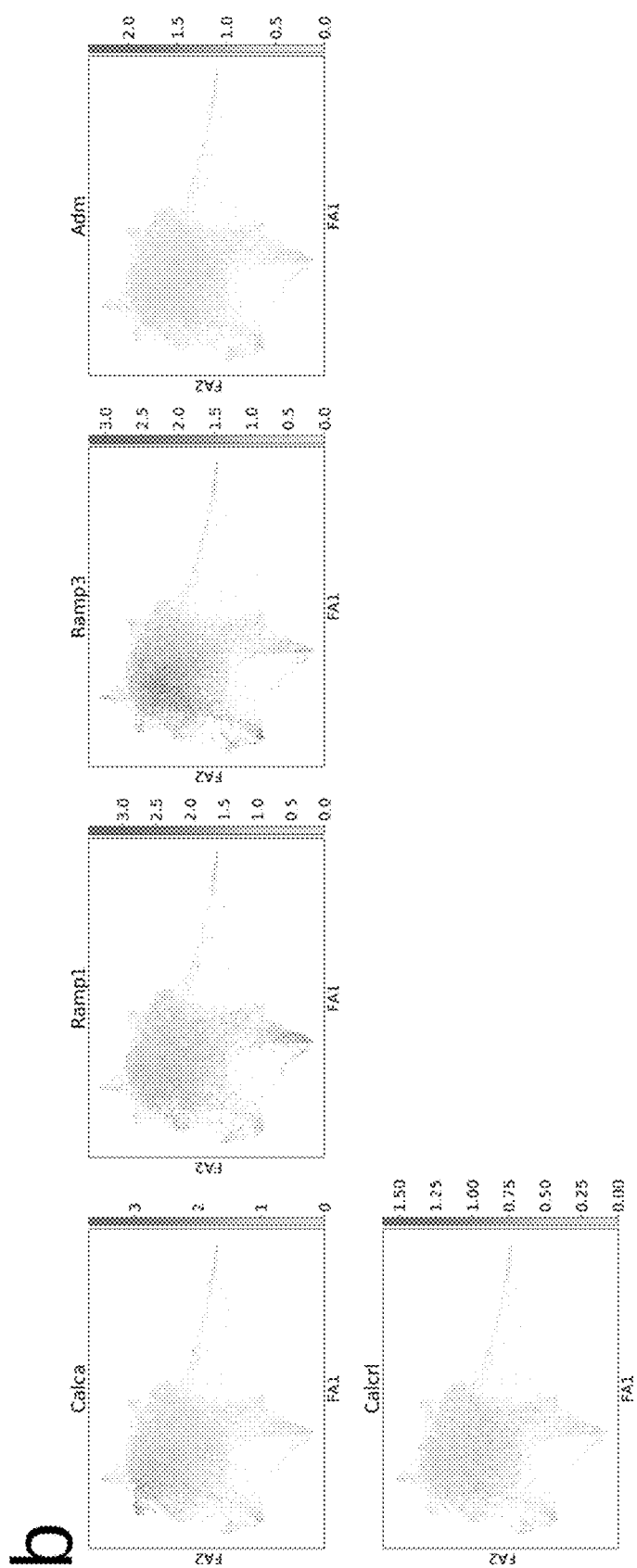

A focused diffusion map model (FIG. 3c) generated only from cells up-weighted for Topic 8, 13, or 15 (Methods), shows continuous expression changes from Topic 8 to 13 to 15, as DC1 (in this map) coordinate increases (FIG. 3d,e). Indeed, DC1 is particularly well correlated with expression of the gene Srgn, a proteoglycan that is critical for the trafficking and storage of Gzmb[48], which suggests that expression of this gene could be an early indicator of a trajectory toward type 3 activation, visible before expression of either Gzmb or type 3 cytokines (FIG. 3e). The expression changes observed across Topic 8, 13, and 15 are consistent with a novel model of immune activation in which a type 3 stimulus (IL-23) causes skin-resident naïve/quiescent ILCs to undergo type 2 activation, followed by transition to ILC3-like cells. See also, FIG. 10.

Figure 4A:
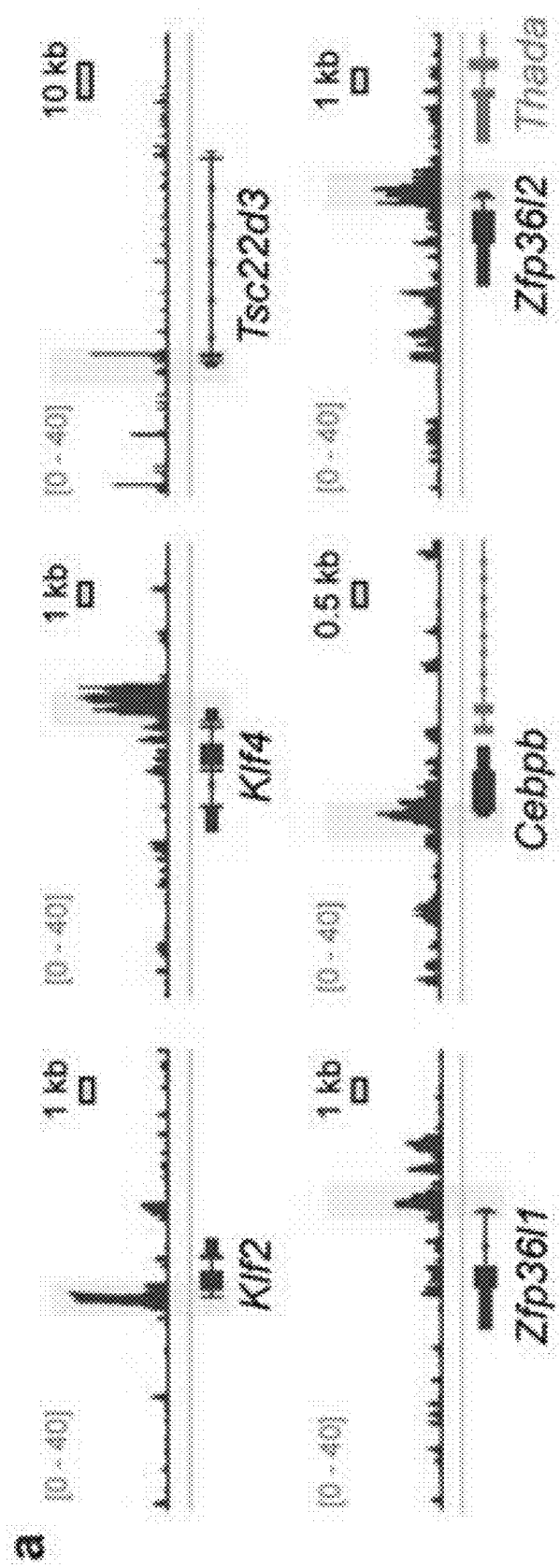

Finally, Applicants tested the model's predictions of a quiescent-ILC2-ILC3 trajectory. First, Applicants validated the quiescent state by ATAC-Seq of sorted total skin ILC populations from naïve mice. Consistent with Topic 8 ("naïve-quiescent") highlighted by the scRNA-seq analysis, the loci for the TFs Klf2, Klf4, previously associated with quiescence[36,37], Tsc22d3 and Zfp36l2, associated with Th17 genetic program repression[38-40] and Cebpb, involved in hematopoiesis[49], had open chromatin signatures at their TSS (FIG. 4a).

Figure 4B:
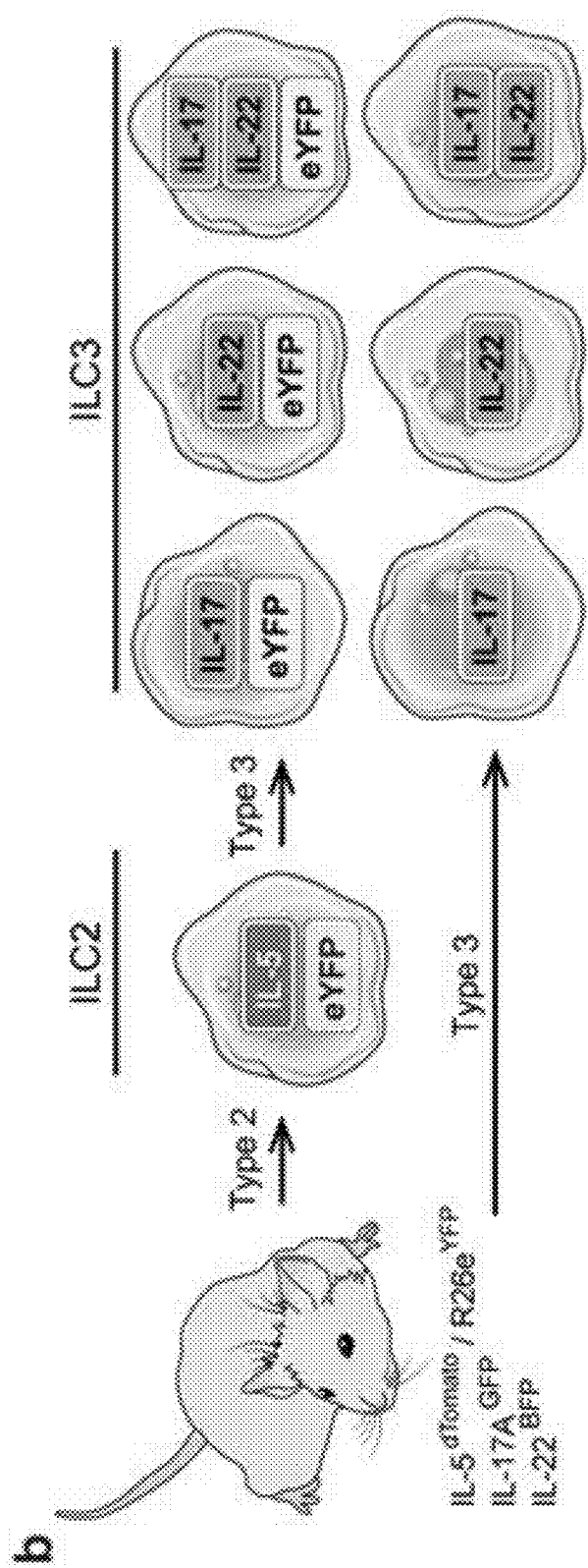
Figure 4C:
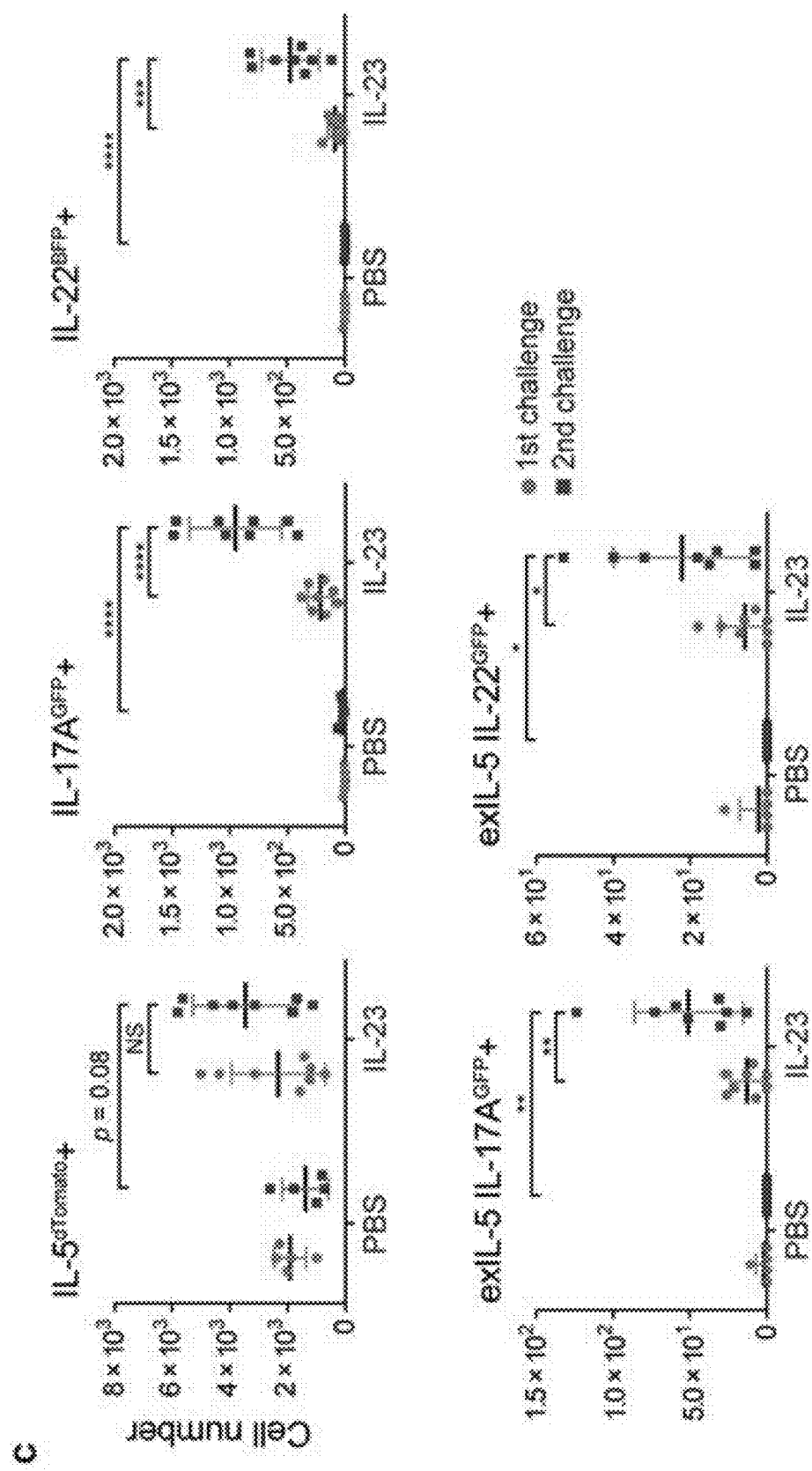
Figure 4D:
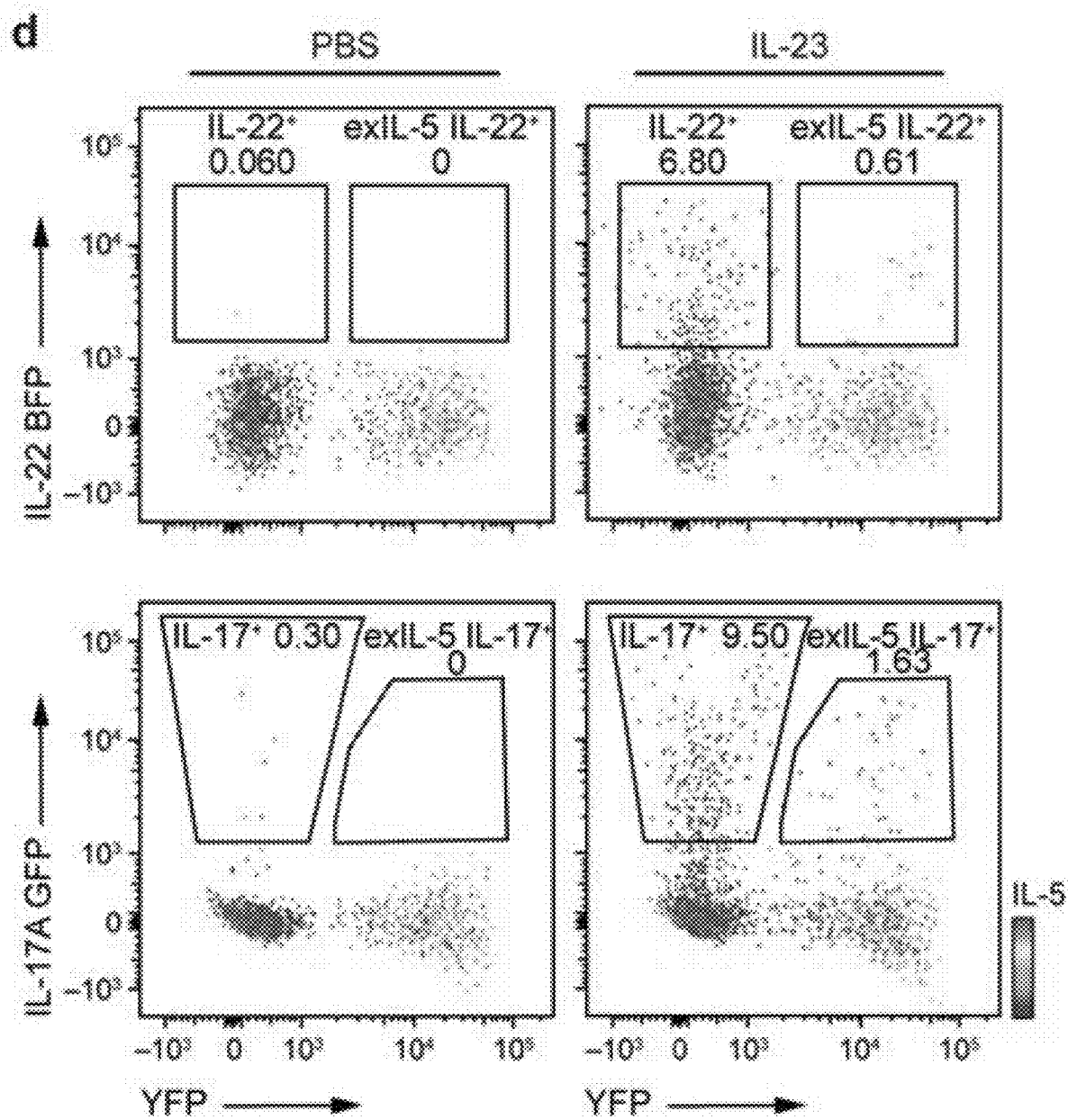
Figure 4G:
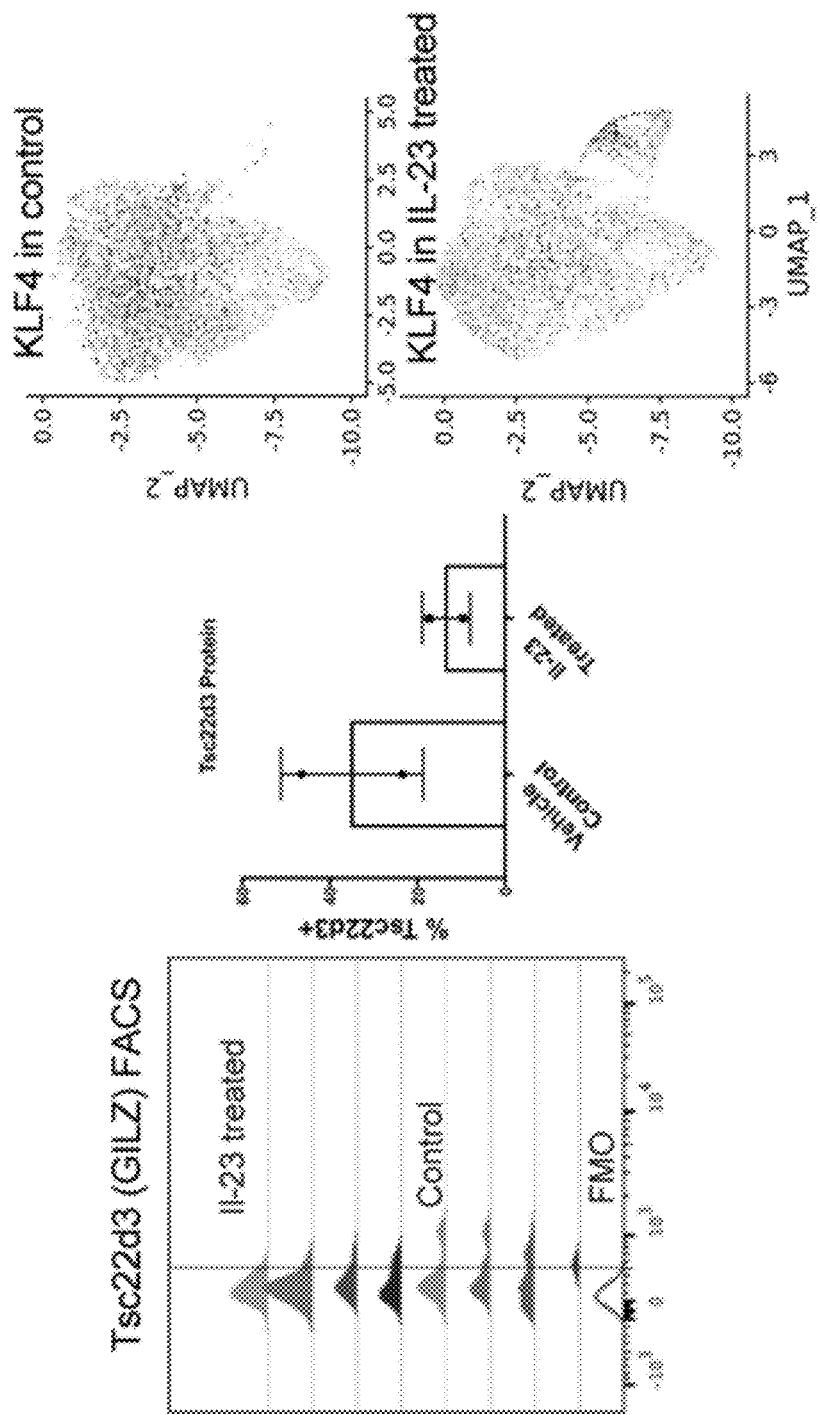
Figure 4H:
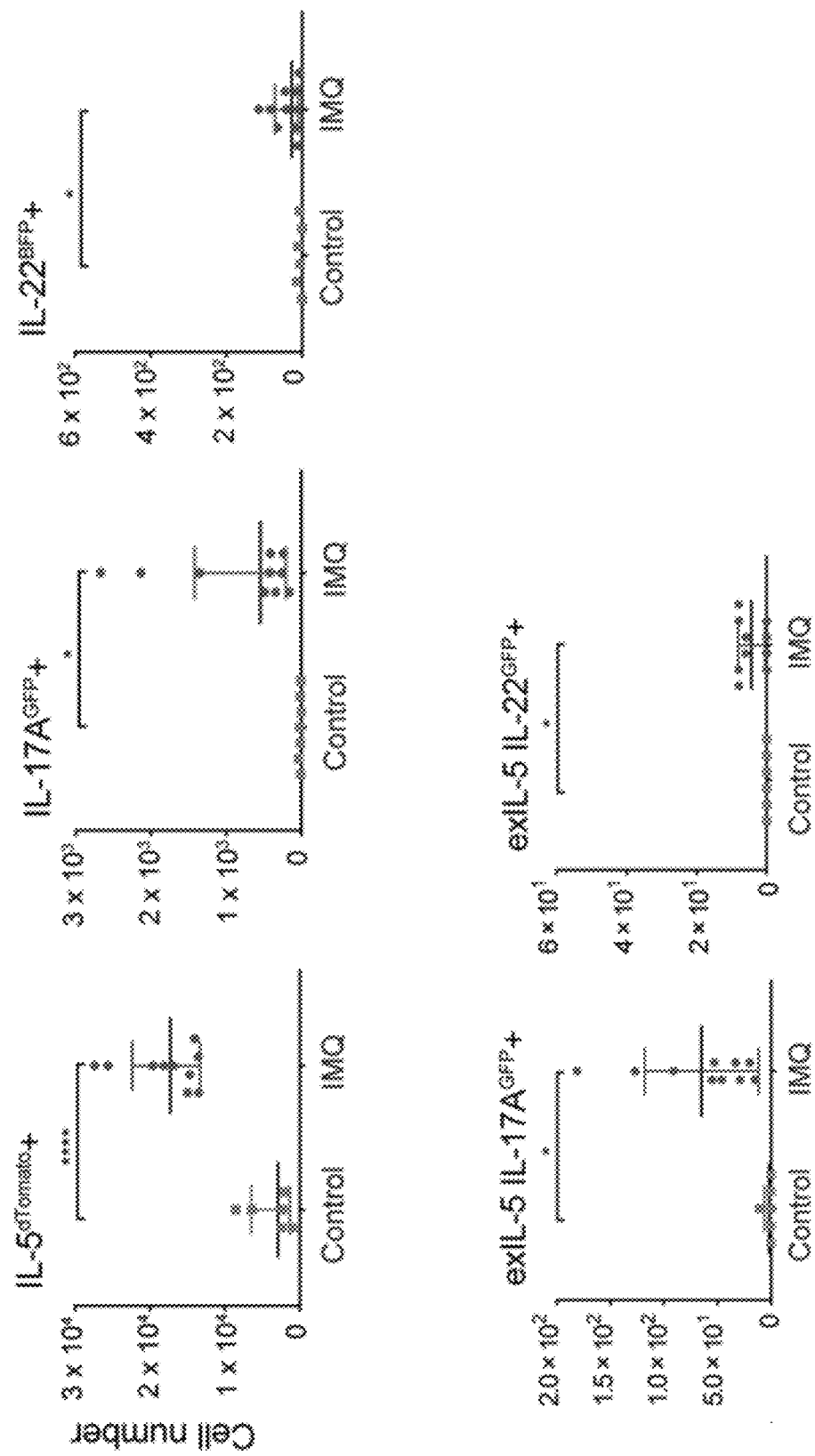
Figure 4I:
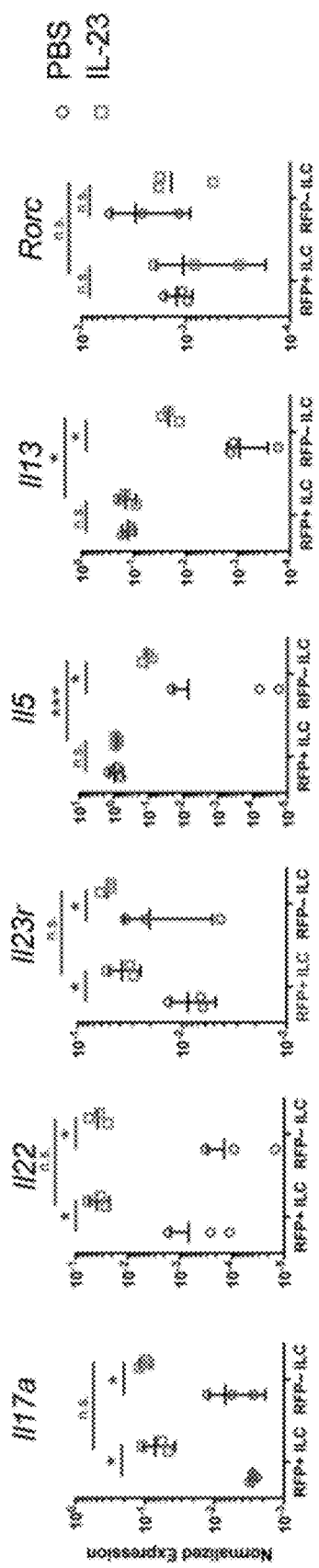

Next, Applicants tested the prediction of a transition during disease of IL-5-expressing ILC2s into IL-22/IL-17A-expressing ILC3-like cells. Applicants generated an IL-5 fate reporter mouse from IL-5-cre-dTomato (Red5)[50] and Rosa26$^{flox-Stop-floxYFP}$, which Applicants then combined with IL-17A$^{GFP}$ [51] and IL-22$^{BFP}$ expression reporters (FIG. 4b). Consistent with the model, after IL-23 injection, ~10% of the IL-22- and IL-17A-expressing cells were indeed ex-IL-5 producing cells, as measured by fate mapping of ILC2s, and a second IL-23 challenge further elevated the number of ex-IL-5 cells producing IL-22 and IL-17A (FIG. 4c,d). Moreover, cells that expressed ILC3 type cytokines no longer expressed IL-5 (FIG. 4d). The results show the in vivo potential for plasticity among skin ILCs and demonstrates that some cells expressing ILC3 type cytokines expressed IL-5 at one stage of their lifetime. Finally, Applicants also tested the model's prediction that there is a subset of skin ILCs in the psoriasis model that co-expresses the type 2 cytokine IL-13 with both of the type 3 cytokines IL-22 and IL-17A. Indeed, intracellular measurements of these three cytokines showed that, consistent with the predictions, nearly 20% in Rag1$^{-/-}$ and 10% in WT and Tcrd$^{-/-}$ of cells expressing IL-22 and IL-17A also co-express IL-13 (FIG. 4e,f).

In conclusion, experimentally combining scRNA-seq, ATAC-seq, and in vivo fate mapping in the psoriasis mouse model with new analytical approaches, Applicants showed the presence of previously undescribed naïve/quiescent-like tissue-resident ILCs and the ability of activated ILC2s to differentiate to pathological ILC3s. Applicants further discovered a novel subset of ILCs expressing IL-13 and IL-22/IL-17A in response to IL-23 stimulation. The work highlights the limitation of experimental and computational analyses of immune cells that treat them as discrete immune "types", when immune cells may share biological signals and span continuous spectra. In the system, Applicants did not observe any discrete boundaries in single-cell expression profiles that neatly partitioned naïve/quiescent-like ILCs from activated type 2 cells, or type 2 cells from type 3 cells. Rather, the entire population of skin-resident ILCs was functionally reconfigured and its spectrum shifted by disease induction. Indeed, imposing stress on an immune cell population may allow rapid shifting of such a spectrum towards alternative cell fates[52], and pathways similar to those Applicants uncovered in the skin may play roles in other tissues. Importantly, this also suggests that studies of ILCs sorted on expression of specific cytokines, such as IL-5[44], may not have fully assessed this larger continuum. This model substantially revises previous interpretations and can provide a unified framework for some observations in other systems, such as "functional compartmentalization" within ILC types and gut ILCs that could not be readily assigned to a single ILC type[35]. These studies did not report a differentiation from ILC2 to ILC3, (but rather reported that a core ILC2 module was robust to antibiotic perturbation, albeit with increased expression of genes associated in homeostasis with ILC3s[35], which may reflect tissue-specific differences in ILC features[44]. Computational models and biological interpretations that allow for such fluidity, including topic modeling, are thus valuable for uncovering biological phenomena because they highlight signals such as, in this case, type 2 activation, shared by cells in distinct clusters, and reveal drivers of heterogeneity among cells within a single group, such as the ILC "cloud". This type of presentation is consistent with recent studies of HSCs, where individual precursors have probabilistic fate maps, tilted towards but not committed to specific outcomes[53,54]. Such approaches should be valuable in uncovering how tissue-resident ILCs, and other cell types, may globally respond to a stimulus and undergo dynamic, plastic activation to reach the necessary state for shaping the tissue landscape.

Example 2—Methods

Mice. C57BL/6, Tcrd$^{-/-}$ and Rosa26$^{flox-stop-floxYFP}$ Ai3 (RCL-EYFP) mice were purchased from the Jackson Laboratories. Rag1$^{-/-}$ and Rag2$^{-/-}$IL2rg$^{-/-}$ were purchased from Taconic Biosciences. IL-5 Cre, dTomato (Red5/R5) from Dr Locksley laboratory. The IL-5 fate reporter in this work was generated by crossing Red5 with Ai3(RCL-EYFP) with IL-17A$^{GFP}$ [51] and IL-22$^{BFP}$ generated in Applicants laboratory. In order to maximize the Cre recombination and increase the signal of Rosa26$^{YFP}$ positive cells, Applicants used homozygous IL-5$^{dTomato, Cre}$. Applicants observed little to no difference in IL-23 induced skin thickening (FIG. 8a).

All mice were kept under specific pathogen-free (SPF) conditions in the animal facility at Yale University. Age- and sex-matched littermates between 10 to 14 weeks of age were used for all experiments. Unless with special instructions, mice were randomly assigned to different experimental groups and each cage contained animals of all different experimental groups. Both male and female mice were used in experiments. Animal procedures were approved by the Institutional Animal Care and Use Committee (IACUC) of Yale University. Preliminary experiments were tested to determine sample sizes, taking available recourses and ethical use into account.

Psoriasis model. The psoriasis model used in this study is based on rIL-23 subcutaneous injections. The 500 ng in 20 µl of rIL-23 (provided by Abbvie or purchased from R&D Systems [scRNAseq experiments]) was injected daily into the ear skin of anesthetized mice in 4 consecutive days. As a control 20 µl of PBS was used with the same injection intervals. For the second challenge experiment, Applicants waited 10 days, monitoring the skin thickness before repeating 4-day injection regimen. Skin thickness was measured daily with calipers. When indicated, FTY720 (1 mg/kg) was dissolved in PBS and administered i.p on day −1, 1 and 3 of the experiment. Skin tissue was collected on day 5 for histology imaging, flow cytometry analysis or cell sorting.

Isolation of skin lymphocytes. Ventral and dorsal dermal sheets of ears were separated, minced and incubated in RPMI medium containing 0.4 mg ml$^{-1}$ Liberase™ (Roche Diagnostics) and 60 ng/µl DNAseI (Sigma). After digestion, the suspension was passed through and further mechanically disrupted with syringe plunger and a 70 µM cell strainer. Lymphocytes were enriched by gradient centrifugation in 27.5% Optiprep solution (Sigma) and RPMI medium containing 5% Fetal Bovine Serum. Spleens were mechanically disrupted using a syringe plunger in complete RPMI. Cells were filtered through 70-µm nylon mesh and washed.

Flow cytometry and cell sorting. Mouse ILCs were stained with monoclonal antibodies to CD45.2, CD90.2, lineage (CD4, CD8, CD11b, CD11c, CD19, B220, NK1.1, Ter119, Gr1, FcEr1a), TCRβ, TCRγ, CD3ε. For intracellular cytokine staining, cells were re-stimulated for 6 h at 37° C. with phorbol 12-myristate 13-acetate (PMA) (Sigma, 50 ng ml$^{-1}$) and ionomycin (Sigma, 1 µg ml$^{-1}$) in the presence of Golgistop (BD Bioscience) added after initial 2 h of stimulation. Next, cells were fixed and stained with BS Cytofix/Cytoperm reagent (BD Biosciences) according to the manufacturer's protocol. Intracellular cytokines were stained with antibodies to IL-13, IL-17A and IL-22. Total ILCs were sorted as live, CD45+, CD90+, lin-(CD4, CD8, CD11b, CD11c, CD19, B220, NK1.1, Ter119, Gr1, FcEr1a), CD3E- and TCRγ/δ– cells into PBS/0.2% FBS.

In-vitro ILC cultures. For in vitro experiments, 5,000 ILCs were cultured per well of a 96-well round bottom plate in Click's medium with 10 ng ml$^{-1}$ IL-2 (R&D Systems) and 25 ng ml$^{-1}$ IL-25 (R&D Systems) with 10 ng ml$^{-1}$, IL-33 (R&D Systems) or IL-23 25 ng ml$^{1}$ (provided by Abbvie) with TGFβ 10 ng ml$^{-1}$ (R&D Systems) and IL-1β 10 ng ml$^{-1}$ (R&D Systems). Cells were collected for RNA extraction and qRT-PCR after 5 days of culture in 37 ÆC and 5% $CO^2$.

Adoptive ILC transfer. Total skin ILCs were FACS purified and collected to PBS 5% serum. Cells were washed twice with 1×PBS and injected (10,000 cells per mouse in 100 μl) into retro-orbital vein of anesthetized Rag2$^{-/-}$ IL2rg$^{-/-}$ mice. IL-23 injection experiments were performed 14 days after the transfer.

RNA extraction and Quantitative Real time PCR (qRT-PCR). RNA from in vitro cultures was isolated with RNeasy Mini Kit (QIAGEN) and qPCR was performed using KAPA Probe Fast qPCR Master Mix 2× Kit (Kapa Biosystems, Wilmington, MA) with TaqMan probes (Applied Biosystems) in a StepOne cycler (Applied Biosystems, Carlsbad, CA). The CT values from duplicate qPCR reactions were extracted from the StepOne cycler (Applied Biosystems, Carlsbad, CA) onto Excel spreadsheets and were analysed with the relative quantification method $2^{\Delta\Delta CT}$.

ATAC-seq. Total ILCs sorted from naïve wild type mice were processed for ATAC-seq analysis according to previously published protocol[55] with the low cell number input version (~5,000 ILCs). Libraries from two independent experiments were sequenced on HiSeq2500 with 75 bp paired end reads. Each sample was sequenced to a depth of 150 million reads.

ATAC-Seq data analysis. Adapter sequences were trimmed using FASTX-Toolkit (version 0.0.13, hannonlab.cshl.edu/fastx_toolkit/), after which Bowtie2[56] was used to align the reads to the mm10 genome. Picard tools (version 2.9.0, broadinstitute.github.io/picard/) were used to remove PCR duplicates. Bedtools was used to convert the bam file to a bed file, and all mapped reads were offset by +4 bp for the positive strand and −5 bp for the negative strand. Peaks were called for each sample using macs2[57] using parameters—nomodel—nolambda—shiftsize 75. ATAC-seq peaks were visualized with the Integrative Genomics Viewer[58,59] along with publicly available ChIP-seq via Cistrome DB[60].

Single cell RNA-Seq. Sorted cells were washed with PBS/0.04% BSA and processed for droplet-based 3' end massively parallel scRNA-seq: sorted ILCs were encapsulated into droplets, and libraries were prepared using Chromium Single Cell 3' Reagent Kits v2 according to the manufacturer's protocol (10× Genomics). scRNA-seq libraries were sequenced using a 75 cycle Nextseq 500 high output V2 kit.

Single Cell RNA-Seq Data Analysis.

Initial data processing and QC. Gene counts were obtained by aligning reads to the mm10 genome using CellRanger software (v1.3) (10× Genomics).

To remove doublets and poor-quality cells, cells were excluded from subsequent analysis if they were outliers in their sample of origin in terms of number of genes or number of unique molecular identifiers (UMIs), which eliminated 5.8-7.9% of cells per sample (FIG. 8b), or outliers across all samples in percentage of mitochondrial genes, which eliminated at most 0.5% of remaining cells (FIG. 8c). Sample-specific cut-offs ranged from 575-2,400 genes per cell for the Rag1$^{-/-}$ untreated sample to 850-3,100 genes per cell for the WT induced sample.

Normalization. To normalize gene counts, Applicants used a scaling factor that reflected the expected number of UMIs in each sample (FIG. 8d), rather than scaling all cells to a constant size, as in TPM[34] Let $w_s$ be the mean number of UMIs per cell in sample s. UMI counts for cells in sample s were scaled to: 10,000× ($w_s/w_{WT\ naive}$). Taking the log of scaled UMI counts gives the normalized expression values referred to as log TPX.

Figure 8E:
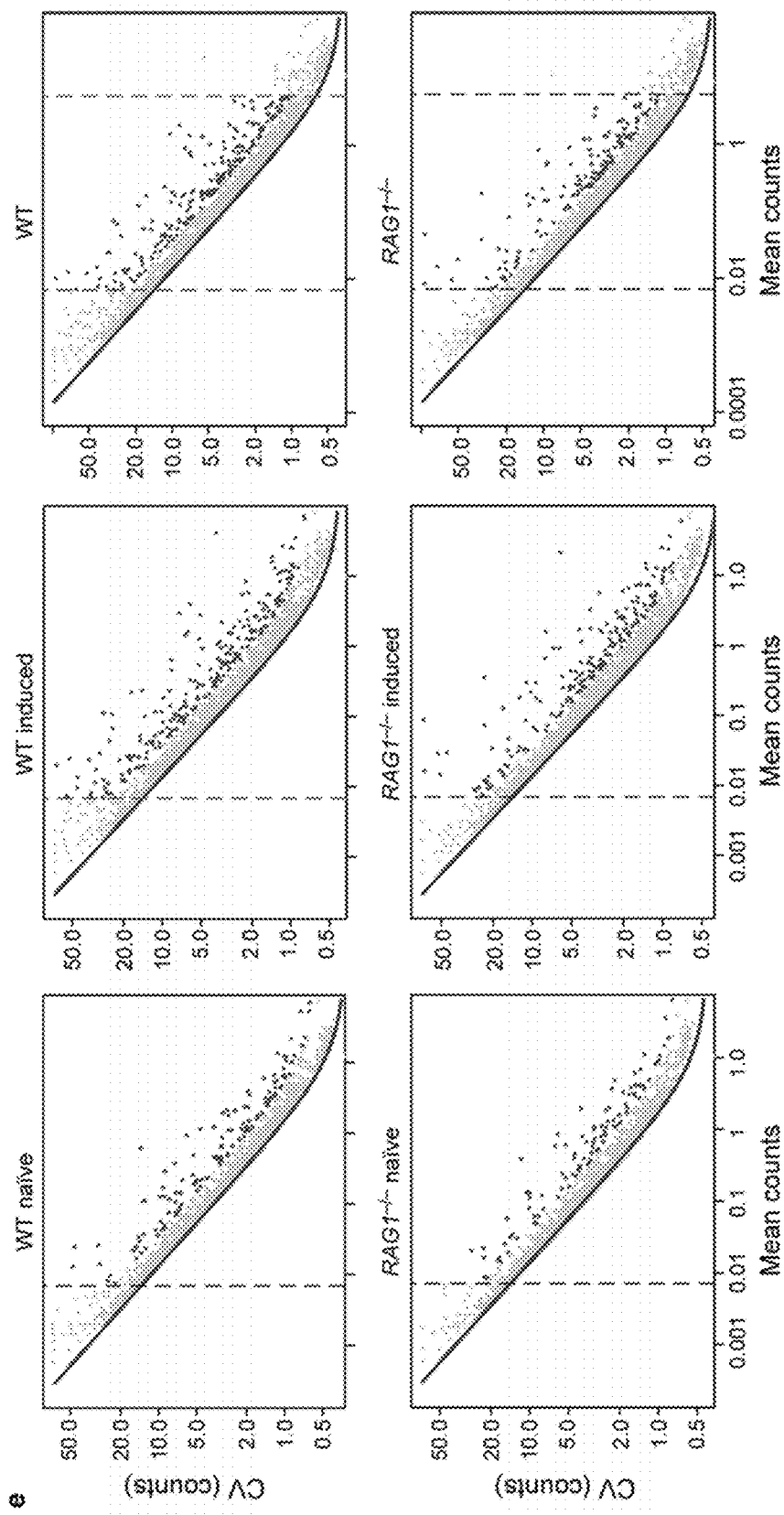
Figure 8F:
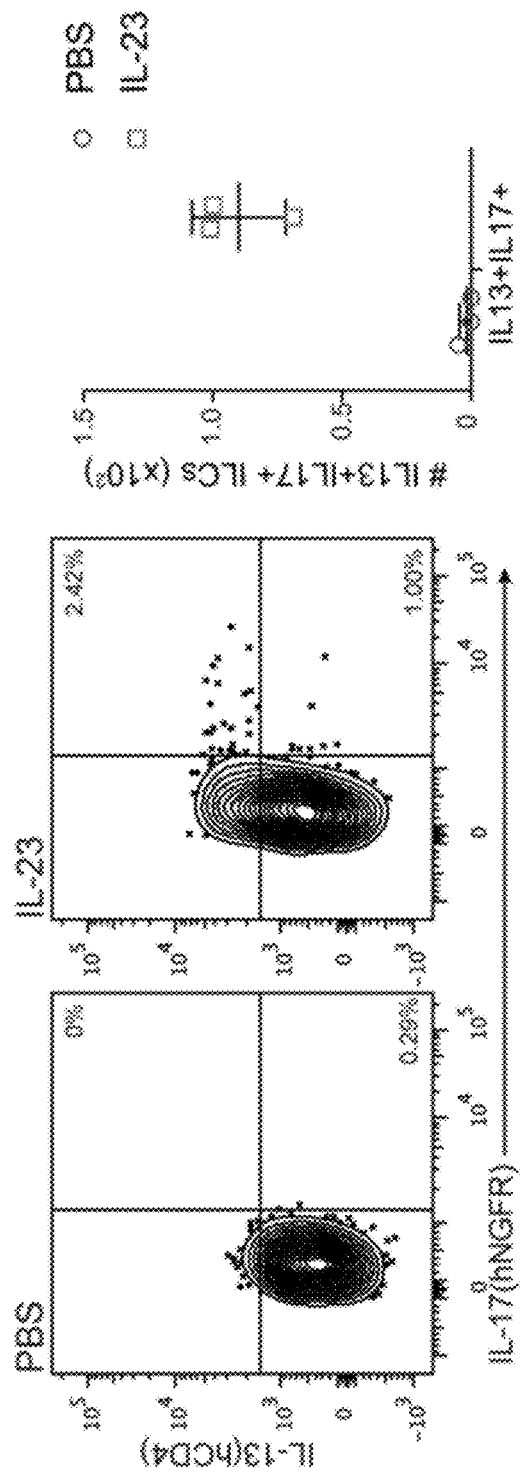
Figure 8G:
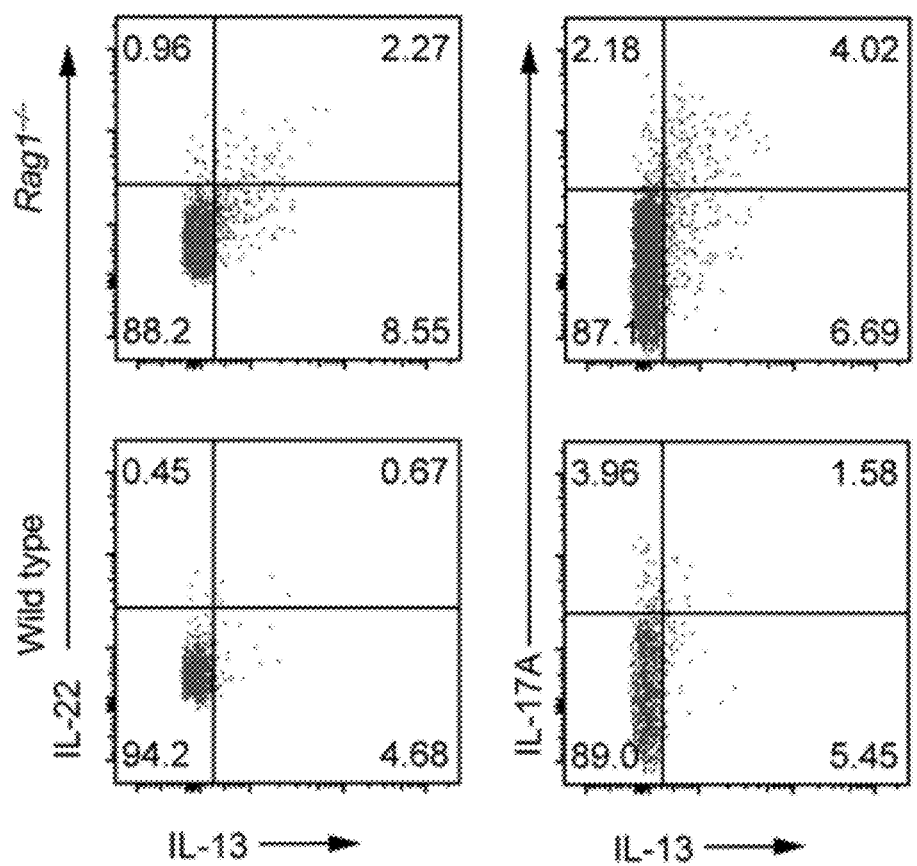
Figure 9A:
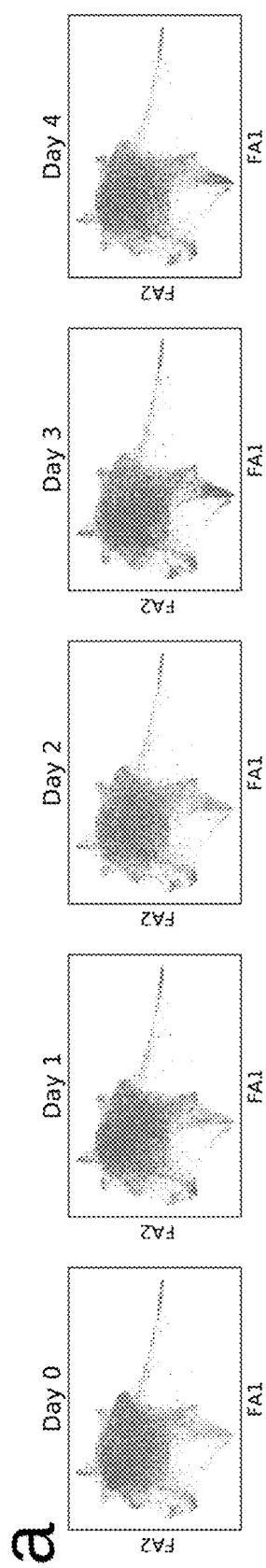

Determination of variable genes. Applicants fit the count data to a null model based on a negative binomial distribution that explains the expected technical variation for each gene, given its expression level, as previously described[61]. A gene was considered to exhibit non-technical variability if it had mean counts above 0.005 and a coefficient of variation at least log(0.5) times that predicted by the null model (FIG. 8e). Applicants performed variable gene selection separately for each sample as well as for pooled samples from WT mice and, separately, from Rag1$^{-/-}$ mice. To reduce downstream technical effects of the variation in extremely highly expressing genes, Applicants then removed any genes that had mean counts above 4 in WT or, separately, Rag1$^{-/-}$ cells (these were mostly ribosomal protein genes). The resulting conservative set of 271 genes was then used for the singular value decomposition (SVD). Applicants chose this approach to ensure that noisy variable gene selection was not a cause of the heterogeneity in the "cloud". Note that downstream results were qualitatively similar and robust to several parameter settings, which yield variable gene sets of very different sizes, as well as to other selection approaches (including the FindVariableGenes( ) function in Seurat)[62].

Dimensionality reduction, clustering, and visualization. Applicants computed an SVD on z-scored variable genes, as determined above, using Seurat's RunPCA( ) function, with the "weight.by.var" parameter set to FALSE[62]. Assessing the decrease in marginal proportion of variance explained with larger components, Applicants selected the top 18 eigenvectors for subsequent analysis, and confirmed that the resulting analyses were not sensitive to this exact choice. Applicants used these components with Seurat's FindClusters( ) and RunTSNE( ) functions, with other parameter settings set to default, to cluster the cells, and to separately create a t-stochastic neighborhood embedding (tSNE) for visualization, respectively. As previously described, FindClusters( ) optimizes a modularity function on a k-nearest-neighbor graph computed from the top eigenvectors.

Removal of non-ILC clusters. Based on expression of marker genes across clusters, Applicants determined that a few very distinct clusters were unlikely to be ILCs: cells in those clusters had little expression of Ptprc (CD45), and high expression of Col1a2, or Tie1 and Pecam1, or Krt15. Cells from these non-ILC clusters were removed, and the steps of normalizing the data, selecting variable genes, performing PCA, and creating a tSNE were repeated as before, but the top 20 components of the SVD were used for subsequent analysis. After these steps, 18,852 cell profiles remained, with 4,619-4,857 cells per sample.

Topic modeling. Applicants fit an LDA topic model on the full, sparse counts matrix (18,852 cells and 27,998 genes) using the FitGoM( ) function from the CountClust R package[33], with the number of clusters K set to 15 and the "tol" tolerance parameter set to 10. This package is heavily based on the maptpx R package, which implements a posterior maximization approach to fitting the model[63]. Some approaches to selecting an appropriate value of K rely on having labeled training data for the model. Since Applicants do not have such a model, Applicants fit the model for a range of values and computed the Akaike and Bayesian information criteria (AIC and BIC) using the estimated likelihood returned by FitGoM((FIG. 6a). Since AIC and BIC risk under- and over-penalizing the fit, respectively, Applicants selected a value of K at a point where the AIC curve had begun to decrease less steeply and the BIC curve had begun to climb.

Diffusion maps. To select cells and genes for the construction of diffusion maps, a cell was considered "highly weighted" for a topic if its weight for the topic was above a topic-specific threshold capturing the upper tail of the distribution (FIG. 7a,b). The analysis is not sensitive to the exact choice of threshold. Cells were used in the large diffusion map (FIG. 3a) if they were highly weighted for any of topics 2, 4, 8, 11, 13, or 15, but not 6 or 7 (FIG. 7b,c). A gene was considered to be in the "top n genes" for a topic if it was returned by the CountClust function ExtractTopFeatures( ), which selects genes that are most critical for separating one topic from the others (similar to differential expression analysis between clusters), with the following parameter settings: top_features=n, method="poisson", options="min", shared=TRUE. For visualization, the "Score" shown for top genes (FIG. 2c, FIG. 6d) was computed as 100*x, where x is the Kullback-Leibler divergence score output by ExtractTopFeatures( ), and then plotted on a logarithmic scale. Genes were included in the large diffusion map if they were in the top 50 genes for topics 2, 4, 8, 11, 13, or 15, but not in the top 5 genes for any other topics. For the smaller diffusion map (FIG. 3c), cells and genes were selected in an analogous way, but only for the three topics 8, 13, and 15. Overall, the larger diffusion map was computed on 7,888 cells and 245 genes, and the smaller one on 3,785 cells and 130 genes. To build the diffusion map, Applicants gave the expression data for these cells and genes as input to the DiffusionMap( ) function from the destiny R package[64], with parameter settings k=50 and sigma="local".

REFERENCES

1 Nograles, K. E. et al. Th17 cytokines interleukin (IL)-17 and IL-22 modulate distinct inflammatory and keratinocyte-response pathways. Br J Dermatol 159, 1092-1102, doi:10.1111/j.1365-2133.2008.08769.x (2008).
2 Cai, Y. et al. Pivotal role of dermal IL-17-producing gammadelta T cells in skin inflammation. Immunity 35, 596-610, doi:10.1016/j.immuni.2011.08.001 (2011).
3 Teunissen, M. B. M. et al. Composition of innate lymphoid cell subsets in the human skin: enrichment of NCR(+) ILC3 in lesional skin and blood of psoriasis patients. The Journal of investigative dermatology 134, 2351-2360, doi:10.1038/jid.2014.146 (2014).
4 Villanova, F. et al. Characterization of innate lymphoid cells in human skin and blood demonstrates increase of NKp44+ ILC3 in psoriasis. The Journal of investigative dermatology 134, 984-991, doi:10.1038/jid.2013.477 (2014).
5 Pantelyushin, S. et al. Rorgammat+ innate lymphocytes and gammadelta T cells initiate psoriasiform plaque formation in mice. J Clin Invest 122, 2252-2256, doi: 10.1172/JC161862 (2012).
6 Gasteiger, G., Fan, X., Dikiy, S., Lee, S. Y. & Rudensky, A. Y. Tissue residency of innate lymphoid cells in lymphoid and nonlymphoid organs. Science 350, 981-985, doi:10.1126/science.aac9593 (2015).
7 Huang, Y. et al. S1P-dependent interorgan trafficking of group 2 innate lymphoid cells supports host defense. Science 359, 114-119, doi:10.1126/science.aam5809 (2018).
8 Yang, J. et al. Selective programming of CCR10(+) innate lymphoid cells in skin-draining lymph nodes for cutaneous homeostatic regulation. Nature immunology 17, 48-56, doi:10.1038/ni.3312 (2016).
9 Dyring-Andersen, B. et al. Increased number and frequency of group 3 innate lymphoid cells in nonlesional psoriatic skin. Br J Dermatol 170, 609-616, doi:10.1111/bjd.12658 (2014).
10 Li, Z. et al. Epidermal Notch1 recruits RORgamma(+) group 3 innate lymphoid cells to orchestrate normal skin repair. Nat Commun 7, 11394, doi:10.1038/ncomms11394 (2016).
11 Matloubian, M. et al. Lymphocyte egress from thymus and peripheral lymphoid organs is dependent on SIP receptor 1. Nature 427, 355-360, doi:10.1038/nature02284 (2004).
12 Roediger, B. et al. Cutaneous immunosurveillance and regulation of inflammation by group 2 innate lymphoid cells. Nature immunology 14, 564-573, doi:10.1038/ni.2584 (2013).
13 Zhang, K. et al. Cutting Edge: Notch Signaling Promotes the Plasticity of Group-2 Innate Lymphoid Cells. J Immunol 198, 1798-1803, doi:10.4049/jimmunol.1601421 (2017).
14 Huang, Y. et al. IL-25-responsive, lineage-negative KLRG1(hi) cells are multipotential 'inflammatory' type 2 innate lymphoid cells. Nature immunology 16, 161-169, doi:10.1038/ni.3078 (2015).
15 Bernink, J. H. et al. Interleukin-12 and -23 Control Plasticity of CD127(+) Group 1 and Group 3 Innate Lymphoid Cells in the Intestinal Lamina Propria. Immunity 43, 146-160, doi:10.1016/j.immuni.2015.06.019 (2015).
16 Cella, M., Otero, K. & Colonna, M. Expansion of human NK-22 cells with IL-7, IL-2, and IL-1beta reveals intrinsic functional plasticity. Proc Natl Acad Sci USA 107, 10961-10966, doi:10.1073/pnas.1005641107 (2010).
17 Lim, A. I. et al. IL-12 drives functional plasticity of human group 2 innate lymphoid cells. The Journal of experimental medicine 213, 569-583, doi:10.1084/jem.20151750 (2016).
18 Ohne, Y. et al. IL-1 is a critical regulator of group 2 innate lymphoid cell function and plasticity. Nature immunology 17, 646-655, doi:10.1038/ni.3447 (2016).
19 Silver, J. S. et al. Inflammatory triggers associated with exacerbations of COPD orchestrate plasticity of group 2 innate lymphoid cells in the lungs. Nature immunology 17, 626-635, doi:10.1038/ni.3443 (2016).
20 Bal, S. M. et al. IL-1beta, IL-4 and IL-12 control the fate of group 2 innate lymphoid cells in human airway inflammation in the lungs. Nature immunology 17, 636-645, doi:10.1038/ni.3444 (2016).
21 Ciofani, M. et al. A validated regulatory network for Th17 cell specification. Cell 151, 289-303, doi:10.1016/j.cell.2012.09.016 (2012).
22 Li, P. et al. BATF-JUN is critical for IRF4-mediated transcription in T cells. Nature 490, 543-546, doi: 10.1038/nature11530 (2012).

23 Zhong, C. et al. Group 3 innate lymphoid cells continuously require the transcription factor GATA-3 after commitment. Nature immunology 17, 169-178, doi:10.1038/ni.3318 (2016).
24 Blei, D. M., Ng, A. Y., Jordan, M. I. Latent Dirichlet Allocation. Journal of Machine Learning Research 3, 29 (2003).
25 Pritchard, J. K., Stephens, M. & Donnelly, P. Inference of population structure using multilocus genotype data. Genetics 155, 945-959 (2000).
26 Quon, G. et al. Computational purification of individual tumor gene expression profiles leads to significant improvements in prognostic prediction. Genome Med 5, 29, doi:10.1186/gm433 (2013).
27 Repsilber, D. et al. Biomarker discovery in heterogeneous tissue samples—taking the in530 silico deconfounding approach. BMC Bioinformatics 11, 27, doi:10.1186/1471-2105-11-27 (2010).
28 Schwartz, R. & Shackney, S. E. Applying unmixing to gene expression data for tumor phylogeny inference. BMC Bioinformatics 11, 42, doi:10.1186/1471-2105-11-42 (2010).
29 Wang, N. et al. UNDO: a Bioconductor R package for unsupervised deconvolution of mixed gene expressions in tumor samples. Bioinformatics 31, 137-139, doi:10.1093/bioinformatics/btu607 (2015).
30 Shen-Orr, S. S. et al. Cell type-specific gene expression differences in complex tissues. Nature methods 7, 287-289, doi:10.1038/nmeth.1439 (2010).
31 Lindsay, J., Mandoiu, I., Nelson, C. Gene Expression Deconvolution using Single-cells. Proceedings of the 2013 American Association of Human Genetics meeting (2013).
32 Ahn, J. et al. DeMix: deconvolution for mixed cancer transcriptomes using raw measured data. Bioinformatics 29, 1865-1871, doi:10.1093/bioinformatics/btt301 (2013).
33 Dey, K. K., Hsiao, C. J. & Stephens, M. Visualizing the structure of RNA-seq expression data using grade of membership models. PLoS genetics 13, e1006599, doi:10.1371/journal.pgen.1006599 (2017).
34 Wallrapp, A. et al. The neuropeptide NMU amplifies ILC2-driven allergic lung inflammation. Nature 549, 351-356, doi:10.1038/nature24029 (2017).
35 Gury-BenAri, M. et al. The Spectrum and Regulatory Landscape of Intestinal Innate Lymphoid Cells Are Shaped by the Microbiome. Cell 166, 1231-1246 e1213, doi:10.1016/j.cell.2016.07.043 (2016).
36 Carlson, C. M. et al. Kruppel-like factor 2 regulates thymocyte and T-cell migration. Nature 442, 299-302, doi:10.1038/nature04882 (2006).
37 Cao, Z., Sun, X., Icli, B., Wara, A. K. & Feinberg, M. W. Role of Kruppel-like factors in leukocyte development, function, and disease. Blood 116, 4404-4414, doi:10.1182/blood-2010-05-285353 (2010).
38 Galloway, A. et al. RNA-binding proteins ZFP36L1 and ZFP36L2 promote cell quiescence. Science 352, 453-459, doi:10.1126/science.aad5978 (2016).
39 Salerno, F. et al. Translational repression of pre-formed cytokine-encoding mRNA prevents chronic activation of memory T cells. Nature immunology, doi:10.1038/s41590-018-0155-6 (2018).
40 Yosef, N. et al. Dynamic regulatory network controlling TH17 cell differentiation. Nature 496, 461-468, doi:10.1038/nature11981 (2013).
41 Schroder, B. The multifaceted roles of the invariant chain CD74—More than just a chaperone. Biochimica et biophysica acta 1863, 1269-1281, doi:10.1016/j.bbamcr.2016.03.026 (2016).
42 Kuwano, Y. et al. CD83 influences cell-surface MHC class II expression on B cells and other antigen-presenting cells. Int Immunol 19, 977-992, doi:10.1093/intimm/dxm067 (2007).
43 Robinette, M. L. et al. Transcriptional programs define molecular characteristics of innate lymphoid cell classes and subsets. Nature immunology 16, 306-317, doi:10.1038/ni.3094 (2015).
44 Ricardo-Gonzalez, R. R. et al. Tissue signals imprint ILC2 identity with anticipatory function. Nature immunology, doi:10.1038/s41590-018-0201-4 (2018).
45 Kumari, S., Curado, S., Mayya, V. & Dustin, M. L. T cell antigen receptor activation and actin cytoskeleton remodeling. Biochimica et biophysica acta 1838, 546-556, doi:10.1016/j.bbamem.2013.05.004 (2014).
46 Haghverdi, L., Buttner, M., Wolf, F. A., Buettner, F. & Theis, F. J. Diffusion pseudotime robustly reconstructs lineage branching. Nature methods 13, 845-848, doi:10.1038/nmeth.3971 (2016).
47 Trapnell, C. et al. The dynamics and regulators of cell fate decisions are revealed by pseudotemporal ordering of single cells. Nat Biotechnol 32, 381-386, doi:10.1038/nbt.2859 (2014).
48 Sutton, V. R. et al. Serglycin determines secretory granule repertoire and regulates natural killer cell and cytotoxic T lymphocyte cytotoxicity. FEBS J 283, 947-961, doi:10.1111/febs.13649 (2016).
49 Tsukada, J., Yoshida, Y., Kominato, Y. & Auron, P. E. The CCAAT/enhancer (C/EBP) family of basic-leucine zipper (bZIP) transcription factors is a multifaceted highly-regulated system for gene regulation. Cytokine 54, 6-19, doi:10.1016/j.cyto.2010.12.019 (2011).
50 Nussbaum, J. C. et al. Type 2 innate lymphoid cells control eosinophil homeostasis. Nature 502, 245-248, doi:10.1038/nature12526 (2013).
51 Esplugues, E. et al. Control of TH17 cells occurs in the small intestine. Nature 475, 514-518, doi:10.1038/nature10228 (2011).
52 Tusi, B. K. et al. Population snapshots predict early haematopoietic and erythroid hierarchies. Nature 555, 54-60, doi:10.1038/nature25741 (2018).
53 Laurenti, E. & Gottgens, B. From haematopoietic stem cells to complex differentiation landscapes. Nature 553, 418-426, doi:10.1038/nature25022 (2018).
54 Carrelha, J. et al. Hierarchically related lineage-restricted fates of multipotent haematopoietic stem cells. Nature 554, 106-111, doi:10.1038/nature25455 (2018).
55 Buenrostro, J. D., Giresi, P. G., Zaba, L. C., Chang, H. Y. & Greenleaf, W. J. Transposition of native chromatin for fast and sensitive epigenomic profiling of open chromatin, DNA binding proteins and nucleosome position. Nature methods 10, 1213-1218, doi:10.1038/nmeth.2688 (2013).
56 Langmead, B. & Salzberg, S. L. Fast gapped-read alignment with Bowtie 2. Nature methods 9, 357-359, doi:10.1038/nmeth.1923 (2012).
57 Zhang, Y. et al. Model-based analysis of ChIP-Seq (MACS). Genome Biol 9, R137, doi:10.1186/gb-2008-9-9-r137 (2008).
58 Thorvaldsdottir, H., Robinson, J. T. & Mesirov, J. P. Integrative Genomics Viewer (IGV): high-performance genomics data visualization and exploration. Brief Bioinform 14, 178-192, doi:10.1093/bib/bbs017 (2013).

59 Robinson, J. T. et al. Integrative genomics viewer. Nat Biotechnol 29, 24-26, doi:10.1038/nbt.1754 (2011).
60 Liu, T. et al. Cistrome: an integrative platform for transcriptional regulation studies. Genome Biol 12, R83, doi:10.1186/gb-2011-12-8-r83 (2011).
61 Pandey, S., Shekhar, K., Regev, A. & Schier, A. F. Comprehensive Identification and Spatial Mapping of Habenular Neuronal Types Using Single-Cell RNA-Seq. Curr Biol 28, 1052-1065 e1057, doi:10.1016/j.cub.2018.02.040 (2018).
62 Butler, A., Hoffman, P., Smibert, P., Papalexi, E. & Satija, R. Integrating single-cell transcriptomic data across different conditions, technologies, and species. Nat Biotechnol 36, 411-420, doi:10.1038/nbt.4096 (2018).
63 Taddy, M. On Estimation and Selection for Topic Models. Proceedings of Machine Learning Research 22, 1184-1193 (2012).
64 Angerer, P. et al. destiny: diffusion maps for large-scale single-cell data in R. Bioinformatics 32, 1241-1243, doi:10.1093/bioinformatics/btv715 (2016).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed:

1. A method of treating skin inflammation by reducing an innate lymphoid cell (ILC) inflammatory response in a subject in need thereof, comprising administering CGRP, thereby modulating a shift of naïve/quiescent ILC cells to type 2 ILC (ILC2) cells, wherein CGRP comprises β-CGRP.

2. The method of claim 1, wherein the skin inflammation is psoriasis.

3. The method of claim 1, wherein the naïve/quiescent ILC cells are characterized by expression of one or more genes or gene products selected from the group consisting of: Klf2, Klf4, Tsc22d3, Zfp36l2, and CebpbU.

4. The method of claim 1, wherein the CGRP is administered topically.

5. The method of claim 1, wherein the skin inflammation is atopic dermatitis.

6. The method of claim 1, wherein the CGRP is administered as a time release composition.

7. The method of claim 1, wherein the naïve/quiescent ILC cells are characterized by expression of one or more gene products selected from the group consisting of Ubb, Junb, Klf2, Dusp1, Fos, Rgs2, Klf4, Ubc, Zfp36, Zfp36l2, Fosb, Rgcc, Atf3, Jund, Nr4a1, Ier2, Crip1, Csmp1, Pnrc1 and Tsc22d3.

8. The method of claim 1, wherein the ILC2 cells are characterized by expression of one or more genes or gene products selected from the group consisting of Il5 and Il13.

9. The method of claim 1, wherein the ILC2 cells are characterized by expression of one or more genes or gene products selected from the group consisting of Cxcl2, Actg1, Hilpda, Pim1, Nr4a1, Il5, Gm20186, Ly6a, Malat1, Satb1, Odc1, Srgn, Il1rl1, H2-Q7, Kdm6b, Cd3e, Cxcl10, Gdd45b, Vps37b and Pdcd1.

10. A method of treating skin inflammation by reducing an innate lymphoid cell (ILC) inflammatory response in a subject in need thereof comprising administering CGRP, thereby modulating a shift of ILC2 cells to ILC3-like cells, wherein CGRP comprises β-CGRP.

11. The method of claim 10, wherein the skin inflammation is psoriasis.

12. The method of claim 10, wherein the skin inflammation is atopic dermatitis.

13. The method of claim 10, wherein the CGRP is administered topically.

14. The method of claim 10, wherein the CGRP is administered as a timed release composition.

15. The method of claim 10, wherein the ILC2 cells are characterized by expression of one or more genes or gene products selected from the group consisting of Il5 and Il13.

16. The method of claim 10, wherein the ILC2 cells are characterized by expression of one or more genes or gene products selected from the group consisting of Cxcl2, Actg1, Hilpda, Pim1, Nr4a1, Il5, Gm20186, Ly6a, Malat1, Satb1, Odc1, Srgn, Il1rl1, H2-Q7, Kdm6b, Cd3e, Cxcl10, Gdd45b, Vps37b and Pdcd1.

17. The method of claim 10, wherein the ILC3-like cells are characterized by expression of one or more genes or gene products selected from the group consisting of Srgn, Il13, Il17 and Il22.

18. The method of claim 10, wherein the ILC3-like cells are characterized by expression of one or more genes or gene products selected from the group consisting of Il22, Il17f, Il17a, Gzmb, Ly6a, Timp1, Iltifb, Cxcl2, Gzmc, Gm1045, Cystm1, Cryba4, Ccr5, Il13, Hsd17b10, Dnaja1, Tnfrsf8, Cyb5a, Serpine2 and Srgn.

19. A method of treating skin inflammation by reducing an innate lymphoid cell (ILC) inflammatory response in a subject in need thereof comprising administering CGRP, thereby shifting ILC3-like cells to ILC2 cells, naïve/quiescent ILC cells, or a combination thereof, wherein CGRP comprises β-CGRP.

20. The method of claim 19, wherein the skin inflammation is psoriasis.

21. The method of claim 19, wherein the skin inflammation is atopic dermatitis.

22. The method of claim 19, wherein the CGRP is administered topically.

23. The method of claim 19, wherein the CGRP is administered as a timed release composition.

24. The method of claim 19, wherein the naïve/quiescent ILC cells are characterized by expression of one or more genes or gene products selected from the group consisting of Klf2, Klf4, Tsc22d3, Zfp36l2, and Cebpb.

25. The method of claim 19, wherein the naïve/quiescent ILC cells are characterized by expression of one or more genes or gene products selected from the group consisting Ubb, Junb, Klf2, Dusp1, Fos, Rgs2, Klf4, Ubc, Zfp36, Zfp36l2, Fosb, Rgcc, Atf3, Jund, Nr4a1, Ier2, Crip1, Csmp1, Pnrc1 and Tsc22d3.

26. The method of claim 19, wherein the ILC3-like cells are characterized by expression of one or more genes or gene products selected from the group consisting of Il22, Il17f, Il17a, Gzmb, Ly6a, Timp1, Iltifb, Cxcl2, Gzmc, Gm1045, Cystm1, Cryba4, Ccr5, Il13, Hsd17b10, Dnaja1, Tnfrsf8, Cyb5a, Serpine2 and Srgn.

27. The method of claim 19, wherein the ILC3-like cells are characterized by expression of one or more genes or gene products selected from the group consisting of Srgn, Il13, Il17 and Il22.

28. The method of claim 19, wherein the ILC2 cells are characterized by expression of one or more genes or gene products selected from the group consisting of Il5 and Il13.

29. The method of claim 19, wherein the ILC2 cells are characterized by expression of one or more genes or gene products selected from the group consisting of Cxcl2, Actg1, Hilpda, Pim1, Nr4a1, Il5, Gm20186, Ly6a, Malat1, Satb1, Odc1, Srgn, Il1rl1, H2-Q7, Kdm6b, Cd3e, Cxcl10, Gdd45b, Vps37b and Pdcd1.

* * * * *